United States Patent
Yoshimura et al.

(10) Patent No.: US 7,144,720 B2
(45) Date of Patent: Dec. 5, 2006

(54) PROTEIN AND DNA THEREOF

(75) Inventors: Koji Yoshimura, Tsukuba (JP); Yuichi Hikichi, Tsukuba (JP); Atsushi Nishimura, Tsukuba (JP)

(73) Assignee: Takeda Chemical Industries, Ltd., Osaka (JP)

( * ) Notice: Subject to any disclaimer, the term of this patent is extended or adjusted under 35 U.S.C. 154(b) by 57 days.

(21) Appl. No.: 11/088,999

(22) Filed: Mar. 24, 2005

(65) Prior Publication Data

US 2005/0186618 A1 Aug. 25, 2005

Related U.S. Application Data

(62) Division of application No. 10/726,148, filed on Dec. 2, 2003, which is a division of application No. 09/786,256, filed as application No. PCT/JP99/04766 on Sep. 2, 1999, now Pat. No. 6,680,189.

(30) Foreign Application Priority Data

Sep. 3, 1998 (JP) ................................ 10-250115

(51) Int. Cl.
- *C12N 9/50* (2006.01)
- *C12N 15/00* (2006.01)
- *C12N 1/20* (2006.01)
- *C12Q 1/68* (2006.01)
- *C07H 21/04* (2006.01)

(52) U.S. Cl. ................. 435/219; 435/252.3; 435/320.1; 435/6; 536/23.2

(58) Field of Classification Search ................ 435/219, 435/6, 252.3, 320.1; 536/23.2
See application file for complete search history.

(56) References Cited

U.S. PATENT DOCUMENTS 5,990,293 A 11/1999 Docherty et al.

FOREIGN PATENT DOCUMENTS

WO WO-97/09430 3/1997

OTHER PUBLICATIONS

GENBANK Accession No. A61275, "Sequence 1 from Patent WO9709430," (Mar. 1998).

Hite, et al., "Sequence of a cDNA clone encoding the zinc metalloprotease hemorrahgic toxin e from Crotalus atrox: Evidence for signal, zymogen and disintegrin-like structures," Biochemistry 31:6203-6211 (1992).

Howard, et al., "Molecular cloning of MADM: a catalytically active mammalian disintegrin-metalloprotease expressed in various cell types," Biochem. J. 317:45-50 (1996).

Kratzschmar, et al., "Metargidin, a membrane-anchored metalloprotease-disintegrin protein with an RGD integrin binding sequence," J. Biol. Chem. 271(9):4593-4596 (1996).

Paine, M.J.I. et al., "Cloning of metalloprotease genes in the carpet viper (*Echis pyramidum leakeyi*): Further members of the metalloprotease/disintegrin gene family," Eur. J. Biochem. 224:483-488 (1994).

Wolfsberg, T.J. et al., "ADAM, a novel family of membrane proteins containing a disintegrin and metalloprotease domain: Multipotential functions in cell-cell and cell-matrix interactions," J. Cell Biol. 131:275-278 (1995).

*Primary Examiner*—Maryam Monshipouri
(74) *Attorney, Agent, or Firm*—Human Genome Sciences, Inc.

(57) ABSTRACT

The present invention relates to a novel protein belonging to an ADAM family, a partial peptide thereof or a salt thereof, a DNA encoding the protein, a recombinant vector comprising the DNA, a transformant, a method for producing the protein, a medicine comprising the protein or the DNA, an antibody against the protein, a method/kit for screening for a compound or a salt thereof which promotes or inhibits the protease activity or the extracellular metric degrading enzyme activity (preferably, the peptidoglycan degrading enzyme activity) of the protein, a compound obtained by the screening, and a medicine comprising the compound. The present protein and a DNA encoding it can be used, for example, as an agent for treating or preventing various diseases such as disc herniation, ischialgia, glomerular nephritis, diabetic nephropathy, hepatic fibrosis, pulmonary fibrosis or osteopetrosis. In addition, the present antibody can be used for quantitating the present protein in a test solution. Further, the present protein is useful as a reagent for screening for a compound which promotes or inhibits the protease activity of the present protein.

16 Claims, 5 Drawing Sheets

```
     1330       1340       1350       1360       1370       1380       1390       1400       1410       1420       1430       1440
TGTGGACACTCTGAGAATGTACCATATTGCTCTGATCCTAAGACATGTAAAATCAAAGCAACTTTCAATGTCCATTAGGAGACATTTCTGAAAATGCCAATTAAAAACCCTGG
 C  G  T  S  E  E  C  T  N  I  C  C  D  A  K  T  C  K  I  K  A  T  F  Q  C  A  L  G  E  C  C  E  K  C  Q  F  K  K  A  G 1450       1460       1470       1480       1490       1500       1510       1520       1530       1540       1550       1560
ATGCTGTCCGACCAGCAAAAGATGAGTCGGGACCTGCCTGAAATGTGTAATGGTAAATCTGGAAATTGTCCTGATGATAGATTCCAAGTCAATGGCTTCCTTGCCATCACGGAAGGC
 M  V  C  R  P  A  K  D  E  C  D  L  P  E  M  C  N  G  K  S  G  N  C  P  D  D  R  F  Q  V  N  G  F  P  C  H  H  G  K  G 1570       1580       1590       1600       1610       1620       1630       1640       1650       1660       1670       1680
CACTTGTTGATGGGACAATGCCCCACAACTGCAGGACCTGGGACCAGTGCACAGAGCTGTGGGGACCAGTCCACAGACCAGAAATCCTTCCCCGTCCATGCGAAGGAAAATCATTTCAGATGACAG
 H  C  L  M  G  T  C  P  T  L  Q  E  Q  C  T  E  L  W  G  P  G  R  R  T  N  P  F  P  C  A  C  A  K  E  N  H  F  R  *

1690       1700       1710       1720       1730       1740       1750       1760       1770       1780       1790       1800
TGTTTAACCATTGTCAAAGGACCATTGTCTATCCTTCTAGAAGCTTCGACTCAAAATCATGAAAGTTTAACATTGAGTTGTTTGACGGTTGCTAGATTAGCAAGTAAA 1810       1820       1830       1840       1850       1860       1870       1880       1890       1900       1910       1920
AATAAGGACCCCCGTAAATTTAACTAAAATATTTTTGTTTTTGTCTCAGCATCAGTATATCCATTGCAATACTTGAGGTGCTCTCATACTAAAATT 1930       1940       1950       1960       1970       1980       1990       2000       2010       2020       2030       2040
ATTTGTATCTGAAATTCAAATTAAAACTGGGTGTCTTTTTCTTTCATCTCCAACCTACTAAGATCATAAAACCCTTGGAAATTCTGTGTGTGTCCGGGTGTGTGTGTGTG 2050       2060       2070       2080       2090       2100       2110       2120       2130       2140       2150       2160
CACGGGTGCAGAAGTACTGTGTGGGATGGATGGGACAGAAATAACGAAATAATCTCGAAATGCAGAAGCCCAATAAAGAAAGTGAAAGTCTAAAGTGCCTTTG 2170       2180       2190       2200       2210       2220       2230       2240       2250       2260       2270       2280
TCCATAATGCCAAAATTTAGAGACCATATTCTTAATTCACCAAGAAACTTGAAAAATAAAGTTAAAGAGATTATCCGAAAATTGTATAGTATTAAATAACTT 2290       2300       2310       2320       2330       2340       2350       2360       2370       2380       2390       2400
TGGCCAGGTGCGGTGGCTCACACCTGTAATCCCAGCACTTTGGGAGGCCGAGGTCAGGAGATCAAGACCATCCTGGCTACCACGGTGAAACCCGTCTCTACTA 2410       2420       2430       2440       2450       2460       2470       2480       2490       2500       2510       2520
AAAATACAAAAATTAGCCGGGCGTGGTGGCGGGCGCCTGTAGTGGCGGCTACTCGGGAGGCTGAGGCAGGAGAATGGCGTGAACCCGGGAGGCGGAGCTTGCAGTGAGCCGACTTGCCGTCAGCAGAGATTGCCA 2530       2540       2550       2560
CTGCACTCCAGCCTGGGTGACAAAGCCGAGACTCCGTTCC
```

PROTEIN AND DNA THEREOF

CROSS-REFERENCE TO RELATED APPLICATIONS

This application is a divisional of U.S. patent application Ser. No. 10/726,148, filed Dec. 2, 2003, pending, which is a divisional of U.S. patent application Ser. No. 09/786,256, filed May 10, 2001, now U.S. Pat. No. 6,680,189, which is the National Stage of International Application No. PCT/JP99/04766, filed Sep. 2, 1999.

TECHNICAL FIELD

The present invention relates to a novel ADAM protein.

BACKGROUND ART

An extracellular matrix is a cell-supporting tissue surrounding cells of the tissue and is composed of a fibrous protein such as collagen and elastin, a complex carbohydrate such as proteoglycan, a glycoprotein such as fibronectin and laminin, which relate to cell-adhesion, and a sugar such as hyaluronic acid. The exracellular matrix is known to have the important influence of activities of cells such as shape, metabolism, migration, proliferation and differentiation. Therefore, the extracellular matrix is known to be associated with many living body phenomena such as development, aging, inflammation, wound healing, immunity and tumor of the living body. It is known that the abnormal degradation of the extracellular matrix occurs in a variety of diseases such as rheumatoid arthritis, osteoarthritis, osteoporosis, cancer metastasis and infiltration, arteriosclerosis and corneae ulcer. There is a possibility that regulation of the enzyme activities involved in degradation of the extracellular matrix produces a therapeutic agent for these diseases.

ADAM (A disintegrin and metalloprotease) family proteins have the similar structure to that of hemorrhagic venom and are composed of a metalloprotease region and a disintegrin region. Many of ADAM family proteins are membrane proteins and 10 or more cDNAs have been isolated from a variety of organisms (T. G. Wolfsberg et al., Journal of Cell Biology 131:275–278, 1995). The physiological functions of ADAM proteins are known to be involved in cell fusion, cell differentiation, host defense and the like. That is, Fertilin, which is an ADAM expressed on a sperm, is associated with adhesion of an egg and sperm by binding to integrin α6β1 on an egg via a disintegrin region (D. Myles et al., Proc. Natl. Acad. Sci. USA 91:4195–4198, 1994). A disintegrin region of meltrin is reported to be associated with fusion of myocyte (T. Yagami-Hiromasa et al., Nature 377: 652–656, 1995). In addition, KUZ, which is an ADAM protein of *Drosophila* is associated with differentiation of nerve (J. Rooke et al., Science 273:1227–1230, 1996). In addition, TNF-α convertase (R. A. Black et al, Nature 385:729–733, 1997) and ADAM 10 (C. A. Lunn et al., FEBS letter 40:333–335, 1997) are reported to cleave a TNF-α precursor to convert it into a secreted type.

New human-derived ADAM family proteins enable development of new medicines which have the activity of regulating the activities of those proteins and are useful for preventing or treating joint diseases such as a variety of diseases based on those activities, for example, rheumatoid arthritis and osteoarthritis. Therefore, there has been desired finding of human-derived novel ADAM proteins and development of a process for mass-production of them in the art of the present invention.

DISCLOSURE OF INVENTION

In order to solve the above problems, the present inventors studied intensively and, as a result, found an ADAM gene having a novel base sequence and found that an ADAM protein encoded by it has the protease activity and is involved in degradation of an extracellular matrix. Based on these findings, the present inventors further studied and, as a result, completed the present invention.

That is, the present invention provides:

(1) a protein or a salt thereof which has an amino acid identical to or substantially identical to an amino acid sequence represented by SEQ ID No: 2, (2) the protein or a salt thereof according to the above (1), which has an amino acid identical to or substantially identical to an amino acid represented by SEQ ID No: 2 as a disintegrin region, (3) the protein or a salt thereof according to the above (1), which belongs to an ADAM family, (4) the protein or a salt thereof according to the above (1), which has an amino acid sequence identical or substantially identical to an amino acid sequence represented by SEQ ID No: 1 or SEQ ID No: 15, (5) the protein or a salt thereof according to the above (1), which has the protease activity, (6) a partial peptide of the protein according to the above (1), which has an amino acid sequence identical or substantially identical to an amino acid sequence represented by SEQ ID No: 6, or a salt thereof, (7) a DNA which has a DNA having a base sequence encoding a protein having an amino acid sequence identical or substantially identical to an amino acid sequence represented by SEQ ID No: 2, (8) the DNA according to the above (7), which has a base sequence represented by SEQ ID No: 3 or SEQ ID No: 16, (9) a DNA which has a DNA encoding the partial peptide according to the above (6),

(10) the DNA according to the above (9), which has a base sequence represented by SEQ ID No: 4,

(11) a recombinant vector which has the DNA according to the above (7),

(12) a transformant transformed with the recombinant vector according to the above (11),

(13) a method for producing the protein or a salt according to the above (1), which comprises culturing the transformant according to the above (12) to produce the protein according to the above (1),

(14) an antibody against the protein or a salt thereof according to the above (1) or the partial peptide or a salt thereof according to the above (6),

(15) a diagnostic agent which comprises the DNA according to the above (7) or the antibody according to the above (14),

(16) an agent which comprises the protein or a salt thereof according to the above (1) or the partial peptide or a salt thereof according to the above (6),

(17) a medicine which comprises the protein or a salt thereof according to the above (1) or the partial peptide or a salt thereof according to the above (6),

(18) the medicine according to the above (17), which is an agent for preventing or treating disc herniation, ischialgia, glomerular nephritis, diabetic nephropathy, hepatic fibrosis, pulmonary fibrosis or osteopetrosis,

(19) a method for screening for a compound or a salt thereof which promotes or inhibits the protease activity, which comprises using the protein according to the above (1) or a salt thereof,

(20) a kit for screening for a compound or a salt thereof which promotes or inhibits the protease activity, which comprises the protein according to the above (1) or a salt thereof,

(21) a compound or a salt thereof which promotes or inhibits the protease activity and is obtainable by using the method for screening according to the above (19) or the kit for screening according to the above (20),

(22) a medicine which comprises a compound or a salt which promotes or inhibits the protease activity and is obtainable by the method for screening according to the above (19) or the kit for screening according to the above (20),

(23) an agent for degrading an extracellular matrix, which comprises a protein having an amino acid identical or substantially identical to an amino acid sequence represented by SEQ ID No: 5, or a salt thereof,

(24) the agent according to the above (23), wherein the extracellular matrix is a proteoglycan,

(25) the agent according to the above (23), which is a pharmaceutical composition,

(26) the agent according to the above (23), which is an agent for preventing or treating disc herniation, ischialgia, glomerular nephritis, diabetic nephropathy, hepatic fibrosis, pulmonary fibrosis or osteopetrosis,

(27) a method for screening for a compound or a salt thereof which promotes or inhibits the extracellular matrix degrading enzyme activity, which comprises using a protein having an amino acid sequence identical or substantially identical to an amino acid sequence represented by SEQ ID No: 5, or a salt thereof,

(28) a kit for screening for a compound or a salt thereof which promotes or inhibits the extracellular matrix degrading enzyme activity, which comprises a protein having an amino acid sequence identical or substantially identical to an amino acid sequence represented by SEQ ID No: 5, or a salt thereof,

(29) a compound or a salt thereof which promotes or inhibits the extracellular matrix degrading enzyme activity, which is obtainable by the method for screening according to the above (27) or the kit for screening according to the above (28),

(30) a medicine which comprises a compound or a salt thereof which promotes or inhibits the extracellular matrix degrading enzyme activity, and is obtainable by the method for screening according to the above (27) or the kit for screening according to the above (28),

(31) a diagnostic agent which comprises an antibody against a protein having an amino acid sequence identical or substantially identical to an amino acid sequence represented by SEQ ID No: 5, or a salt thereof,

(32) a method for detecting a proteoglycan degrading enzyme gene, which comprises mixing and culturing a transformant in which a test gene is introduced and an animal-derived cell producing cartilage or cartilage matrix, and measuring glycosaminoglycan sulfate in the culture supernatant,

(33) a method for screening for an agent for inhibiting or promoting the proteoglycan degrading enzyme activity, which comprises mixing and culturing (i) a recombinant in which a gene encoding a protein having the proteoglycan degrading enzyme activity is introduced, (ii) an animal-derived cell producing cartilage or cartilage matrix, and (iii) a test compound, and measuring glycosaminoglycan sulfate in the culture supernatant,

(34) a method for screening for an agent for inhibiting or promoting the proteoglycan degrading enzyme activity, which comprises mixing and culturing (i) an animal cell comprising (a) the DNA according to the above (7), or (b) a DNA comprising a DNA having a base sequence encoding a protein comprising an amino acid sequence identical or substantially identical to an amino acid sequence represented by SEQ ID No: 5, (ii) an animal-derived cell producing cartilage or cartilage matrix, and (iii) a test compound, and measuring an amount of glycosaminoglycon sulfate in the supernatant,

(35) a non-human mammal which has a DNA having a DNA having a base sequence encoding a protein having an amino acid sequence identical or substantially identical to an amino acid sequence represented by SEQ ID No: 2, or a its mutated DNA,

(36) the animal according to the above (35), which may express a protein having an amino acid sequence identical or substantially identical to an amino acid sequence represented by SEQ ID No: 2, and so forth.

Further, the present invention provides:

(37) the protein according to the above (1), wherein the amino acid sequence substantially identical to an amino acid sequence represented by SEQ ID No: 2 is an amino acid sequence having about 95% or more, preferably about 98% or more homology with an amino acid sequence represented by SEQ ID No: 2,

(38) the protein according to the above (1), wherein the amino acid sequence substantially identical to an amino acid sequence represented by SEQ ID No: 2 is (a) an amino acid sequence in which 1 to 5 (preferably, 1 to 3) amino acids in an amino acid sequence represented by SEQ ID No: 2 are deleted, (b) an amino acid sequence in which 1 to 5 (preferably, 1 to 3) amino acids are added to an amino acid sequence represented by SEQ ID No: 2, (c) an amino acid sequence in which 1 to 5 (preferably, 1 to 3) amino acids in an amino acid sequence represented by SEQ ID No: 2 are substituted with other amino acids, or (d) an amino acid sequence as a combination thereof,

(39) a DNA which comprises a DNA having a base sequence which hybridizes with a base sequence encoding the DNA according to the above (7) or (9) under the highly stringent conditions,

(40) a recombinant vector which comprises the DNA according to the above (39),

(41) a transformant transformed with the recombinant vector according to the above (40),

(42) a method for producing a protein encoded by the DNA according to the above (39) or a salt thereof, which comprises culturing the transformant according to the above (41), and producing and accumulating a protein encoded by the DNA according to the above (39), followed by collecting this,

(43) a protein encoded by the DNA according to the above (39) or a salt thereof, which is produced by the method for producing according to the above (42),

(44) the method for screening according to the above (19), which comprises measuring the protease activity (i) when a substrate is contacted with the protein according to the above (1), the partial peptide according to above (6) or a salt thereof, and the protease activity (ii) when a substrate and a test compound are contacted with the protein according to the above (1), the partial peptide according to the above (6) or a salt thereof, and comparing them,

(45) a medicine which comprises a compound or a salt thereof, which promotes the protease activity of the protein according to the above (1), the partial peptide according to the above (6) or a salt thereof, which is obtained by using the method for screening according to the above (19) or the kit for screening according to the above (20),

(46) the medicine according to the above (45), which is an agent for treating or preventing disc herniation, ischialgia, glomerular nephritis, diabetic nephropathy, hepatic fibrosis, pulmonary fibrosis or osteopetrosis,

(47) a medicine which comprises a compound or a salt thereof, which inhibits the protease activity of the protein according to the above (1), the partial peptide according to the above (6) or a salt thereof, which is obtained by the method for screening according to the above (19) or the kit for screening according to the above (20),

(48) the medicine according to the above (47), which is an agent for treating or preventing rheumatoid arthritis, osteoarthritis, osteoporosis, cancer, arteriosclerosis or corneae ulcer,

(49) a method for quantitating the protein according to the above (1), the partial peptide according to the above (6) or a salt thereof in a test solution, which comprises competitively reacting the antibody according to the above (14) with a test solution and the labeled protein according to the above (1), the partial peptide according to the above (4) or a salt thereof, and measuring a rate of the labeled protein according to the above (1), the partial peptide according to the above (4) or a salt thereof, which is bound to the antibody,

(50) a method for quantitating the protein according to the above (1), the partial peptide according to the above (6) or a salt thereof in a test solution, which comprises reacting simultaneously or successively a test solution with the antibody according to the above (14) insolubilized on a carrier and the labeled antibody according to the above (14) and, thereafter, measuring the activity of a label on the insolubilized carrier,

(51) a medicine which comprises the antibody according to the above (14),

(52) an antisense DNA which has a base sequence complementary or substantially complementary to the DNA according to the above (7), (9) or (39), and has the activity of being capable of inhibiting expression of the DNA,

(53) the antisense DNA according to the above (52), wherein the base sequence complementary or substantially complementary to the DNA according to the above (7), (9) or (39) is a base sequence having about 95% or more, preferably about 98% or more homology with a entire base sequence or a partial base sequence of a base sequence complementary to the DNA,

(54) a medicine which comprises the antisense DNA according to the above (52),

(55) a method for quantitating a protein or a salt thereof, comprising an amino acid sequence identical or substantially to an amino acid sequence represented by SEQ ID No: 5 in a test solution, which comprises competitively reacting an antibody against a protein comprising an amino acid sequence identical or substantially to an amino acid sequence represented by SEQ ID No: 5 or a salt thereof with a test solution and a labeled protein comprising an amino acid sequence identical or substantially to an amino acid sequence represented by SEQ ID No: 5 or a salt thereof, and measuring a ratio of the labeled protein containing amino acid identical or substantially to an amino acid sequence represented by SEQ ID No: 5 or a salt thereof which is bound to the antibody,

(56) a method for quantitating a protein comprising an amino acid sequence identical or substantially to an amino acid sequence represented by SEQ ID No: 5 or a salt thereof in a test solution, which comprises simultaneously or successively reacting a test solution with an antibody against a protein comprising an amino acid sequence identical or substantially to an amino acid sequence represented by SEQ ID No: 5 or a salt thereof which is insolubilized on a carrier and an antibody against a labeled protein comprising an amino acid sequence identical or substantially to an amino acid sequence represented by SEQ ID No: 5 or a salt thereof and, thereafter, measuring the activity of a label on the insolubilized carrier,

(57) a medicine which comprises an antibody against the protein comprising an amino acid sequence identical or substantially to an amino acid sequence represented by SEQ ID No: 5, or a salt thereof, and so forth.

BRIEF DESCRIPTION OF DRAWINGS

FIG. 1 shows a base sequence of a DNA (SEQ ID No:29) encoding a protein belonging to an ADAM family of the present invention, the specific coding region (bp 55-2379; SEQ ID No:16) and an amino acid sequence encoded by it (SEQ ID No:15) (continued to FIG. 2).

FIG. 2 shows a base sequence of a DNA encoding a protein belonging to an ADAM family of the present invention and an amino acid sequence encoded by it (continued from FIG. 1).

Figure 3:
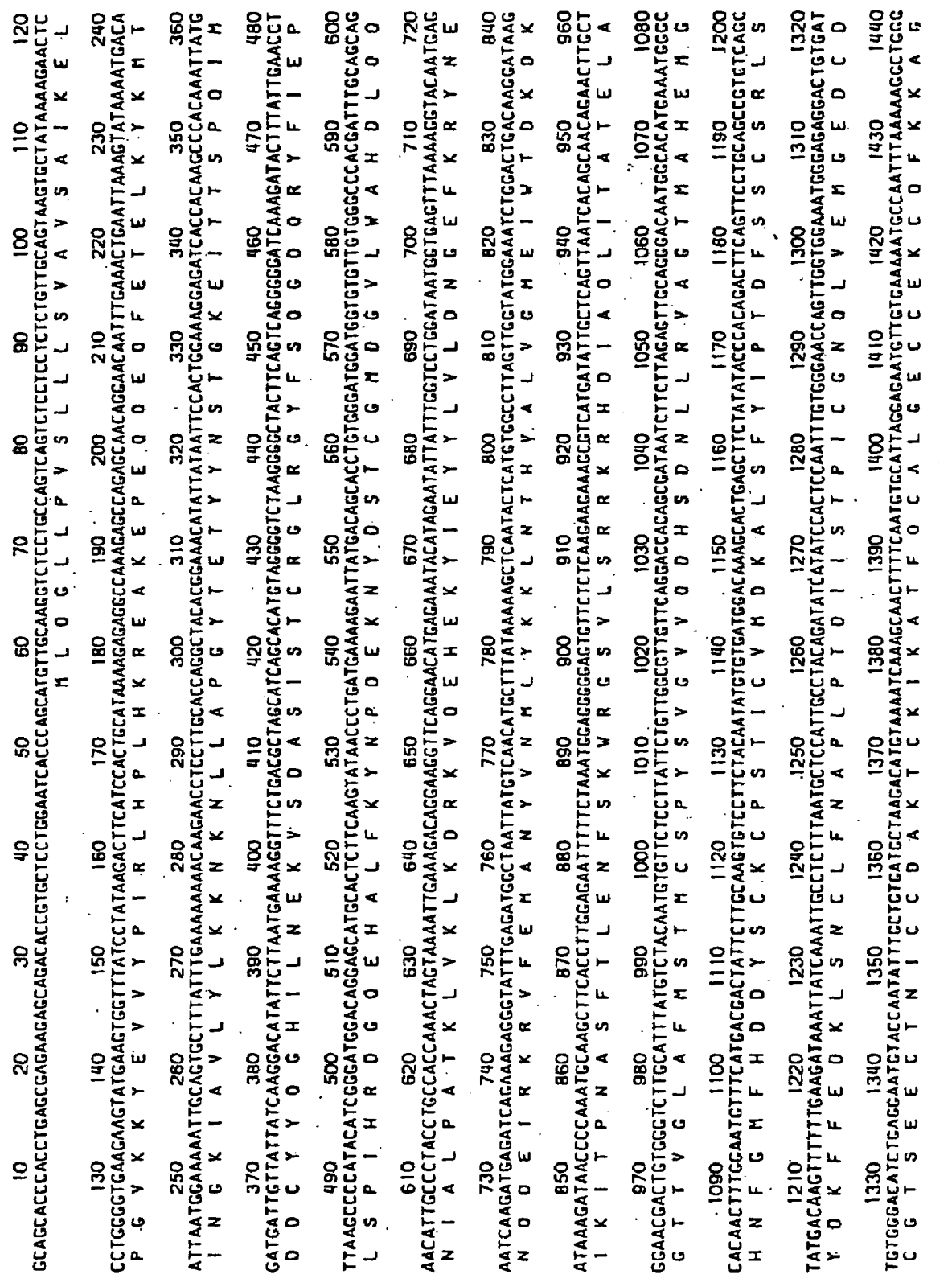

FIG. 3 shows a base sequence of a DNA (SEQ ID No:31) encoding a protein belonging to an ADAM family of the present invention, the specific coding region (bp 55-2379; SEQ ID No:16) and an amino acid sequence encoded by it (SEQ ID No: 15) (continued to FIG. 4).

Figure 4:
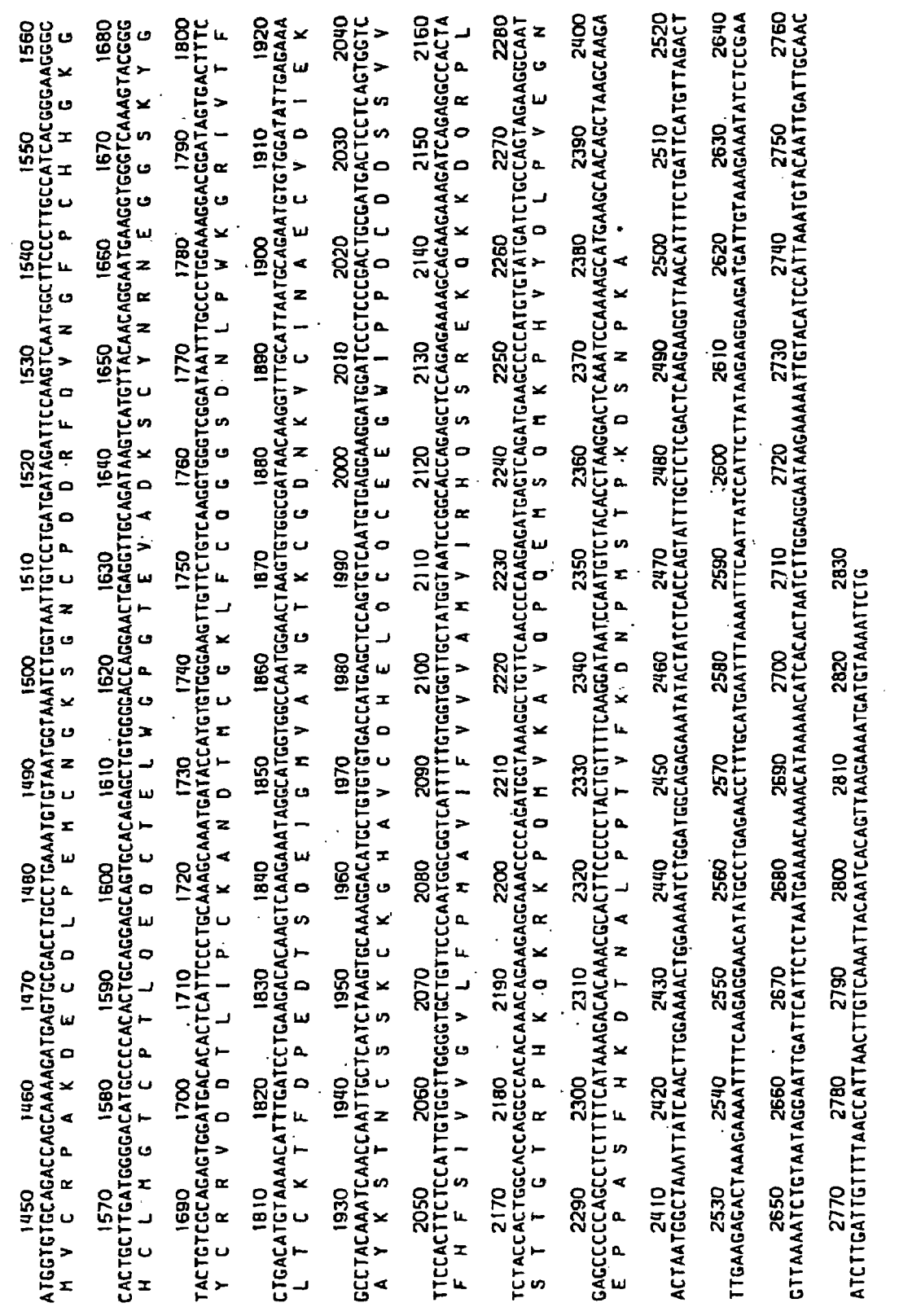

FIG. 4 shows a base sequence of a DNA encoding a protein belonging to an ADAM family of the present invention and an amino acid sequence encoded by it (continued from FIG. 3).

BEST MODE FOR CARRYING OUT THE INVENTION

Figure 5:
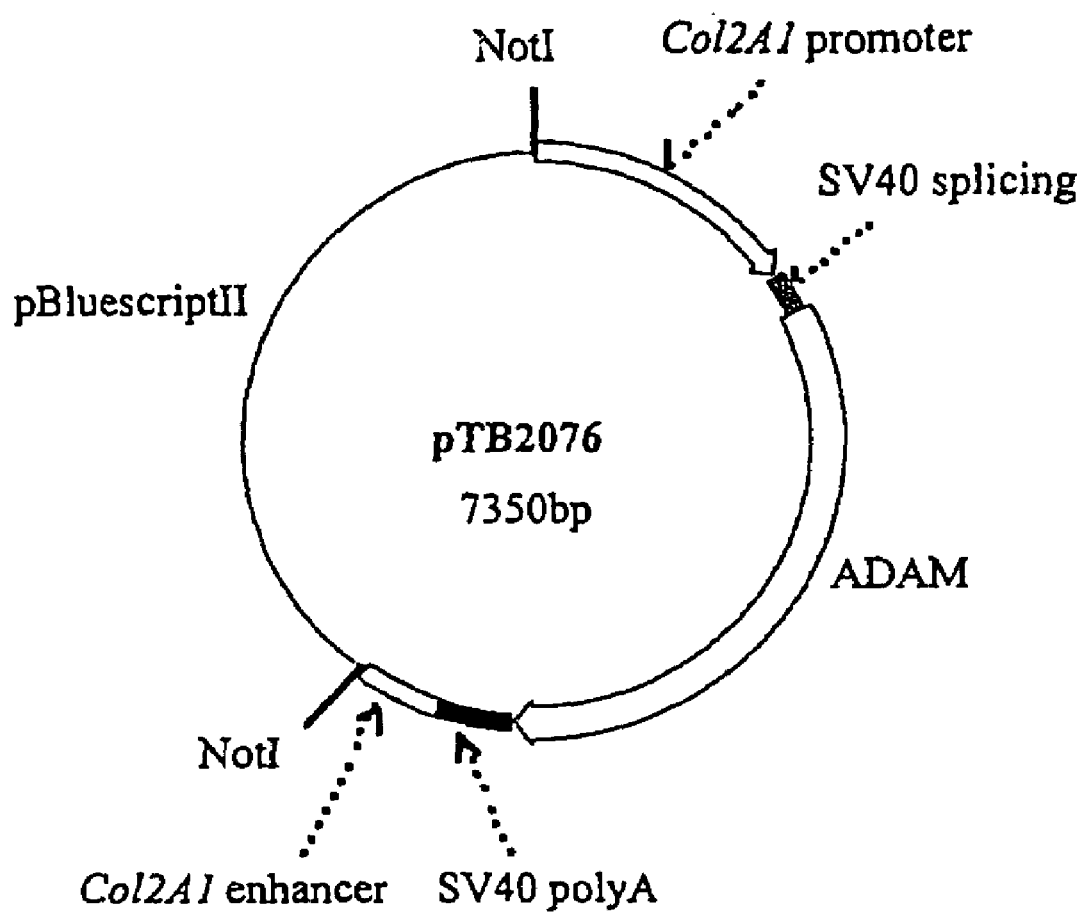
FIG. 5 is a construction view of a vector (pTB2076) made in Example 9.

A protein which has an amino acid sequence identical or substantially identical to an amino acid sequence represented by SEQ ID No: 1, SEQ ID No: 2, SEQ ID No: 5 or SEQ ID No: 15 of the present invention (hereinafter referred to as present protein) may be a protein derived from cells (for example, liver cell, spleen cell, neural cell, glia cell, pancreatic β cell, born marrow cell, mesangial cell, Langerhans cell, epidermic cell, epithelial cell, endothelial cell, fibroblast, fibrocyte, miosite, fat cell, immune cell (e.g., macrophage, T cell, B cell, natural killer cell, mast cell, neutrophils, basophils, eosinophils, and monocyte), megakaryocyte, synovial cell, cartilage cell, osteocyte, osteoblast, osteoclast, mammary gland cell, lever cell or interstitial cell or a precursor cell, a stem cell or a cancer cell of these cells) or all tissues in which these cells are present, for example, brain, each part of brain (e.g., olfactory bulb, almond nucleus, cerebral basal bulb, hippocampus, thalamus, hypothalamus, cerebral cortex, medulla oblongata, and cerebellum), spinal cord, pituitary gland, stomach, pancreas, kidney, lever, gonad, thyroid gland, gallbladder, born marrow, adrenal gland, skin, muscle, lung, digestive tract (e.g., large intestine and small intestine), blood vessel, heart, thymus, spleen, submanbibular gland, peripheral blood, prostate, testis, ovary, placenta, uterus, bone, joint, skeletal muscle, or hemocyte or cultured cell thereof (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01 and so on) of human being and warm blood animal (e.g., guinea pig, rat, mouse, chicken, rabbit, pig, sheep, cow, and monkey), or a synthetic protein.

Examples of the amino acid sequence substantially identical to an amino acid sequence represented by SEQ ID No: 1, SEQ ID No: 2, SEQ ID No: 5 or SEQ ID No: 15 include an amino acid sequence having about 95% or more, preferably about 98% or more homology with an amino acid sequence represented by SEQ ID No: 1, SEQ ID No: 2, SEQ ID No: 5 or SEQ ID No: 15.

In particular, examples of the amino acid sequence substantially identical to an amino acid sequence represented by SEQ ID No: 1 include an amino acid sequence having 428th to 437th amino acids of an amino acid sequence represented by SEQ ID No: 1, examples of the amino acid sequence substantially identical to amino acid sequence represented by SEQ ID No: 2 include an amino acid sequence having 29th to 38th amino acids of an amino acid sequence represented by SEQ ID No: 2, and examples of the amino acid sequence substantially identical to an amino acid sequence represented by SEQ ID No: 15 include an amino acid sequence having 428th to 437th amino acids of an amino acid sequence represented by SEQ ID No: 15.

As a protein having the amino acid sequence substantially identical to an amino acid sequence represented by SEQ ID No: 1, SEQ ID No: 2, SEQ ID No: 5 or SEQ ID No: 15, for example, preferred is a protein having an amino acid sequence substantially identical to an amino acid sequence represented by SEQ ID No: 1, SEQ ID No: 2, SEQ ID No: 5 or SEQ ID No: 15 and having the activity substantially homogeneous to that of a protein having an amino acid sequence represented by SEQ ID No: 1, SEQ ID No: 2, SEQ ID No: 5 or SEQ ID No: 15.

In the present specification, "protease-like activity" means the activity of cutting (hydrolyzing) a peptide linkage and the like.

In the present invention, "extracellular matrix degrading enzyme activity" means the activity of an enzyme degrading the cell supporting tissue surrounding cells of tissues composed of collagen, elastin, proteoglycan, fibronectin, laminin and hyaluronic acid, in particular, the activity of an enzyme degrading proteoglycan (proteoglycan degrading enzyme activity).

Examples of the substantially homogeneous activity include the protease activity, and extracellular matrix degrading enzyme activity (preferably, proteoglycan degrading enzyme activity). "Substantially homogeneous" indicates that their activities are homogeneous in nature (for example, physiochemically or pharmacologically), therefore, equivalent (for example, about 0.1 to 100-fold, preferably about 0.5 to 10-fold, more preferably 0.5 to 2-fold) of the activity such as the protease activity and the extracellular matrix degrading enzyme activity (preferably, proteoglycan degrading enzyme activity) is preferable although quantitative elements such as degree of these activities and a molecular weight of a protein may be different.

Measurement of the protease activity can be performed according to the per se known method, and for example, can be measured according to a screening method described later.

A measurement of the extracellular matrix degrading enzyme activity using the proteoglycan degrading enzyme activity as an index can be performed, for example, according to a method described in Example 6 described later.

In addition, present protein includes so called mutein such as proteins comprising (a) an amino acid sequence in which 1 to 5 (preferably, 1 to 3) amino acids in an amino acid sequence represented by SEQ ID No: 1, SEQ ID No: 2, SEQ ID No: 5 or SEQ ID No: 15 are deleted, (b) an amino acid sequence in which 1 to 5 (preferably, 1 to 3) amino acids are added to an amino acid sequence represented by SEQ ID No: 1, SEQ ID No: 2, SEQ ID No: 5 or SEQ ID No: 15, (c) an amino acid sequence in which 1 to 5 (preferably 1 to 3) amino acids are inserted into an amino acid sequence represented by SEQ ID No: 1, SEQ ID No: 2, SEQ ID No: 5 or SEQ ID No: 15, (d) an amino acid sequence in which 1 to 5 (preferably 1 to 3) amino acids in an amino acid sequence represented by SEQ ID No: 1, SEQ ID No: 2, SEQ ID No: 5 or SEQ ID No: 15 are substituted with other amino acids, or (e) an amino acid sequence of a combination of them.

When insertion, deletion or substitution is made as described above in an amino acid sequence, the positions of the insertion, deletion or substitution are not particularly limited.

In addition, examples of positions of insertion, deletion or substitution include positions other than 119th Val to 495th Phe and positions other than 36th Thr to 350th Asp among an amino acid sequence represented by SEQ ID No: 1 or SEQ ID No: 15.

An amino acid sequence represented by SEQ ID No: 2 corresponds to an amino acid sequence of 400th (Leu) to 495th (Phe) of an amino acid sequence represented by SEQ ID No: 1 and an amino acid sequence represented by SEQ ID No: 5 corresponds to an amino acid sequence of 199th (Val) to 399th (Pro) of an amino acid sequence represented by SEQ ID No: 1.

In proteins in the present specification, a left end is a N-terminal (amino terminal) and a right end is a C-terminal (carboxyl terminal) according to the convention of the peptide display. Although present proteins including a protein comprising an amino acid sequence represented by SEQ ID No: 1, SEQ ID No: 2, SEQ ID No: 5 or SEQ ID No: 15 have usually carboxyl group (—COOH) or carboxylate (—COO⁻) as a C-terminal, they may be amide (—CONH$_2$) or ester (—COOR) as a C-terminal.

As R in ester, for example, $C_{1-6}$ alkyl group such as methyl, ethyl, n-propyl, isopropyl and n-butyl, $C_{3-8}$ cycloalkyl group such as cyclopentyl and cyclohexyl, $C_{6-12}$ aryl group such as phenyl and α-naphthyl, $C_{7-14}$ aralkyl group such as phenyl-$C_{1-2}$ alkyl group such as benzyl and phenetyl, and α-naphthyl-$C_{1-2}$ alkyl group such as α-naphthylmethyl, as well as pivaloyloxy group generally used in an oral ester are used.

When the present protein has carboxyl group (or carboxylate) at a position other than C-terminal, proteins in which carboxyl group is amidated or esterified are also included in the present protein. As an ester in this case, for examples, an ester at a C-terminal described above is used.

Further, present proteins also include proteins in which an amino group of a N-terminal amino acid residue (for example, methionine residue) is protected with a protecting group (for example, $C_{1-6}$ acyl group such as $C_{1-6}$ alkanoyl such as formyl group and acetyl group), proteins in which a N-terminal glutamine residue produced by cutting in the living body is pyroglutamine-oxidized, proteins in which a substituent (e.g., —OH, —SH, amino group, imidazole group, indole group, guanidino group) on a side chain of an intramolecular amino acid is protected with a suitable protecting group ($C_{1-6}$ acyl group such as $C_{1-6}$ alkanoyl group such as formyl group and acetyl group), and conjugated protein such as so called glycoprotein with a sugar chain bound.

Figure 1:
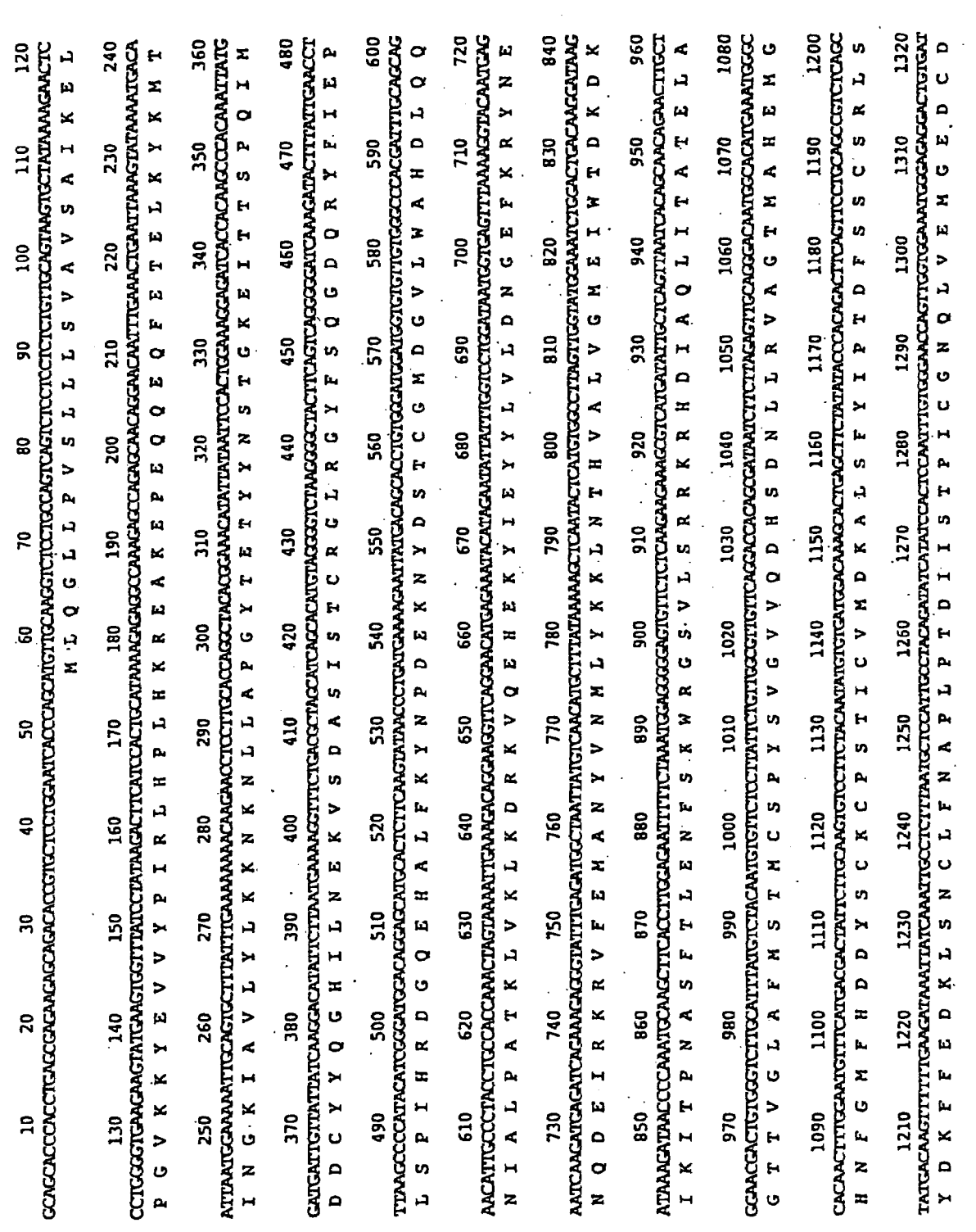

As an embodiment of the present protein, for example, a human-derived protein (FIG. 1 and FIG. 2 or FIG. 3 and FIG. 4) having an amino acid sequence represented by SEQ ID No: 1 or SEQ ID No: 15 is used.

As a partial peptide of the present protein, any partial peptides of the above-mentioned present protein may be used. Preferably, used are partial peptides having the similar activity such as the protease activity, and extracellular matrix degrading enzyme activity (preferably, proteoglycan degrading activity) to that of the above-mentioned present protein may be used. For example, peptides having at least 20% or more, preferably 50% or more, further preferably 70% or more, more preferably 90% or more, most preferably 95% or more of an amino acid sequence in a constituent amino acid sequence of the present protein and having the protease activity, the extracellular matrix degrading enzyme activity (preferably, the proteoglycan degrading enzyme activity) are used.

Among these peptides, for example, a peptide having an amino acid sequence having 28th to 37th amino acids (amino acid sequence represented by SEQ ID No: 8) of an amino acid sequence represented by SEQ ID No: 1 is used.

In addition, peptides having an amino acid sequence represented by SEQ ID No: 8 and SEQ ID No: 2 are suitable.

In addition, in the partial peptide of the present invention, 1 to 5 (preferably, 1 to 3) amino acids may be deleted in its amino acid sequence, or 1 to 5 (preferably, 1 to 3) amino acids may be added to its amino acid sequence, or 1 to 5 (preferably, 1 to 3) amino acids may be inserted into its amino acid sequence, or 1 to 5 (preferably, 1 to 3) amino acids may be substituted with other amino acids.

In addition, although the partial peptide of the present invention has usually carboxyl group (—COOH) or carboxylate (—COO⁻) as a C-terminal, the C-terminal may be amido (—CONH$_2$) or ester (—COOR) as the present protein described above.

Further, the partial peptide of the present invention includes a partial peptide in which an amino group of a N-terminal amino acid residue (e.g., methionine residue) is protected with a protecting group, a partial peptide in which a glutamine residue produced by cleavage of a N-terminal side in the living body is pyroglutamine-oxidized, a partial peptide in which a substituent on a side chain of an intramolecular amino acid is protected with a suitable protecting group, and a conjugated peptide such as so-called glycoprotein with a sugar chain bound.

Since the partial peptide of the present invention can be used as an antigen for producing an antibody, it necessarily needs to have the protease activity, or the extracellular matrix degrading enzyme activity (preferably, proteoglycan degrading enzyme activity).

As a salt of the protein or the partial peptide of the present invention, used are salts with physiologically acceptable acids (e.g., inorganic acids and organic acids) or bases (e.g., alkali metal salts). Preferred are physiologically acceptable acid addition salts. As such the salts, for example, salts with inorganic acids (e.g., hydrochloric acid, phosphoric acid, hydrobromic acid, sulfuric acid), or salts with organic acids (e.g., acetic acid, formic acid, propionic acid, fumaric acid, maleic acid, succinic acid, tartaric acid, citric acid, malic acid, oxalic acid, benzoic acid, methanesulfuric acid and benzenesulfuric acid) are used.

The present protein or a salt thereof can be prepared from cells or tissues of human being and a warm blood mammal described above by the per se known method of purifying proteins, or can be prepared by culturing a transformant comprising a DNA encoding a protein described later. Alternatively, it can be prepared according to a method of synthesizing a peptide described later.

When prepared from tissues or cells of human being or a mammal, tissues or cells of human being or a mammal are homogenized, extracted with an acid or the like, and the extract can be purified and isolated by combining chromatography such as reverse chromatography, ion exchange chromatography and the like.

For synthesizing a protein, a partial peptide or a salt thereof, of the present invention, or an amide thereof, a commercially available synthesizing resin can be usually used. Examples of such the resin include chloromethyl resin, hydroxymethyl resin, benzhydrylamine resin, aminomethyl resin, 4-benzyloxybenzylalcohol resin, 4-methylbenzhydrylamine resin, PAM resin, 4-hydroxymethylmethylphenylacetamidomethyl resin, polyacrylamide resin, 4-(2',4'-dimethoxyphenyl-hydroxymethyl)phenoxy resin, and 4-(2', 4'-dimethoxyphenyl -Fmoc aminoethyl)phenoxy resin. By using such resin, amino acids having an α-amino acid and a side chain functional group suitably protected are condensed on a resin like a sequence of an end protein according to various per se known condensing methods. At the end of the reaction, a protein is cleaved from a resin and at the same time various protecting groups are removed, and an intramolecular disulfide linkage forming reaction is further performed in a highly-diluted solution to obtain the end protein or an amide thereof.

As regards condensation of the above-mentioned protected amino acids, a variety activating reagents, which can be used for synthesizing proteins can be used and, in particular, carbodiimides are suitable. As carbodiimides, DCC, N',N'-diisopropylcarbodiimide and N-ethyl-N'-(3-dimethylaminoprolyl)carbodiimide are used. For activation by them, a protected amino acid is directly added together with a recemization-inhibiting agent (e.g., HOBt and HOOBt), or a protected amino acid is activated into a symmetrical acid anhydride or HOBt ester or HOOBt ester in advance, which may be thereafter added to a resin.

A solvent used for activating a protected amino acid or condensing with a resin can be appropriately selected from solvents, which are known to be used for a condensation of proteins. For example, used are acid amides such as N,N-dimethylformamide, N,N-dimethylacetamide and N-methylpyrrolidone, halogenated hydrocarbons such as methylene chloride and chloroform, alcohols such as trifluoroethanol, sulfoxides such as dimethylsulfoxide, pyridine, ethers such as dioxane and tetrahydrofuran, nitriles such as acetonitrile and propionitrile, esters such as methyl acetate and ethyl acetate or an appropriate mixture. A reaction temperature is appropriately selected from a range which can be used for a protein binding forming reaction and is usually appropriately selected from a range of about −20° C. to 50° C. An activated amino acid derivative is usually used in 1.5 to 4-fold excessive amount. When condensation is insufficient as a result of a test using a ninhydrin reaction, sufficient condensation can be performed by repeating a condensation reaction without leaving a protecting group. When insufficient condensation can be obtained by repeating a reaction even if a reaction is repeated, it is possible not to have the effects on the later reactions by acetylating an unreacted amino acid using acetic anhydride or acetylimidazole.

As a protecting group for a starting material amino acid, for example, Z, Boc, t-pentyloxycarbonyl, isobonyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosfinothioyl and Fmoc are used.

A carboxyl group can be protected, for example, by alkylesterification (straight-chain, branched or cyclic alkylesterification such as methyl, ethyl, propyl, butyl, t-butyl, cyclopentyl, cyclohexyl, cycloheptyl, cyclooctyl and 2-adamantyl), aralkylesterification (e.g., benzylesterification, 4-nitrobenzylesterification, 4-methoxybenzylesterification, 4-chlorobenzylesterification and benzhydrylesterification), phenacylesterification, benzyloxycarbonylhydrizidation, t-butoxycarbonylhydrazidation and tritylhydrzidation.

A hydroxyl group of serine can be protected, for example, by esterification or etherification. As a group suitable for this esterification, for example, lower ($C_{1-6}$)alkanoyl group such as acetyl group, aroyl group such as benzoyl group, and a group derived from carbonic acid such as benzyloxycarbonyl group and ethoxycarbonyl group are used. In addition, examples of a group suitable for etherification inculde benzyl group, tetrahydropyranyl group and t-butyl group.

As a protecting group for tyrosine, for example, Bzl, $Cl_2$—Bzl, 2-nitrobenzyl, Br-Z and t-butyl are used.

As a protecting group for imidazole of histidine, for example, Tos, 4-methoxy-2,3,6-trimethylbenzenesulfonyl, DNP, benzyloxymethyl, Bum, Boc, Tri and Fmoc are used.

As an activated carboxyl group of a starting material, for example, corresponding acid anhydride, azido, and active ester [ester with alcohol (e.g., pentachlorophenol, 2,4,5-trichlorophenol, 2,4-dinitrophenol, cyanomethyl alcohol, paranitrophenol, HONB, N-hydroxysuccinimide, N-hydroxyphthalimide, HOBt) are used. As an activated amino group of a starting material, for example, corresponding phosphoric amide is used.

As a method of removing (deprotecting) a protecting group, for example, catalytic reduction in a hydrogen stream in the presence of a catalyst such as Pd-black and Pd-carbon, acid treatment using anhydrous hydrogen fluoride, methanesulfuric acid, trifluoromethanesulfuric acid, trifluoroacetic acid or a mixed solution thereof, base treatment using diisopropylethylamine, triethylamine, piperidine and piperazine, and reduction using sodium in liquid ammonia are used. The deprotection by the above treatment using an acid is generally performed at a temperature of about $-20°$ C. to $40°$ C. In the acid treatment, it is advantageous to add a cation scavenger such as anisole, phenol, thioanisole, methacresol, paracresol, dimethyl sulfide, 1,4-butanediol and 1,2-ethanedithiol. In addition, a 2,4-dinitrophenyl group used as a protecting group for imidazole of histidine is removed by thiophenol treatment, and a formyl group is removed by used as a protecting group for indole of tryptophan is also removed by alkali treatment with a dilute sodium hydroxide solution and dilute ammonia in addition to deprotection with acid treatment in the presence of the above 1,2-ethanedithiol and 1,4-buthanedithiol.

Protection of functional groups of a starting material which should not be involved in a reaction and protecting groups therefor, as well as deprotection of the protecting groups, and activation of functional groups involved in a reaction can be appropriately selected from the known groups and the known means.

In another method of obtaining an amide of a protein, for example, an α-carboxyl group of a carboxyl-terminal amino acid is first amidated to protect it and, thereafter, a peptide (protein) chain is extended on an amino group side to the desired extent and, thereafter, a protein in which only protecting group for an amino group of a N-terminal of the peptide chain is removed and a protein in which only a protecting group for a carboxyl group of a C-terminal is removed are prepared, and both proteins are condensed in a mixed solvent described above. The details for a condensation reaction are as described above. After a protected protein obtained by condensation is purified, all protecting groups can be removed by the above-mentioned methods to obtain the crude desired protein. This crude protein can be purified by the known various purification means and main fractions can be lyophilized to obtain an amide of the desired protein.

For obtaining an ester of a protein, for example, after an α-carboxyl group of a carboxyl-terminal amino acid is condensed with the desired alcohols to obtain an amino acid ester, the desired ester of a protein can be obtained according to the same manner as that for an amide of a protein.

A partial peptide of the present invention or a salt thereof can be prepared according to the per se known peptide synthesizing method, or by cleaving the present protein with a suitable peptidase. A peptide synthesizing method may be according to any of a solid phase synthesizing method or a solution synthesizing method. That is, the end peptide can be prepared by condensing a partial peptide or amino acids which can constitute the present partial peptide with a remaining part and, when the product has a protecting group, deprotecting a protecting group. An example of the known condensing method and protection of a protection group are those methods described in the following (1)–(5):

(1) M. Bodanszky and M. A. Ondetti, Peptide Synthesis, Interscience Publishers, New York (1966);

(2) Schroeder and Luebke, The Peptide, Academic Press, New York (1965);

(3) Nobuo Izumiya at al., Fundaments and Experiment for Peptide Synthesis, Maruzen (K.K.) (1975);

(4) Haruaki Yajima and Shunpei Sakakibara, Biochemical Experimental Course 1, Protein Chemistry IV, 205, (1977); and (5) Haruaki Yajima (supervisor), Development of medicines, a second series, vol. 14, Peptide Synthesis, Hirokawashoten.

In addition, after the reaction, the present partial peptide can be purified and isolated by combining the conventional purifying methods such as solvent extraction, distillation, column chromatography, liquid chromatography and recrystallization. When the partial peptide obtained by the above method or a signal peptide is free, it can be converted into a suitable salt by the known method or analogous thereto and, conversely when obtained as a salt, it can be converted into a free form or another salt by the known method or analogous thereto.

A DNA encoding the present protein may be any DNAs as long as they comprise a base sequence encoding the above-mentioned present protein. In addition, they may be a genomic DNA, a genomic DNA library, cDNA derived from the above-mentioned cells and tissues, a cDNA library derived from the above-mentioned cells and tissues, or a synthetic DNA.

A vector used for a library may be any of bacteriophage, plasmid, cosmid and phargemide. In addition, amplification can be performed directly by Reverse Transcriptase Polymerase Chain Reaction (hereinafter abbreviated as RT-PCR method) using total RNA or mRNA fraction prepared from the above-mentioned cells or tissues.

As a DNA encoding the present protein, any DNAs may be used as long as they are, for example, (a) a DNA comprising a base sequence represented by SEQ ID No: 3, or a DNA having a base sequence which hybridizes with a base sequence represented by SEQ ID No: 3 under the highly stringent conditions and coding a protein having the activity substantially homogenous to that of the present protein (e.g., protease activity, extracellular matrix degrading enzyme activity (preferably, proteoglycan degrading enzyme activity)), (b) a DNA comprising a base sequence represented by SEQ ID No: 4, or a DNA having a base sequence which hybridizes with a base sequence represented by SEQ ID No: 4 under the highly stringent conditions and coding a protein having the activity substantially homogenous to that of the present protein (e.g., protease activity, extracellular matrix degrading enzyme activity (preferably, proteoglycan degrading enzyme activity)), (c) a DNA comprising a base sequence represented by SEQ ID No: 16, or a DNA having a base sequence which hybridizes with a base sequence represented by SEQ ID No: 16 under the highly stringent conditions and coding a protein having the activity substantially homogenous to that of the present protein (e.g., protease activity, extracellular matrix degrading enzyme activity (preferably, proteoglycan degrading enzyme activity)).

As a DNA which can hybridize with a base sequence represented by any SEQ ID No. of SEQ ID No: 3, SEQ ID No: 4 or SEQ ID No: 16, for example, a DNA having a base sequence having about 95% or more, preferably about 98% or more homology with a base sequence represented by any SEQ ID No. of SEQ ID No: 3, SEQ ID No: 4 or SEQ ID No: 16 is used.

Hybridization can be performed by the per se known method or analogous thereto, for example, a method described in Molecular Cloning 2nd (J. Sambrook et al., Cold Spring Harbor Lab., 1989). In addition, when a commercially available library is used, hybridization can be performed according to a method described in the attached specification. More preferably, hybridization can be performed according to the highly stringent conditions.

Highly stringent conditions denote, for example, the conditions of the sodium concentration of about 19 to 40 mM, preferably about 19 to 20 mM, and a temperature of about 50 to 70° C., preferably about 60 to 65° C. The conditions of the sodium concentration of about 19 mM and a temperature of about 65° C. are most preferable.

More particularly, as a DNA encoding a protein having an amino acid sequence represented by SEQ ID No: 1, for example, a DNA having a base sequence represented by SEQ ID No: 3 is used. As a DNA encoding a protein having an amino acid sequence represented by SEQ ID No: 2, for example, a DNA having a base sequence represented by SEQ ID No: 4 is used. And, as a DNA encoding a protein having an amino acid sequence represented by SEQ ID No: 15, for example, a DNA having a base sequence represented by SEQ ID No: 16 is used.

As a DNA encoding the present partial peptide, any DNAs are used as long as they comprise a base sequence encoding the present peptide described above. In addition, they may be a gemonic DNA, a gemonic DNA library, cDNA derived from the above-mentioned cells or tissues, a cDNA library derived from the above-mentioned cells or tissues, or a synthetic DNA.

As a DNA encoding the present partial peptide, for example, use are (a) a DNA having a partial base sequence of a DNA having a base sequence represented by SEQ ID No: 3, or a DNA having a base sequence which hybridizes with a base sequence represented by SEQ ID No: 3 under the highly stringent conditions and having a partial base sequence of a DNA encoding a protein having the activity substantially homogenous to that of the present protein, (b) a DNA having a partial base sequence of a DNA having a base sequence represented by SEQ ID No: 4, or a DNA having a base sequence which hybridizes with a base sequence represented by SEQ ID No: 4 under the highly stringent conditions and having a partial base sequence of a DNA encoding a protein having the activity substantially homogenous to that of the present protein, and (c) a DNA having a partial base sequence of a DNA having a base sequence represented by SEQ ID No: 16, or a DNA having a base sequence which hybridizes with a base sequence represented by SEQ ID No: 16 under the highly stringent conditions and having a partial base sequence of a DNA encoding a protein having the activity substantially homogenous to that of the present protein are used.

A DNA which can hybridize with a base represented by any SEQ ID No. of SEQ ID No: 3, SEQ ID No: 4 or SEQ ID No: 16 denotes the same meaning as that described above.

The same hybridization method and highly stringent conditions as those described above are used.

As a means for cloning a DNA completely encoding the present protein or partial peptide (hereinafter this protein and the like are simply abbreviated as present protein in the explanation of cloning and expression of DNAs encoding this protein and the like), a synthetic DNA library having a partial base sequence of the present protein is used and amplified by a PCR method, or a DNA incorporated into a suitable vector can be selected by using a DNA fragment or a synthetic DNA encoding a part or an all region of the present protein and hybridization with labeled ones. A hybridization method can be performed according to a method described in Molecular Cloning 2nd (J. Sambrook et al., Cold Spring Harbor Press, 1989). In addition, when a commercially available library is used, hybridization can be performed according to a method described in the attached specification.

Conversion of a base sequence of a DNA can be performed by using the known kit, for example, Mutant™-G (Takarashuzo (K.K.)) and Mutant™-K (Takarashuzo (K.K.)) according to the per se known method such as a Gupped duplex method or a Kunkel method, or analogous thereto.

A DNA encoding a cloned protein can be used as it is or, if desired, by digesting with a restriction enzyme or adding a linker thereto. The DNA may have ATG as a translation initiation codon at its 5'-terminal side or may have TAA, TGA or TAG as a translation termination codon at its 3'-terminal side. These translation initiation codon and translation termination codon may be added using a suitable synthetic DNA adaptor.

An expression vector for the present protein can be prepared, for example, by (a) excising the end DNA fragment from a DNA encoding the present protein, (b) ligating the DNA fragment to downstream of a promoter in a suitable expression vector.

As a vector, used are a plasmid derived from *Escherichia coli* (e.g., pBR322, pBR325, pUC12 and pUC13), a plasmid derived from *Bacillus subtilis* (e.g., pUB110, pTP5 and pC194), a plasmid derived from yeast (e.g., pSH19 and pSH15), a bacteriophage such as λ phage, an animal virus such as retrovirus, vacciniavirus and baculovirus, as well as pA1-11, pXT1, pRc/CMV, pRc/RSV, and pcDNAI/Neo.

As a promoter used in the present invention, any promoters may be used as long as they are suitable depending upon hosts used for expressing a gene. Examples of them are a SRα promoter, a SV40 promoter, a LTR promoter, a CMV promoter and a HSV-TK promoter when an animal cell is used as a host.

Among others, a CMV (cytomegalovirus) promoter and a SRα promoter are preferably used. When a host is an *Escherichia* microorganism, a trp promoter, a lac promoter, a recA promoter, a λPL promoter, a lpp promoter, a T7 promoter and so forth are preferable. When a host is a *Bacillus* microorganism, a SPO1 promoter, a SPO2 promoter, a penP promoter and so forth are preferable. When a host is yeast, a PHO5 promoter, PKG promoter, a GAP promoter, an ADH promoter and so forth are preferable. When a host is an insect cell, a polyhedron promoter, a P10 promoter and so forth are preferable.

Besides the above promoters, an expression promoter which optionally comprises an enhancer, a splicing signal, an polyA addition signal, a selectable marker and a SV40 origin (hereinafter abbreviated as SV40ori in some cases) can be used. Examples of the selectable marker include dihydrofolate reductase (hereinafter abbreviated as dhfr in some cases) gene [methotrexate (MTX) resistant], ampicillin resistant gene (hereinafter abbreviated as $Amp^r$ in some cases) and neomycin resistant gene (hereinafter abbreviated as $Neo^r$ in some cases, G418 resistant). In particular, when a dhfr gene-deficient Chinese hamster cell is used and a dhfr gene is used as a selectable marker, the end gene may be selected by a medium containing no thymidine.

In addition, if necessary, a signal sequence suitable for a host is added to a N-terminal side of the present protein. When a host is an *Escherichia* microorganism, a PhoA signal sequence, an OmpA signal sequence and so forth can be utilized. When a host is a *Bacillus* microorganism, an a amylase signal sequence, a subtilisin signal sequence and so forth can be utilized. When a host is yeast, a MFα signal sequence, a SUC2 signal sequence and so forth can be utilized. When a host is an animal cell, an insulin signal sequence, an α-interferon signal sequence, an antibody signal sequence and so forth can be utilized.

Thus constructed vector comprising a DNA encoding the present protein can be used to prepare a transformant.

As a host, for example, an *Escherichia* microorganism, a *Bacillus* microorganism, yeast, an insect cell, an insect and an animal cell are used.

As examples of the bacterium belonging to genus *Escherichia*, for example, *Escherichia coli* K12•DH1 [Proc. Natl. Acad. Sci. USA, vol. 60, 160 (1968)], JM103 [Nucleic Acids Research, vol. 9, 309 (1981)], JA221 [Journal of Molecular Biology, vol. 120, 517 (1978)], HB101 [Journal of Molecular Biology, vol. 41, 459 (1969)] and C600 [Genetics, vol. 39, 440 (1954)] are used.

As the bacterium belonging to genus *Bacillus*, for example, *Bacillus subtilis* MI114 [Gene, vol. 24, 255 (1983)] and 207–21 [Journal of Biochemistry, vol. 95, 87 (1984)] are used.

As the yeast, for example, *Saccharomyces cerevisiae* AH22, $AH22R^-$, NA87–11A, DKD-5D and 20B-12, *Schizosaccharomyces pombe* NCYC1913, NCYC2036, and *Pichia pastoris* KM71 are used.

As the insect cell, for example, when a virus is AcNPV, an established cell derived from a larva of Barathra (*Spodoptera frugiperda* cell; Sf cell), MG1 cell derived from a midgut of *Trichoplusia ni*, High Five™ cell derived from an egg of *Trichoplusia ni*, a cell derived from *Mamesira brassicae* and a cell derived from *Estigmena acrea* are used. When a virus is BmNPV, an established cell derived from a silkworm (*Bombyx mori* N cell; BmN cell) is used. As the Sf cell, for example, a Sf9 cell (ATCC CRL1711) and a Sf21 cell (the foregoing, Vaughn, J. L. et al., In Vivo, vol. 13, 213–217 (1977)) are used.

As the insect, for example, a larva of a silkworm is used [Maeda, et al., Nature, vol. 315, 592 (1985)].

As the animal cell, for example, a monkey cell COS-7 (COS7), Vero, a Chinese hamster cell CHO (hereinafter abbreviated as CHO cell), a dhfr gene-deficient Chinese hamster cell CHO (hereinafter abbreviated as CHO(dhfr$^-$) cell), a mouse L cell, a mouse AtT-20 cell, a mouse myeloma cell, rat GH3 and a human FL cell are used.

In order to transform an *Escherichia* microorganism, transformation can be performed according to a method described, for example, in Proc. Natl. Acad. Sci. USA, vol. 69, 2110 (1972) and Gene, vol. 17, 107 (1982)), and so forth.

In order to transform a *Bacillus* microorganism, transformation can be performed according to a method described, for example, in Molecular & General Genetics, vol. 168, 111 (1979)), and so forth.

In order to transform yeast, transformation can be performed according to a method described, for example, in Methods in Enzymology, vol. 194, 182–187 (1991), and Proc. Natl. Acad. Sci. USA, vol. 75, 1929 (1978), and so forth.

In order to transform an insect cell or an insect, transformation can be performed according to a method described, for example, in Bio/Technology, vol. 6, 47–55 (1988), and so forth.

In order to transform an animal cell, transformation can be performed according to a method described, for example, in Cell Technology, a separate volume 8, New Cell Technology Experimental Protocol, 263–267 (1995) (published by Shujunsha) and Virology, vol. 52, 456 (1973).

Thereby, a transformant transformed with an expression vector comprising a DNA encoding a protein can be obtained.

When a transformant for which a host is an *Escherichia* microorganism or *Bacillus*, a liquid medium is suitable as a medium used for culturing, and a carbon source, a nitrogen source, inorganic substances and others necessary for growth of a transformant are contained therein. Examples of the carbon source include glucose, dextrin, insoluble starch and sucrose, examples of the nitrogen sucrose include inorganic or organic substances such as ammonium salts, nitrates, corn steep liquor, peptone, casein, broth extract, soy bean cake and potato extract, and examples of inorganic substances include calcium chloride, sodium dihydrogen phosphate and magnesium chloride. In addition, yeast, vitamins and growth promoting factors may be added. PH of a medium is desirably about 5 to 8.

As a medium upon culturing of an *Escherichia* microorganism, for example, a M9 medium containing glucose and casamino acid [Miller, Journal of Experiments in Molecular Genetics, 431–433, Cold Spring Harbor Laboratory, New York 1972] is preferable. Here, in order to allow a promoter to work effectively, a medicine such as 3β-indolylacrylic acid can be added.

When a host is an *Escherichia* microorganism, culturing is usually performed at about 15 to 43° C. for about 3 to 24 hours and, if necessary, aeration and stirring may be added.

When a host is a *Bacillus* microorganism, culturing is usually performed at about 30 to 40° C. for about 6 to 24 hours and, if necessary, aeration and stirring may be added.

When a transformant for which a host is yeast is cultured, examples of a medium include a Burkholder minimum medium [Bostian, K. L. et al., Proc. Natl. Acad. Sci. USA, vol. 77, 4505 (1980)] and a SD medium containing 0.5% casamino acid [Bitter, G. A. et al., Proc. Natl. Acad. Sci. USA, vol. 81, 5330 (1984)]. PH of a medium is preferably adjusted to about 5 to 8. The culturing is usually performed at about 20° C. to 35° C. for about 24 to 72 hours and, if necessary, aeration and stirring are added.

When a transformant for which a host is an insect cell or an insect is cultured, examples of a medium include a Grace's Insect Medium (Grace, T. T. C., Nature, vol. 195, 788 (1962)], to which additives such as 10% immobilized bovine serum are appropriately added. PH of a medium is preferably adjusted to about 6.2 to 6.4. The culturing is usually performed at about 27° C. for about 3 to 5 days and, if necessary, aeration and stirring are added.

When a transformant for which a host is an animal cell is cultured, examples of a medium include, a MEM medium containing about 5 to 20% fetal bovine serum [Science, vol. 122, 501 (1952)], a DMEM medium [Virology, vol. 8, 396 (1959)], a RPMI 1964 medium [The Journal of the American Association, vol. 199, 519 (1967)], and a 199 medium [Proceedings of the Society for the Biological Medicine, vol. 72, 1 (1950)]. PH is preferably about 6 to 8. The culturing is usually performed at about 30° C. to 40° C. for about 15 to 60 hours and, if necessary, aeration and stirring are added.

As described above, the present protein can be produced in a membrane of a transformant.

In order to separate the present protein from the above culture and purify the protein, this can be performed, for example, by the following method.

When the present protein is extracted from the cultured bacterium or cells, appropriately used is a method of collecting the bacterium or cells by the known method after culturing, suspending them in a suitable buffer, destructing the bacterium or cells ultrasound, lysozyme and/or freezing melting, and obtaining the crude solution of a protein by centrifugation or filtration. A protein denaturing agent such as urea and guanidine chloride, and a surfactant such as Triton X-100™ may be contained in a buffer. When a protein is secreted in the culturing solution, after the culturing is complete, the bacterium or cells and the supernatant are separated by the per se known method and the supernatant is collected.

Purification of the thus obtained culture supernatant or a protein contained in the extract can be performed by appropriately combining the per se known separating and purifying methods. As these known separating and purifying methods, used are a method utilizing the solubility such as salting out and solvent precipitating method, a method utilizing a difference mainly in a molecular weight such as a dialysis method, an ultra filtration method, a gel filtration method, and a SDS-polyacrylamide gel electrophoresis method, a method utilizing difference in charge such as ion exchange chromatography, a method utilizing specific affinity such affinity chromatography, and a method utilizing a difference in an isoelectric point such as an isoelectric focusing method.

When the thus obtained protein is obtained as a free form, it can be converted into a salt by the per se known method or analogous thereto and, conversely when obtained as a salt, the salt can be converted into a free form or another salt.

In addition, a protein produced by a transformant can be arbitrarily modified or a polypeptide can be partially removed by acting a protein modifying enzyme before or after purification. Examples of the protein modifying enzyme include trypsin, chymotrypsin, arginylendopeptidase, proteinkinase and glycosidase.

The presence or the activity of the thus produced present protein or a salt thereof can be measured by a binding experiment with a labeled ligand and enzyme immunoassay using a specific antibody.

As an antibody against the present protein or partial peptide or a salt thereof, any antibodies may be used, whether polyclonal or monoclonal, as long as they can recognize the present protein or partial peptide or a salt thereof.

An antibody against the present protein, partial peptide or a salt thereof (hereinafter this protein and the like are simply abbreviated as present protein in the explanation of an antibody) can be prepared by using the present protein as an antigen according to the per se known method for producing an antibody or an anti-serum.

Preparation of a Monoclonal Antibody (a) Preparation of a Cell Producing a Monoclonal Antibody The present protein is administered to a warm blood animal at a site which can produce an antibody by an administration, as it is or together with a carrier and diluent. In order to enhance the antibody producing ability upon administration, complete Freund's adjuvant or incomplete Freund's adjuvant may be administered. Administration is usually performed once every 2 to 6 weeks at a total of around 2 to 10 times. Examples of a warm blood animal used include monkey, rabbit, dog, guinea pig, mouse, rat, sheep, gout and chicken. Preferably mouse and rat are used.

Upon preparation of a cell producing a monoclonal antibody, a hybridoma producing a monoclonal antibody can be prepared by selecting individuals for which the antibody titer is recognized from a warm blood animal immunized with an antigen, for example, mouse, taking a spleen or a lymph node 2 to 5 days after the final immunization, and fusing an antibody producing cell contained therein with a myeloma cell of homogeneous or heterogeneous animal. Measurement of the antibody titer in an anti-serum can be performed, for example, by measuring the activity of a label bound to an antibody after a reaction of a labeled protein described later and an anti-serum. Fusion procedures can be carried out by the known method, for example, a method of Khler and Milstin [Nature, 256, 495 (1975)]. Examples of a fusion promoting agent include polyethylene glycol (PEG) and Sendaivirus. Preferably, PEG is used.

Examples of myeloma cell include myeloma cells of a warm blood animal such as NS-1, P3U1, SP2/0 and AP-1. P3U1 is preferably used. A preferable ratio of the number of antibody producing cells (spleen cells) used and the number of myeloma cells is around 1:1 to 20:1. PEG (preferably, PEG 1000 to PEG 6000) is added at the concentration of around 10 to 80% and cell fusion is effectively performed by incubating at 20 to 40° C., preferably 30 to 37° C. for 1 to 10 minutes.

For screening a hybridoma producing a monoclonal antibody, a variety of methods can be used. Examples thereof include a method of adding a hybridoma culturing supernatant to a solid phase (e.g., microplate) onto which a protein antigen has been adsorbed directly or together with a carrier, adding an anti-immunoglobulin antibody (when a cell used for cell fusion is mouse, anti-mouse immunoglobulin antibody is used) labeled with a radioactive substance or an enzyme or protein A, and detecting a monoclonal antibody bound to a solid phase, and a method of adding a hybridoma culturing supernatant to a solid phase onto which an anti-immunoglobulin antibody or protein A has been adsorbed, and adding a protein labeled with a radioactive substance or an enzyme, and detecting a monoclonal antibody bound to a solid phase.

Selection of a monoclonal antibody can be performed according to the per se known method or analogous thereto. Usually, selection can be performed on a medium for an animal cell to which HAT (hypoxanthine, aminopterin, thymidine) has been added. As a medium for selection and growth, any media may be used as long as they can grow a hybridoma. For example, a RPMI 1640 medium containing 1 to 20%, preferably 10 to 20% fetal bovine serum, a GIT medium containing 1 to 10% fetal bovine serum (Wakojunyakukogyo (K.K.)) and a serum-free medium for culturing a hybridoma (SFM-101, Nissuiseiyaku (K.K.)) can be used. A culturing temperature is usually 20 to 40° C., preferably about 37° C. A culturing time is usually 5 days to 3 weeks, preferably 1 week to 2 weeks. Culturing can be usually performed under 5% carbonic acid gas. The antibody titer of a hybridoma culture supernatant can be measured according to the same manner as that for measurement of the antibody titer in an anti-serum mentioned above.

(b) Purification of a Monoclonal Antibody

Separation and purification of a monoclonal antibody can be performed according to the per se known method, for example, a method of separating and purifying a immunoglobulin [e.g., a salting out method, an alcohol precipitation method, an isoelectronic precipitation method, an electrophoresis method, an adsorbing and desorbing method with an ion exchanger (e.g., DEAE), an ultra centrifugation method, a gel filtration method, a specific purifying method of obtaining an antibody by taking only an antibody with an antigen binding solid phase or an active absorbing agent such as protein A or protein G, and dissociating a binding].

[Preparation of a Polyclonal Antibody]

A polyclonal antibody of the present invention can be prepared by the per se known method or analogous thereto. For example, the polyclonal antibody can be prepared by immunizing a warm blood animal with an immune antibody (protein antigen) itself or a complex of it and as in the method for preparing the above monoclonal antibody, taking a material containing an antibody against the present protein from the immunized animal, and separating and purifying the antibody.

Regarding a complex of an immune antigen and a carrier protein used for immunizing a warm blood animal, a kind of a carrier protein and a ratio of mixing a carrier and a hapten may be any ones as long as an antibody is effectively produced against a hapten immunized by cross-linking to a carrier. For example, a method of coupling bovine serum albumin, bovine thyroglobulin and hemocyanin with hapten at a ratio by weight of about 0.1 to 20, preferably about 1 to 5 relative to 1 of hapten.

In addition, a variety of condensing agents can be used for coupling a hapten and a carrier, and glutaraldehyde and carbodiimide, maleimide active ester, and active ester reagents containing a thiol group or a dithiopydityl group are used.

A fused product is administered to a warm blood animal at a site which can produce an antibody by an administration, as it is or together with a carrier and a diluent. In order to enhance the antibody producing ability upon administration, complete Freund's adjuvant or incomplete Freund's adjuvant may be administered. Administration is usually performed once every about 2 to 6 weeks at a total of around 3 to 10 times.

A polyclonal antibody can be taken out from blood and ascites, preferably blood of a warm blood animal immunized by the above-mentioned method.

The polyclonal antibody titer in an anti-serum can be measured according to the same manner as that for measurement of the antibody titer in an anti-serum mentioned above. Separation and purification of a polyclonal antibody can be performed according to a method of separating and purifying immunoglobulin as in separation and purification of the above monoclonal antibody.

As an antisense DNA having a base sequence complementary or substantially complementary to a DNA encoding the present protein or partial peptide (hereinafter these DNAs are abbreviated as present DNA in the explanation for an antisense DNA), any antisense DNA may be used as long as it has a base sequence complementary or substantially complementary to the present DNA and has the activity which can suppress expression of the DNA.

An example of a base sequence substantially complementary to the present DNA includes a base sequence having about 70% or more, preferably about 80% or more, more preferably about 90% or more, most preferably about 95% or more homology with an entire base sequence or partial base sequence of a base sequence complementary to the present DNA (that is, a complementary chain of the present DNA). In particular, preferred is an antisense DNA having about 70% or more, preferably about 80% or more, more preferably about 90% or more, most preferably about 95% or more homology with a complementary chain of a base sequence of a part encoding a N-terminal site (for example, a base sequence near an initiation codon) of the present protein, among an entire base sequence of a complementary chain of the present DNA. These antisense DNAs can be prepared using the known DNA synthesizing apparatus.

The uses of the present protein, partial peptide or a salt thereof (hereinafter abbreviated as present protein and the like in some cases), a DNA encoding the present protein or partial peptide (hereinafter abbreviated as present DNA in some cases), an antibody against the present protein, partial peptide or a salt thereof (hereinafter abbreviated as present antibody), and an antisense DNA are explained below.

(1) An Agent for Treating or Preventing Various Diseases that the Present Protein is Associated with Since the present protein contributes to degradation of an extracellular matrix (in particular, degradation of proteoglycan), when a DNA encoding the present protein is abnormal or deficient, there is a high possibility that a variety of diseases such as disc herniation, ischialgia, glomerular nephritis, diabetic nephropathy, hepatic fibrosis, pulmonary fibrosis and osteopetrosis develop.

Therefore, the present protein and the like and the present DNA can be used as a medicine such as an agent for treating or preventing a variety of diseases such as disc herniation, ischialgia, glomerular nephritis, diabetic nephropathy, hepatic fibrosis, pulmonary fibrosis and osteopetrosis.

For example, when a patient in which the present protein is decreased or deficient in the living body, a role of the present proteins and the like in the patient can be sufficiently or normally exerted by (a) administering the present DNA to the patient to express the present protein and the like in the living body, (b) inserting the present DNA in a cell to express the present protein and the like and, thereafter, transplanting the cell into the patient, or (c) administering the present protein and the like to the patient.

When the present DNA is used as the above-mentioned treating or preventing agent, the DNA can be administered to a human being or a warm blood animal alone or according to the conventional means after inserting into a suitable vector such as a retrovirus vector, an adenovirus vector, and an adenovirus associated virus vector. The present DNA can be administered as it is or by a gene gun or a catheter such as a hydro gel catheter by formulating together with a physiologically accepted carrier such as supplementary agent for promoting uptake.

When the present proteins and the like is used as the above-mentioned treating or preventing agent, that purified to at least 90%, preferably 95% or more, more preferably 98% or more, further preferably 99% or more is preferably used.

The present protein and the like can be used orally as a tablet which is coated with a sugar-coating if necessary, a capsulate, an elixir, or a microcapsulate, or can be used parenterally in the form of an injection such as a sterile solution or a suspension with water or other pharmaceutically acceptable solution. For example, the present protein and the like can be prepared by kneading with a physiologically acceptable carrier, a flavor, an excipient, a vehicle, a preservative, a stabilizer and a binding agent into a unit dosage form required for the generally recognized preparation implementation. An amount of an effective ingredient in these preparations is such that a suitable volume in an indicated range can be obtained.

As an additive which can be kneaded into a tablet or capsulate, for example, used are a binding agent such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, a flavor such as peppermint, akamono oil and cherry. When a compounding unit form is a capsule, the above type material may further contain a liquid carrier such as a fat or lipid. A sterile composition such as an injection can be formulated according to the conventional preparing protocol such as by dissolving or suspending an active substance, and a naturally occurring vegetable oil such as a sesame oil and a coconut oil in a vehicle such as injection water.

Examples of an aqueous solution for injection include a physiological saline and an isotonic solution containing glucose or other supplementary agent (e.g., D-sorbitol, D-mannitol and sodium chloride). The aqueous solution may be used with a suitable solubilizer such as an alcohol (e.g., ethanol), a polyalcohol (e.g., propylene glycol and polyethylene glycol), and a nonionic surfactant (e.g., Polysorbate 80™, and HCO-50). Examples of an oily solution include a sesame oil and a soybean oil. The oily solution may be used with a solubilizer such as benzyl benzoate and benzyl alcohol. In addition, a buffer (e.g., a phosphate buffer, and a sodium acetate buffer), a soothing agent (e.g., benzakonium chloride and procaine hydrochloride), a stabilizer (e.g., human-serum albumin and polyethylene glycol), a preservative (e.g., benzyl-alcohol and phenol), an antioxidant may be blended therein. The prepared injection solution is usually filled in a suitable ampoule.

A vector in which the present DNA is inserted is formulated as described above and is usually used parenterally.

Since the thus obtained preparation is safe and low toxicity, it can be administered, for example, to a human being or a warm blood animal (e.g., rat, mouse, guinea pig, rabbit, bird, sheep, cow, horse, cat, dog, monkey and chimpanzee.

An amount of the present protein and the like to be administered is different depending upon a subject disease, an administration subject, and a route of administration. For example, when the present protein and the like are administered orally for the purpose of treating diabetic nephropathy, the protein and the like are generally administered at an amount of about 0.1 mg to 100 mg, preferably about 1.0 to 50 mg, more preferably about 1.0 to 20 mg per day in an adult (60 kg). When administered parenterally, one time dose of the protein and the like is different depending upon an administration subject and an administration subject. For example, when the present protein and the like are administered to an adult (weight 60 kg) as a form of an injection for the purpose of treating diabetic nephropathy, the protein and the like are advantageously administered by injecting the protein and the like at around about 0.01 to 30 mg, preferably about 0.1 to 20 mg, more preferably about 0.1 to 10 mg per day. In the case of other animals, an amount calculated per 60 kg can be administered.

(2) Screening for a Medicine Candidate Compound for the Diseases

Since the present protein and the like have the protease activity and/or extracellular matrix (in particular, proteoglycan) degrading enzyme activity, a compound or a salt thereof which promotes the functions of the present protein and the like (e.g., protease activity, extracellular matrix degrading enzyme activity (preferably, proteoglycan degrading enzyme activity)) can be used as a medicine such as an agent for treating or preventing disc herniation, ischialgia, glomerular nephritis, diabetic nephropathy, hepatic fibrosis, pulmonary fibrosis and osteopetrosis.

On the other hand, a compound or a salt thereof which inhibits the functions of the present protein and the like can be used as a medicine such as an agent for treating or preventing rheumatoid arthritis, osteoarthritis, osteoporosis, arteriosclerosis and corneae ulcer (preferably, proteoglycan degrading enzyme activity).

Therefore, the present protein and the like are useful as a reagent for screening a compound or a salt thereof for promoting or inhibiting the functions of the present protein and the like.

That is, the present invention provides: (a) a compound or a salt thereof, which promotes the functions (e.g., the protease activity and the extracellular matrix degrading enzyme activity, (preferably, proteoglycan degrading enzyme activity)) of the present protein, partial peptide thereof or a salt thereof (hereinafter abbreviated as promoter in some cases), or a method for screening for a compound which inhibits the functions of the present protein, a partial peptide thereof or a salt thereof (hereinafter abbreviated as inhibitor in some cases), which comprises using the present protein, partial peptide thereof or a salt thereof.

More particularly, the present invention provides, for example, (b) a method for screening for a promoter or an inhibitor, which comprises comparing (i) the case where the present protein, partial peptide or a salt thereof is contacted with substrate, and (ii) the case where present protein, partial peptide thereof or a salt thereof is contacted with a substrate and a test compound.

More particularly, the above screening method comprises measuring, for example, the protease activity and the extracellular matrix degrading enzyme activity (preferably, the proteoglycan degrading enzyme activity) of the present protein and the like in the cases of (i) and (ii) and comparing them.

The protease activity of the present protein and the like can be measured according to the per se known method, for example, a method described in H. Nagase, Methods in Enzymology, vol. 248, 449–470 (1995) or analogous thereto (more particularly, a method described in later Example 4).

As the substrate, for example, a peptide (more particularly, MOCAc-Arg-Pro-Lys-Pro-Tyr-Ala-Nva-Trp-Met-Lys (DNP)-$NH_2$ described in later Example 4, manufactured by Peptide Laboratory) is used.

Examples of the test compound include a peptide, a protein, a non-peptide compound, a synthetic compound, a fermentation product, a cell extract, a vegetable extract and an animal tissue extract. These compounds may be novel compounds or the known compounds.

For carrying out the above screening method, an authentic product of the present protein and the like are prepared by suspending the present protein and the like in a buffer suitable for screening. Any buffers which do not inhibit a reaction of the present protein or the like and a substrate, such as a phosphate buffer and a Tris-hydrochloric acid buffer of pH about 4 to 10 (desirably pH about 6 to 8) may be used.

For example, a test compound which increases the protease activity in the above (ii) case by about 20% or more, preferably 30% or more, more preferably about 50% or more as compared with the above (i) case can be selected as a compound which promotes the protease activity of the present protein and the like and, on the other hand, a test compound which inhibits the protease activity and the like in the above (ii) case by about 20% ore more, preferably 30% or more, more preferably about 50% or more as compared with the above (i) case can be selected as a compound which inhibits the protease activity of the present protein and the like.

The extracellular matrix degrading enzyme activity (in particular, the proteoglycan degrading enzyme activity) of the present protein and the like can be measured by culturing of a mixture of a transformant comprising a DNA comprising a DNA having a base sequence encoding the present protein and a cartilage or a cartilage substrate producing cell derived from an animal, and measuring an amount of sulfated glycosaminoglycan in the culture supernatant. Examples of the transformant include the above-mentioned host for an expression vector, in which an expression vector comprising a DNA comprising a DNA having a base sequence encoding the present protein (for example, the above-mentioned expression vector and the like) is incorporated by the per se known method, and any transformants which produce the present protein and secretes it outside a bacterium (cell), or binds it with a cell membrane may be used. Among them, an animal cell, an insect cell and yeast are preferably used. In particular, animal cells and, Among them, COS7 cell is preferably used. Sulfated glycosaminoglycan in the culture supernatant can be measured by the per se known method, for example, a method described in Methods in Enzymology, vol. 248, pp. 47–58, 1995. Alternatively, it can be measured using a commercially available (Cosmobio) human aglecan (PG) ELISA kit and the like.

Examples of "an aminal" of the "cartilage or cartilage substrate producing cell derived from an animal" include warm blood animals (e.g., mouse, rat, rabbit, sheep, pig, cow, horse, bird, cat, dog, monkey and chimpanzee) and cow is preferable.

In addition, examples of a cartilage substrate producing cell include a cartilage cell and a cartilage sarcoma cell derived from an animal, as well as established cells such as HCS2/8 and ATDC5.

When an amount of sulfated glycosaminoglycan in the culture supernatant is large, it denotes that the extracellular matrix degrading enzyme activity (in particular, the proteoglycan degrading enzyme activity) is high. More particularly, as a method of measuring the extracellular matrix degrading enzyme activity, for example, there is a method described in later Example 6 and the like.

By using the above-mentioned method for measuring the extracellular matrix degrading enzyme activity (in particular, the proteoglycan degrading enzyme activity), for example, it becomes possible to detect a proteoglycan degrading enzyme gene by culturing a mixture of a transformant in which a test gene is introduced and a cartilage or a cartilage substrate producing cell derived from an animal, and measuring sulfated glycosaminoglycan in the culture supernatant.

As the "test gene", any test genes may be used as long as they are a gene encoding a peptide or a protein, which is produced by a transformant and secreted outside a bacterium (cell), or bound to a cell membrane. When a proteoglycan degrading enzyme is encoded by 2 or more genes, or when an activated enzyme of a proteoglycan degrading enzyme is necessary, "test gene" may be plural. In addition, if necessary, a signal sequence may be added to a N-terminal suitable for a host.

Further, (b) it is possible to screen an agent for inhibiting or promoting the proteoglycan degrading enzyme activity by culturing a mixture of a transformant in which a gene encoding a protein having the proteoglycan degrading enzyme activity is produced, and a cartilage or a cartilage substrate producing cell derived from an animal and a test, measuring sulfated glycosaminoglycan in the culture supernatant.

A preferable example of the "transformant in which a gene encoding a protein having the proteoglycan degrading enzyme activity is introduced" includes "an animal cell comprising a DNA comprising a DNA having a base sequence encoding the present protein", more preferably, "an animal cell comprising a DNA described in claim 5 or (ii) a DNA comprising a DNA having a base sequence encoding a protein comprising an amino acid sequence identical or substantially identical to an amino acid sequence represented by SEQ ID No: 5".

Examples of the "test compound" include a peptide, a protein, a non-peptide compound, a synthetic compound, a fermentation product, a cell extract, a plant extract and an animal tissue extract and these may be novel substances or the known substances.

When an amount of sulfated glycosaminoglycan in the culture supernatant is increased as compared with case where a test compound is not added, a test compound is considered to be an agent for promoting the proteoglycan degrading enzyme activity.

When an amount of sulfated glycosaminoglycan in the culture supernatant is decreased as compared with the case where a test compound is not added, a test compound is considered to be an agent for inhibiting the proteoglycan degrading enzyme activity.

In addition, a transformant, a cartilage or cartilage substrate producing cell derived from an animal and a test compound may be added simultaneously to culture a mixture, or a transformant and a test compound are mixed and a transformant is cultured in advance, and a cartilage or a cartilage substrate producing cell derived from an animal may be further added to culture a mixture. In the case of a cartilage substrate producing cell, it is preferably used after a cartilage substrate is produced. Alternatively, a cartilage or a cartilage substrate producing cell derived from an animal may be used by killing a cell by thermal treatment or freezing and melting.

A kit for screening of the present invention comprises the present protein, a precursor protein, partial peptide or a salt thereof. An example of the kit for screening of the present invention is as follows:

(3) Reagents for Screening (a) Buffer for Measurement 250 mM Tris-hydrochloric acid (pH7.5), 5 mM calcium chloride, 10 µM zinc chloride (b) Authentic Protein Present protein, partial peptide or a salt thereof (c) Substrate MOCAc-Arg-Pro-Lys-Pro-Tyr-Ala-Nva-Trp-Met-Lys (DNP)-NH$_2$ (d) Detecting Method Measurement of Fluorescent A compound or a salt thereof obtained by using a screening method or a screening kit of the present invention is a compound selected from the above test compounds, for example, a peptide, a protein, a non-peptide compound, a synthetic compound, a fermentation product, a cell extract, a plant extract, an animal tissue extract and plasma and is a compound which promotes or inhibits the functions (e.g., protease activity, extracellular matrix degrading enzyme activity (preferably, proteoglycan degrading enzyme activity)) of the present protein and the like.

As a salt of the compound, the same salt as that of the above-mentioned present protein is used.

A compound which promotes the functions (protease activity, extracellular matrix degrading enzyme activity (preferably, proteoglycan degrading enzyme activity)) of the present protein and the like can be used as a medicine such as an agent for treating or preventing diseases such as disc herniation, ischialgia, glomerular nephritis, diabetic nephropathy, hepatic fibrosis, pulmonary fibrosis or osteopetrosis.

On the other hand, a compound which inhibits the functions of the present protein and the like is useful as a medicine such as an agent for treating or preventing diseases such as rheumatoid arthritis, osteoarthritis, osteoporosis, cancer, arteriosclerosis or corneae ulcer.

When a compound obtained by using the present screening method or screening kit is used as the above-mentioned treating or preventing agent, the use can be carried out according to the conventional means. For example, the compound can be formulating into a tablet, a capsule, an elixir, a microcapsule, a sterile solution, and a suspension as in a medicine containing the above-mentioned present protein and the like.

Since the thus obtained preparation is safe and low toxic, it can be administered to a human being or a warm blood animal (e.g., mouse, rat, rabbit, sheep, pig, cow, horse, bird, cat, dog, monkey and chimpanzee).

A dose of the compound or a salt thereof is different depending upon its action, a subject disease, an administration subject and a route of administration. For example, when a compound which promotes the functions of the present protein and the like is orally administered for the purpose of treating diabetic nephropathy, the compound is generally administered to an adult (weight 60 kg) at an amount of about 0.1 to 100 mg, preferably about 0.1 to 50 mg, more preferably about 1.0 to 20 mg per day. When the compound is administered parenterally, an one time dose of the compound is different depending upon an administration subject and a subject disease. For example, when a compound which promotes the functions of the present protein and the like is generally administered to an adult (60 kg) in the form of an injection for the purpose of treating diabetic nephropathy, the compound is advantageously administered by an intravenous injection at an amount of around about 0.01 to 30 mg, preferably around about 0.1 to 20 mg, more preferably around about 0.1 to 10 mg per day. In the case of other animals, an amount calculated per 60 kg can be administered.

On the other hand, when a compound which inhibits the functions of the present protein and the like are orally administered for the purpose of treating a rheumatoid arthritis, the compound is generally administered to an adult (weight 60 kg) at an amount of about 0.1 to 100 mg, preferably about 1.0 to 50 mg, more preferably about 1.0 to 20 mg per day. When the compound is administered parenterally, a one time dose of the compound is different depending upon an administration subject and a subject disease. For example, when a compound which inhibits the functions of the present protein and the like is generally administered to an adult (60 kg) in the form of an injection for the purpose of treating rheumatoid arthritis, the compound is advantageously administered by an intravenous injection at an amount of around about 0.01 to 30 mg, preferably around about 0.1 to 20 mg, more preferably around about 0.1 to 10 mg per day. In the case of other animals, an amount calculated per 60 kg can be administered.

(3) Quantitation of the Present Protein, a Partial Peptide thereof or a Salt thereof Since an antibody against the present protein and the like (hereinafter abbreviated as present antibody in some cases) can specifically recognize the present protein and the like, it can be used for quantitating the present protein and the like in a test solution, in particular, quantitating by a sandwich immunological measuring method.

That is, the present invention provides:

(i) a method for quantitating the present protein and the like in a test solution, which comprises competitively reacting the present antibody with a test solution and the labeled present protein and the like, and determining a ratio of the labeled present protein and the like bound to the antibody, and (ii) a method for quantitating the present protein and the like in a test solution, which comprises simultaneously or successively reacting a test solution with the present antibody insolublized on a carrier and the labeled present another antibody, and determining the activity of a label on an insolublized carrier.

In the above (ii) quantitating method, it is desirable that one antibody is an antibody which recognizes a N-terminal of the present protein and the like and the other antibody is an antibody which reacts with a C-terminal of the present protein and the like.

Alternatively, a monoclonal antibody to present protein and the like (hereinafter referred to as present monoclonal antibody) can be used to quantitate the present protein and the like and, additionally, detection with tissue staining the like can be performed. For these purposes, an antibody molecule itself may be used and, alternatively, F(ab')$_2$, Fab' or Fab fraction of an antibody molecule may be used.

A method for quantitating the present protein and the like using the present antibody is not particularly limited but any measuring methods may be used as long as they are a method for measuring by detecting an amount of an antibody, an antigen or an antibody-antigen complex corresponding to an amount of an antigen in a test solution (for example, an amount of protein) by a chemical or physical means, and calculating this by a standard curve made using a standard solution containing the known amount of an antigen. For example, nephrometry, competition method, immunometric method and sandwich method are suitably used the use of a sandwich method described below is particularly preferable in sensitivity and specificity.

As a labeling agent used for a method of measuring using a labeling substance, for example, an radioisotope, an enzyme, a fluorescent substance and a chromogenic substance are used. As the radioisotope, for example, [$^{125}$I],

[$^{131}$I], [$^{3}$H] and [$^{14}$C] are used. As the above-mentioned enzyme, an enzyme which is safe and in large in specific activity is preferable. For example, β-galactosidase, β-glucosidase, alkaline phosphatase, peroxidase and malate dehydrogenase are used. As the fluorescent substance, for example, fluorescamine and fluorescein isothiocyanate are used. As the chromogenic substance, luminol, luminol derivative, luciferin and lucigenin are used. Further, a biotin-avidin system can be used for binding to a labeling agent with an antibody or an antigen.

Upon insolubilization of an antigen or an antibody, physical adsorption, or a method using a chemical bond usually used for insolubilizing or immobilizing a protein or an enzyme may be used. Examples of the carrier include insoluble polysaccharides such as agarose, dextran and cellulose, synthetic resins such as polystyrene, polyacrylamide and silicone, and glass and the like.

In a sandwich method, an amount of the present protein in a test solution can be quantitated by reacting a test solution with an insolubilized present monoclonal antibody (first reaction), further reacting a labeled other present monoclonal antibody (second reaction), and measuring the activity of a labeling agent on an insolubilized carrier. The first reaction and the second reaction can be performed in a reverse order, or performed simultaneously or at different times. A labeling agent and a method of insolubilization can be according to the above-mentioned ones. In addition, in an immunological method by a sandwich method, an antibody used for an antibody for a solid phase or an antibody for labeling is not necessarily one kind and a mixture of two or more kinds of antibodies may be used for improving the measuring sensitivity.

In a method of measuring the present protein and the like by the present sandwich method, as a monoclonal antibody used for the first reaction and the second reaction, an antibody having a different site to which the present protein and the like are bound is preferably used. That is, as an antibody used for the primary antibody and the second antibody, for example, when an antibody used in the second antibody recognizes a C-terminal of the present protein and the like, as an antibody used in the first reaction, an antibody which recognized a site other than a C-terminal, for example, a N-terminal is used.

The present monoclonal antibody can be used for measuring systems other than a sandwich method, for example, a competition method, an immonometric method or nephrometry.

In a competition method, after an antigen in a test solution and a labeled antigen are competitively, unreacted labeled antigen (F) and a labeled antigen (B) are separated (B/F separation), either of B and F is measured to quantitate an amount of an antigen in a test solution. A soluble antibody is used as an antibody in the present reaction, and a liquid phase method using polyethylene glycol, and the second antibody against the above antibody, or a solid phase method using a solid phased antibody as the primary antibody, or using a soluble antibody as the primary antibody and a solid phased antibody as the second antibody are used as B/F separation.

In the immunometric method, an antigen in a test solution and a solid phased antigen are competitively reacted with a constant amount of a labeled antibody and, thereafter, a solid phase and a liquid phase are separated, or an antigen in a test solution and an excessive amount of a labeled antibody are reacted and, then, a solid phased antigen is added to have unreacted antibody with a solid phase and, thereafter, a solid phase and a liquid phase are separated. Then, an amount of the label in either phase is measured to quantitate an amount of the antigen in a test solution.

In addition, an amount of an insolubilized precipitate produced as a result of a reaction of an antigen and an antibody in a gel or a solution in nephrometry. Even when an amount of an antigen in a test is small and only a small amount of a precipitate is obtained, a laser nephrometry using scattering of a laser is suitably used.

Upon application of these individual immunological measuring methods to a quantitating method of the present invention, setting of special conditions and procedures are not required. A system for measuring the present protein and the like may be constructed by adding technicians' consideration of a person skilled in the art to the normal conditions and procedures. For the detail for these general technical means, one can see reviews and books.

For example, one can see "Radioimmunoassay" supervised by Hiroshi Irie (Kodansha, published by in 1974), "Radioimmunoassay, a second series" supervised by Hiroshi Irie (Kodansha, published in 1979), "Immunoenzymometric method" (Igakushoin, published in 1978) supervised by Eiji Ishikawa (2nd ed.) (Igakushoin, published in 1982), "Immunoenzymometric method" supervised by Eiji Ishikawa (3rd ed.) (Igakushoin, published in 1987), and "Methods in ENZYMOLOGY" Vol. 70 (Immunometrical Techniques (Part A)), ibid. Vol. 73 (Immunometrical Techniques (Part B)), ibid. Vol. 74 (Immunochemical Techniques (Part C)), ibid. Vol. 84 (Immunochemical Techniques (Part D: Selected Immunoassay)), ibid. Vol. 92 (Immunochemical Techniques (Part E: Monoclonal Antibodies and General Immunoassay Methods)), and ibid. Vol. 121 (Immunochemical Techniques (Part 1: Hybridoma Technology and Monoclonal Antibodies)) (all published by Academic Press).

As described above, by using the present antibody, the present protein and the like can be measured with better sensitivity.

Further, by quantitating the concentration of the present protein and the like using the present antibody, (a) when a decrease in the concentration of the present protein and the like is detected, it can be for example determined that it is a disease such as disc herniation, ischialgia, glomerular nephritis, diabetic nephropathy, hepatic fibrosis, pulmonary fibrosis or osteopetrosis, or there is a high crisis for future development, and (b) when an increase in the concentration of the present protein and the like is detected, it can be determined that it is a disease such as rheumatoid arthritis, osteoarthritis, osteoporosis, cancer, arteriosclerosis or corneae ulcer, or a there is a high crisis for future development.

In addition, an antibody of the present invention can be used for detecting the present protein and the like present in a test such as a body liquid or a tissue. In addition, it can be used for preparing an antibody column used for purifying the present protein and the like, detection of the present protein and the like in each fraction in case of purifying, and analysis of the behavior of the present protein in a test cell.

(4) A Gene Diagnostic

Since the present DNA can detect the abnormality (gene abnormality) of a DNA or a mRNA encoding the present protein or a partial peptide thereof in a human being or a warm blood animal (e.g., rat, mouse, guinea pig, rabbit, bird, sheep, pig, cow, horse, cat, dog, monkey and chimpanzee) by using, for example, as a probe, it is useful, for example, as a gene diagnostic for damage, mutation or expression decrease of the DNA or mRNA, and increase or excess expression of the DNA or mRNA.

The above-mentioned gene diagnosis using the present DNA can be carried out, for example, according to the per se known northern hybridization and PCR-SSCP method (Genomics, vol. 5, pp. 874–879 (1989), Proceedings of the National Academy of Sciences of the United States of America, vol. 86, pp. 2766–2770 (1989)).

For example, when decrease in expression is detected by northern hybridization, it can be diagnosed as a high possibility of diseases such as disc herniation, ischialgia, glomerular nephritis, diabetic nephropathy, hepatic fibrosis, pulmonary fibrosis and osteopetrosis.

On the other hand, when excess expression is detected by northern hybridization, it can be diagnosed as a high possibility of diseases such as rheumatoid arthritis, osteoarthritis, osteoporosis, cancer, arteriosclerosis or corneae ulcer.

In addition, when a mutation in a DNA is detected by a PCR-SSCP method, it can be diagnoses of disc herniation, ischialgia, glomerular nephritis, diabetic nephropathy, hepatic fibrosis, pulmonary fibrosis or osteopetrosis, or diseases such as rheumatoid arthritis, osteoarthritis, osteoporosis, cancer, arteriosclerosis or corneae ulcer.

(5) Medicine Comprising an Antisense DNA

Since an antisense DNA which can bind to the present DNA complementarily and inhibit expression of the DNA can inhibit the functions of the present protein and the like or the present DNA in the living body, for example, it can be used as an agent for treating or preventing rheumatoid arthritis, osteoarthritis, osteoporosis, cancer, arteriosclerosis or corneae ulcer.

When the above antisense DNA is used as the above treating or preventing agent, the use can be carried out as in the above-mentioned agent for treating or preventing various diseases comprising the present DNA.

For example, when the antisense DNA is used, the antisense DNA can be carried out alone or after inserted into a suitable vector such as retrovirus vector, adenovirus vector or adenovirus-associated virus vector, according to the conventional means. The antisense DNA can be formulated into preparation as it is or together with a carrier which is physiologically recognized such as a supplementary agent in order to promote uptake, which can be administered by a gene gun or a catheter such as a hydrogel catheter.

Further, the antisense DNA may be used as a diagnostic oligonucleotide probe for examining the presence of the present DNA in tissues or cells or its expression situation.

(6) Medicine Comprising the Present Antibody

The present antibody having the activity of neutralizing the activity of the present protein and the like can be used, for example, as a medicine such as an treating or preventing a variety of diseases such as rheumatoid arthritis, osteoarthritis, osteoporosis, cancer, arteriosclerosis or corneae ulcer.

The above agent for treating or preventing diseases comprising the present antibody can be administered orally or parenterally as it is as a liquid preparation or as a pharmaceutical composition in the suitable dosage form, to a human being or a mammal (e.g., rat, rabbit, sheep, pig, cow, cat, dog and monkey). A dose is different depending upon an administration subject, a subject disease, symptom and an administration route and, for example, when administered for treating or preventing rheumatoid arthritis of an adult, it is advantageous to administer the present antibody by an intravenous injection at one time amount of usually around 0.01 to 20 mg/kg weight, preferably around 0.1 to 10 mg/kg weight, more preferably around 0.1 to 5 mg/kg weight around once to 5 times per day, preferably around once to 3 times per day. In the case of other parenteral and oral administration, the similar amount can be administered. When the symptom is severe, an amount may be increased depending upon the symptom.

The present antibody can be administered as it is or as a suitable pharmaceutical composition. The above pharmaceutical composition contains the above antibody or a salt thereof and a pharmacologically acceptable carrier, diluent or excipient. Such the composition is provided as a dosage form suitable for oral or parenteral administration.

That is, examples of a composition for oral administration include a solid or a liquid dosage form, more particularly, tablets (including sugar-coated tablets and film coating tablets), pills, granules, powders, capsules (including soft capsules), cyrups, emulsions and suspensions. Such the composition is prepared by the per se known method and contains a carrier, a diluent or an excipient which is usually used in the field of pharmaceutical preparation. For example, lactose, starch, sucrose and magnesium stearate are used as a carrier or an excipient for tablets.

As a composition for parenteral administration, for example, injections and suppositories are used and injections include dosage forms such as intravenous injections, subcutaneous injections, intradermal injections, intramuscular injections, drip injections. Such the injections are prepared according to the per se known method, by dissolving, suspending or emulsifying the above antibody or a salt thereof in a sterile aqueous or oily solution which is usually used for injections. As an aqueous solution for injection, for example, a physiologically saline and isotonic containing glucose and other supplementary medicines are used and suitable solublizer such as alcohols (e.g., ethanol), polyalcohols (e.g., propylene glycol and polyethylene glycol, nonionic surfactants [e.g., Polysorbate 80, HCO-50 (polyoxiethylene (50 mol) adduct of hydrogenated castor oil)] may be used therewith. As an oily solution, for example, a sesame oil and a soy bean oil are used. Benzyl benzoate and benzyl alcohol may be used therewith as a solublizer. The prepared injections are usually filled in a suitable ample. A suppository which is used for rectal administration can be prepared by mixing the above antibody or a salt thereof with a normal base for a suppository.

It is advantageous that the above-mentioned oral or parenteral pharmaceutical composition is prepared into the dosage unit form which is adapted to an amount of administration of an active ingredient. Examples of such the dosage unit form include tablets, pills, capsules, injections (ample) and suppositories and it is preferable that the above antibody is contained at an amount of normally 5 to 500 mg per each dosage unit form and, Among them, 5 to 100 mg for injections, 10 to 250 mg for other dosage forms.

The above-mentioned respective compositions may comprise other active ingredients as long as they do not produce not preferable interaction by blending with the above antibody.

(7) DNA-Transferred Animal

The present invention provides a non-human mammal having a DNA encoding foreign present protein and the like (hereinafter abbreviated as present foreign DNA) or its mutated DNA (abbreviated as present foreign mutated DNA in some cases).

That is, the present invention provides: (1) a non-human mammal having present foreign DNA or its mutated DNA; (2) the animal according to the (1) wherein the non-human mammal is a rodent; (3) the animal according to (2) wherein the rodent is a mouse or a rat; and (4) a recombinant vector which comprises the present foreign DNA or its mutated DNA and which can be expressed in a mammal.

A non-human mammal having present foreign DNA or its mutated DNA (hereinafter abbreviated as present DNA-transferred animal) can be made by transferring a DNA of interest in an unfertilized ovum, a fertilized ovum, a sperm and a germ cell including its primordial cell by a calcium phosphate method, an electric pulse, a lipofection method, an aggregation method, a microinjection method, a particle gun method or a DEAE-dextran method, preferably at an embryo development stage in development of a non-human mammal (more preferably, at a stage of a single cell or a fertilized ovum cell and generally before 8 cell phase). In addition, the present foreign DNA of interest is transferred into somatic cells, organs of the living body and tissue cells by the above DNA transferring method, which can be used for cell culturing and tissue culturing and, further, by fusing these cells with the above-mentioned germ cell by the per se known method of cell fusing, the present DNA-transferred animal can be made.

As a non-human mammal, for example, used are cow, pig, sheep, gout, rabbit, dog, cat, guinea pig, hamster, mouse and rat. Among others, a rodent which has a relatively short ontogeny and organism cycle and is easy in propagation, in particular, mouse (e.g., C57BL/6 line and DBA2 line as an inbred, B6C3F$_1$ line, BDF$_1$ line, B6D2F$_1$ line, BALD/c line and ICR line as a cross line) or a rat (e.g., Wistar and SD) is preferable from a view point of making a disease animal model.

As a "mammal" in a recombinant vector which can be expressed in a mammal, there is a human being in addition to the above-mentioned mammal.

The present foreign DNA does not refer to the present DNA originally harbored by a non-human mammal but refers to the present DNA isolated and extracted once from a mammal.

As the present mutated DNA, a mutated DNA in which a variation (for example, mutation) is produced in a base sequence of the original present DNA, more particularly, a DNA in which addition of a base, deletion of a base or substitution with other base is produced is used. In addition, an abnormal DNA is also included.

The abnormal DNA means a DNA which expresses the abnormal present protein and, for example, A DNA which expresses a protein inhibiting the functions of the normal present protein is used.

The present foreign DNA may be derived from a mammal which is homogeneous or heterogeneous to a subject animal. Upon transferring the present DNA to a subject animal, it is generally advantageous to use the DNA as a DNA construct bound to downstream of a promoter which can be expressed in an animal cell. For example, when the present human DNA is transferred, a DNA-transferred mammal which expresses highly the present DNA can be made by microinjecting into a fertilized ovum of a subject mammal, for example, mouse fertilized ovum a DNA construct (for example, vector) in which the present human DNA is bound to downstream of various promoters which can express a DNA derived from various mammal (e.g., rabbit, dog, cat, guinea pig, hamster, rat and mouse) having the present DNA having the high homology with the present human DNA.

As an expression vector for the present protein, an *Escherichia* microorganism-derived plasmid, a Bacillus microorganism-derived plasmid, a yeast-derived plasmid, a bacteriophage such as λ phage, retrovirus such as Moloneyleukemia virus and an animal virus such as bacciavirus and baculovirus are used. Among others, an *Escherichia* microorganism derived-plasmid, a *Bacillus* microorganism-derived plasmid and a yeast-derived plasmid are preferably used.

As a promoter which regulates expression of the above DNA, for example, (a) DNA promoters derived from viruses (e.g., simianvirus, cytomegalovirus, Moloneyleukemia virus, JC virus, breast cancer virus and poliovirus), (b) promoters derived from various mammal (human being, rabbit, dog, cat, guinea pig, hamster, rat and mouse), for example, promoters of albumin, insulin II, uroplaquine II, esterase, erythropoietin, endothelin, muscular creatine kinase, glia fibrous acid protein, glutathione S-transferase, platelet-derived growth factor β, keratine K1, K10 and K14, collagen I type and II type, cyclic AMP dependent protein kinase βI subunit, dystrophin, tartaric acid resistant alkaline phosphatase, atrial natriuretic factor, endothelial receptor tyrosinekinase (generally abbreviated as Tie2), sodium potassium adenosine 3 phosphoriation enzyme (Na, K-ATPase), neurofilament light chain, metallothionein I and IIA, metalloproteinase 1 tissue inhibitor, MHC class I antigen (H-2L), H-ras, renin, dopamine β-hydrorase, thyroid gland perooxidase (TPO), polypeptide chain elongation factor 1α (EF-1β), β actin, α and β myosin heavy chain, myosin light chain 1 and 2, myelin base protein, thyroglobulin, Thy-1, immunoglobulin, H chain varable part (VNP), serum amyloid P component, myoglobin, troponin C, smooth muscle α actin, preproenkephalin A and vasopressin are used. Among them, cytomegalovirus promoter, promoter of human polypeptide chain elongation factor 1α (EF-1β), and human and chicken β actin promoter are suitable which can be highly expressed in the whole body are suitable.

It is preferable that the above vector has a sequence which terminates transcription of a messenger RNA of interest (generally called as terminator) in a DNA trnscripting mammal and, for example, each DNA sequence derived from viruses and various mammal can be used and, preferably, simian virus SV40 terminator is used.

In order to have a foreign DNA of interest highly express, others such as a splicing signal, an enhancer region, and a part of eukaryotic DNA for such DNA can be ligated 5' upstream of a promoter region, between a promoter region and a translation region, or 3' downstream of a translation region depending upon the purposes.

A translation region of the normal present protein can be obtained as all or a part of a genomic DNA from DNAs derived from a liver cell, a kidney cell, a thyroid gland cell and a fibroblast cell derived from a human being and various mammal (e.g., rabbit, dog, cat, guinea pig, hamster, rat and mouse) and from commercially available genomic DNA libraries, or using, as a starting material, complementary DNAs prepared from RNAs derived from a liver cell, a kidney cell, a thyroid gland and a fibroblast cell by the known method. In addition, regarding the foreign abnormal DNAs, a translation region in which a translation region of a normal protein obtained from the above cells or tissues is mutated by a point mutagenesis method can be made.

The translation region can be made, as a DNA construct which can be expressed in a transferred animal, by the conventional DNA engineering procedures ligating to downstream of the above promoter and, if desired, upstream of a transcription terminator.

Transference of the present foreign DNA at a fertilized ovum cell stage can be secured to be present in a germ cell and all of somatic cells of a subject mammal. The presence of the present foreign DNA in a germ cell of a made animal after DNA transference means that all progenies of a made animal retain the present foreign DNA in its germ cell and all somatic cells. Progenies of this kind of animal inheriting the present foreign DNA have the present foreign DNA in its germ cell and all somatic cells.

A non-human mammal in which the present foreign normal DNA is transferred can secure stable maintenance of a foreign DNA by mating and, thus, can be subreared as an animal harboring the DNA under rearing environments.

Transference of the present foreign DNA at a fertilized cell stage is secured so as to be excessively present in a germ cell and all somatic cells of a subject mammal. The excess presence of the present foreign DNA in a germ cell of a made animal after DNA transference means that all progenies of a made animal have excessively the present foreign DNA in its germ cell and all somatic cells. Progenies of this kind of animal inheriting the present foreign DNA have excessively the present foreign DNA in its germ cell and all somatic cells.

Propagation passage can be performed so that all progenies have excessively the DNA by obtaining a homozygote animal having the introduced DNA in both homologous chromosomes and mating a male and a female of this animal.

In a non-human mammal having the present normal DNA, the normal DNA is highly expressed, hyperergasia of the present protein may be finally developed by promoting the functions of an endogenous normal DNA and such the non-human mammal can be utilized as a pathology model animal therefor. For example, pathological mechanism of hyperergasia of the present protein and diseases associated with the present protein can be elucidated and a method of treating these diseases can be studied.

In addition, since a mammal in which the present foreign normal DNA is transferred has the symptom of an increase in the freed present protein, it can be also utilized in a test of screening a medicine for treating diseases associated with the present protein.

On the other hand, a non-human mammal having the present foreign abnormal DNA can be subreared as an animal harboring the DNA under the normal rearing environments by securing stable maintenance of a foreign DNA by mating. Further, a foreign DNA of interest can be used as a starting material by incorporating into the above-mentioned plasmid. A DNA construct with a promoter can be made by the normal DNA engineering procedure. Transference of the present abnormal DNA at a fertilized cell stage can be secured so as to be present in a germ cell and all somatic cells in a subject mammal. The presence of the present abnormal DNA in a germ cell of a made animal after DNA transference means that all progenies of a made animal have the present abnormal DNA in its germ cell and all somatic cells. Progenies of this kind of animal inheriting the present foreign DNA have the present abnormal DNA in its germ cell and all somatic cells. Propagation passage can be performed, so that all progenies have the DNA, by obtaining a homozygote animal having the introduced DNA in both homologous chromosomes and mating a male and a female of this animal.

In a non-human mammal having the present abnormal DNA, the abnormal DNA is highly expressed, function inactive type refractory condition of the present protein may be finally developed by inhibiting the functions of an endogenous normal DNA and such the non-human mammal can be utilized as a pathology model animal therefor. For example, pathological mechanism of function inactive type refractory condition of the present protein can be elucidated and a method of treating these diseases can be studied.

In addition, as a specific utilization, the present abnormal DNA highly expressing animal can serve as a model for elucidating inhibition of the function of a normal protein by the present abnormal protein (dominant negative action) in function inactive type refractory condition of the present protein.

In addition, since a mammal in which the present foreign abnormal DNA is transferred has the symptom of an increase in the freed present protein, it can be also utilized in a test of screening a medicine for treating function inactive type refractory condition of the present protein.

In addition, as other utilization of the above two kinds of present DNA transferred animal, for example, the following can be contemplated: (a) use as a cell source for tissue culturing; (b) analysis of the relationship with a protein which is specifically expressed or activated by the present invention, by directly analyzing a DNA or a RNA in the tissues of the present DNA transferred animal or analyzing the protein tissue expressed by a DNA; (c) study of the function of a cell from the tissue which is generally difficult to be cultured, by culturing the tissue having a DNA by the standard tissue culturing techniques and using it; (d) screening of a medicine which enhances the function of a cell by using the cell described in the above (c); and (e) isolation and purification of the present mutated protein and preparation of an antibody thereto.

Further, the clinical symptom of diseases associated with the present protein including function inactive type refractory condition of the present protein can be examined and, in addition, the more detailed pathological observation in each organ of a disease model associated with the present protein can be obtained, which can make a contribution to development of a new treating method and, further, study and treatment of the secondary disease due to the above diseases.

In addition, freed DNA transferred cells can be obtained by a protease such as trypsin after each organ is taken out from the present DNA transferred animal and sectioned. And, its culture or its cultured cell can be systematized. Further, specification of a cell producing the present protein, the relationship with apoptosis, differentiation or proliferation, or the signal transmission mechanism in them can be examined, and their abnormality can be examined and, thus, it serves as an effective study material for elucidating the present protein and its action.

Further, there can be provided an effective and rapid method for screening for a agent for treating the diseases associated with the present protein using the above-mentioned examination method and quantitation method, in order to develop a agent for treating the above diseases including the function inactive type refractory of the present protein using the present DNA transferred animal. In addition, a DNA treating method of diseases associated with the present protein can be studied and developed using the present DNA transferred animal or the present foreign DNA expression vector.

(7) Knockout Animal

The present invention provides a non-human mammal embryo stem cell in which the present DNA with inactivated and a non-human mammal in which the present DNA is insufficiently expressed.

That is, the present invention provides: (1) a non-human mammal embryo stem cell in which the present DNA is inactivated; (2) the embryo stem cell according to the (1), in which the DNA is inactivated by introducing a reporter gene (e.g., β-glactosidase gene derived from *Escherichia coli*); (3) the embryo stem cell according to the (1), which is neomysin resistant; (4) the embryo stem cell according to the (1), wherein the non-human mammal is a rodent; (5) the embryo stem cell according to the (4), wherein the rodent is a mouse; (6) a non-human mammal insufficiently expressing the present DNA in which the DNA is inactivated; (7) the non-human mammal according to the (6), wherein the DNA is inactivated by introducing a reporter gene (e.g., β-glactosidase gene derived from *Escherichia coli*) and the reporter gene can be expressed under control of a promoter for the present DNA; (8) the non-human mammal according to the (6), wherein the non-human mammal is a rodent; (9) the non-human mammal according to the (8), wherein a rodent is a mouse; (10) a method for screening for a compound which promotes or inhibits the activity of a promoter for the present DNA or a salt thereof, which comprises administering a test compound to an animal according to the (7), and detecting expression of a reporter gene.

A non-human mammal embryo stem cell in which the present DNA is inactivated refers to an embryo stem cell (hereinafter abbreviated as ES cell) of a non-human mammal in which a DNA has substantially no ability of expressing the present protein (hereinafter referred to as present knockout DNA in some cases) by adding artificially a mutation to the present DNA harbored by the non-human mammal, to inhibit expression of the DNA or to substantially lose the activity of the present protein encoded by the DNA.

The same non-human mammal as that described above is used.

A method of artificially adding a mutation to the present DNA can be performed, for example, by deleting a part or all of the DNA sequence or inserting or substituting with other DNA by a genetic engineering procedure. The present knockout DNA may be prepared, for example, by shifting a leading frame of a codon, or destructing the function of a promoter or an exon by these mutations.

An embodiment of a non-human mammal embryo stem cell in which the present DNA is inactivated (hereinafter abbreviated as present DNA inactivated ES cell or present knockout ES cell) can be obtained, for example, by introducing, into a chromosome of a non-human mammal of interest by, for example, a homologous recombination method, a DNA chain having a DNA sequence constructed so as to destruct a gene consequently (hereinafter abbreviated as targeting vector) by isolating the present DNA harbored by the animal, and inserting a medicine resistant gene, a representative of which is a neomycin resistant gene or a hygromycin resistant gene, or a reporter gene, a representative of which is lacZ (β-glactosidase gene) or cat (chloramphenicol acetyltransferase gene) into its exon part, or by inserting a DNA sequence terminating transcription of a gene (e.g., polyA addition signal) into an intron part between exons, to make it impossible to synthesize a complete messenger RNA, and analyzing the resulting ES cell by Southern hybridization analysis using as a probe a DNA sequence on the present DNA or in its vicinity or a PCR method using as a primer a DNA sequence on the targeting vector and a DNA sequence in a vicinity region other than the present DNA used for preparing the targeting vector and, whereby, the present knockout ES cell is selected.

As the original ES cell for which the present DNA is inactivated by a homologous method, for example, the already established ES cell may be used as described above, or ES cell newly established according to the known Evans and Kaufma method may be used. For example, in the case of ES cell of a mouse, currently, ES cell of 129 line is generally used. However, since the cell has no clear immunological background, in order to obtain inbred ES cell having immunologically clear genetic background instead of 129 line ES cell, for example, ES cell established by using $BDF_1$ mouse in which a small number of taken eggs of C57BL/6 mouse or C57BL/6 was improved by crossing with DBA/2 ($F_1$ of C57BL/6 and DBA/2) may be used well. Since $BDF_1$ mouse has the background of C57BL/6 mouse in addition to advantages such as a large number of taken eggs and healthy eggs, ES cell obtained by using this can be usefully used in its genetic background can be substituted with that of C57BL/6 mouse by back crossing with C57BL/6 mouse when a pathologic model mouse is made.

In addition, when ES cell is established, blastocyst 3.5 days after fertilization is generally used and, besides, a number of initial embryos can be effectively obtained by taking eight cell embryo and culturing to blastocyst for use.

In addition, though either of female or male ES cell may be used, male ES cell is usually advantageous to make a germ line chimera. In addition, in order to decrease labor for complicated culture, it is desirable to perform determination of female and male as soon as possible. One example of a method for determining female and male of ES cell is a method for amplifying and detecting a gene of a sex determining region on Y chromosome by a PCR method. Since the use of this method needs only around 1 colony ES cell number (about 50) while about 106 cell number was previously required for karyotype analysis and, therefore, the first selection of ES cell at the initial culturing can be performed by determination of female and male and labor at the initial culturing can be remarkably decreased by the possibility of selection of a male cell at the early stage.

In addition, the secondary selection can be performed by confirmation of the number of chromosomes by G-banding. The number of chromosomes of the resulting ES cell is desirably 100% of the normal number. However, when it is difficult from the relationship of physical procedures upon establishment, it is desirable that, after a gene of ES cell is knocked out, it is cloned again into a normal cell (e.g., a cell having the number of chromosomes of 2n=40 in mouse).

Since the thus obtained embryo stem cell strain has usually the better glowing properties but tends to lose the ability of ontogeny, it is necessary to carefully subculture it. For example, it is cultured by a method of culturing at about 37° C. on a suitable feeder cell such as STO fibroblast in a carbonic acid gas incubator (preferably, 5% carbonic acid gas, 95% air or 5% oxygen, 5% carbonic gas, 90% air) in the presence of LIF (1–10000 U/ml) and, upon passage, for example, a method is taken of making it into a single cell by treatment with trypsin/EDTA solution (usually 0.001–0.5% trypsin/0.1–5 mM EDTA, preferably 0.1% trypsin/1 mM EDTA) and seeding it on a newly prepared feeder cell. Such the passage is usually performed every 1 to 3 days and it is desired that a cell is observed upon this and, when morphologically abnormal cell is seen, the culture cell is discarded.

ES cell can be differentiated into a variety of types of cells such as long muscle of head, viscous muscle and cardiac muscle by monolayer culturing to high density under the suitable conditions or suspension culturing to formation of cell aggregation [M. J. Evans and M. H. Kaufman, Nature, vol. 292, p. 154, 1981; G. R. Martin Proc. Natl. Acad. Sci. U.S.A., vol. 78, p. 7634, 1981; T. C. Doetschman et al., Journal of Embryology and Experimental Morphology, vol. 87, p. 27, 1985], and the present DNA expression insufficient cell obtained by differentiating the present ES cell is useful for cell biology study of the present protein in vitro.

The present DNA expression insufficient non-human mammal can be discriminated from a normal animal by using an amount of mRNA of the animal using the known method to indirectly compare its expression amount.

As the non-human mammal, the same one as that described above is used.

The present DNA expression insufficient non-human mammal can knock out the present DNA by introducing the targeting vector prepared as described above into a mouse embryo stem cell or a mouse egg cell, and homologously recombining the present DNA on a chromosome of a mouse embryo stem cell or a mouse egg cell with a DNA sequence in which of the present DNA of the targeting vector is inactivated by the introduction, to substitute with each other.

A cell in which the present DNA is knocked out can be determined by Southern hybridization using a DNA on the present DNA or in the vicinity of it as a probe, or by a PCR method using a DNA sequence on the targeting vector and a DNA in the vicinity other than the present DNA derived from a mouse used for the targeting vector as a primer. When the non-human mammal embryo stem cell is used, a cell strain in which the present DNA is inactivated is cloned, and thus obtained cell is introduced into a non-human mammal embryo or a blastocyst at a suitable time, for example, 8 cell phase, and then the made chimera embryo is transplanted of an uterus of a false pregnant non-human mammal. The made animal is a chimera animal composed of a cell having a normal present DNA locus and an artificially mutated present DNA locus.

When a part of a germ cell of the chimera animal has a mutated present DNA locus, an individual in which all tissues are composed of a cell having a present DNA locus to which an artificial mutation has been added can be obtained from an individual group obtained by mating such the chimera individual and a normal individual, for example, by selecting by a coat color determination method. The thus obtained individual is usually a present protein heteroexpression insufficient individual, and can be obtained by mating present protein heteroexpression insufficient individuals mutually and, from the children, a present protein homoexpression insufficient individual can be obtained.

When an egg cell is used, for example, transgenic non-human mammals in which a targeting vector is introduced in a chromosome can be obtained by injecting a DNA solution into a nucleus of an egg cell by a microinjection method, and they can be obtained by selecting a mammal having a mutation in the present DNA locus as compared with these transgenic non-human mammal by a gene homologous recombination.

An individual in which the present DNA is knocked out in this way can be passage-reared by the normal rearing environment by confirming that an animal individual obtained by mating has also the DNA knocked out.

Further, the obtaining and retaining of a germ line may be carried out according to the conventional method. That is, by mating a female and a male of an animal harboring the inactivated DNA, a homozygote animal having the inactivated DNA in both homologous chromosomes can be obtained. The homozygote animal can be effectively obtained by rearing in the state where a normal individual is 1 and a homozygote is a plural relative to a mother animal. By mating a female and a male of a heterozygote animal, a homozygote and a heterozygote animals having the inactivated DNA are propagation-passaged.

A non-human mammal embryo stem cell in which the present DNA is inactivated is very useful for making the present DNA expression insufficient non-human animal.

In addition, since the present DNA expression insufficient non-human animal lacks a variety of bioactivities which can be derived by the present protein and, therefore, it can serve as a model for diseases caused by inactivation of the bioactivity of the present protein, it is useful for research of causes of and study of a treating method these diseases.

(7a) A Method for Screening for a Compound Having the Treating or Preventing Effects to Diseases Caused by Deficiency or Damage of the Present DNA The present DNA expression insufficient non-human mammal can be used for screening for a compound having the treating or preventing effects to diseases caused by deficiency or damage of the present DNA (e.g., disc herniation, ischialgia, glomerular nephritis, diabetic nephropathy, hepatic fibrosis, pulmonary fibrosis or osteopetrosis).

That is, the present invention provides a method for screening for a compound having the treating or preventing effects to diseases caused by deficiency or damage of the present DNA or a salt thereof, which comprises administering a test compound to the present DNA expression insufficient non-human mammal and observing and measuring a change in the animal.

As the present DNA expression insufficient non-human mammal used in the screening method, the same mammal as that described above is used.

Examples of the test compound include a peptide, a protein, a non-peptide compound, a synthetic compound, a fermentation product, a cell extract, a plant extract, an animal tissue extract and plasma and these compounds may be a novel compound or the known compound.

More particularly, comparing the present DNA expression insufficient non-human mammal treated with a test compound with control mammal and using a change in each organ, tissue and symptom of diseases of the mammal as an index can test the treating or preventing effects of a test compound.

As a method for treating a test animal with a test compound, for example, oral administration and intravenous injection are used and can be appropriately selected depending upon the sympton of the test animal and the nature of the test compound. In addition, an amount of a test compound to be administered can be appropriately selected depending upon an administration method and a nature of the test compound.

For example, when a compound having the treating or preventing effect to disc herniation, ischialgia, glomerular nephritis, diabetic nephropathy, hepatic fibrosis, pulmonary fibrosis or osteopetrosis is screened, the present DNA expression insufficient non-human mammal is treated with sugar-loading, a test compound is administered before or after sugar-loading treatment, and a blood sugar value and a change in weight of the animal are measured with time.

In the screening method, when a test compound is administered to a test animal, where a blood sugar value of the test animal is decreased about 10% or more, preferably about 30% or more, more preferably about 50% or more, the test compound can be selected as a compound having the treating or preventing effect to disc herniation, ischialgia, glomerular nephritis, diabetic nephropathy, hepatic fibrosis, pulmonary fibrosis or osteopetrosis.

Since a compound obtained by using the present screening method is a compound selected from the above test compounds and has the treating or preventing effect to diseases caused by deficiency or damage of the present protein and the like (e.g., disc herniation, ischialgia, glomerular nephritis, diabetic nephropathy, hepatic fibrosis, pulmonary fibrosis or osteopetrosis), it can be as a medicine such as a safe and low-toxic treating or preventing agent for the diseases. Further, compounds derived from the compounds obtained by the above screening can be used similarly.

The compounds obtained by the screening method may form a salt. As a salt of the compound, salts with physiologically acceptable salts (e.g., inorganic acids and organic acids) or bases (e.g., alkali metal) are used. Among them, physiologically acceptable acid addition salts are preferable. As such the salt, for example, salts with inorganic acids (e.g., hydrochloric acid, phosphoric acid, hydrobromic acid and sulfuric acid), or salts with organic acids (e.g., acetic acid, formic acid, propionic acid, fumaric acid, maleic acid, succinic acid, tartaric acid, malic acid, oxalic acid, benzoic acid, methane sulfuric acid and benzene sulfuric acid) are used.

A medicine comprising a compound obtained by the screening method or a salt thereof can be prepared as in the medicine comprising the present protein mentioned above.

Since preparations thus obtained are safe and low toxic, they can be administered, for example, to a human being or a mammal (e.g., rat, mouse, guinea pig, rabbit, sheep, pig, cow, horse, cat, dog and monkey). An amount of the compound or a salt thereof is different depending upon a subject disease, an administration subject and an administration route and, for example, when the compound is orally administered for the purpose of treatment, the compound is generally administered to an adult (weight 60 kg) at an amount of about 0.1 to 100 mg, preferably about 1.0 to 50 mg, more preferable about 1.0 to 20 mg per day. When the compound is administered parenterally, an one time dose of the compound is different depending upon an administration subject and a subject disease and, for example, the compound is generally administered to an adult (60 kg) in the form of an injection for the purpose of treating diabetic nephropathy, it is advantageous to administer the compound by intravenous injection at an amount of around about 0.01 to 30 mg, preferably around about 0.1 to 20 mg, more preferably around about 0.1 to 10 mg per day in the case of other animals, an amount calculated per 60 kg can be administered.

(7b) A Method for Screening for a Compound Which Promotes or Inhibits the Activity of a Promoter for Present DNA The present invention provides a method for screening for a compound which promotes or inhibits the activity of a promoter for the present DNA or a salt thereof, which comprises administering a test compound to the present DNA expression insufficient non-human mammal, and detecting expression of a reporter gene.

In the above screening method, as the present DNA expression insufficient non-human mammal, among the above-mentioned present DNA expression insufficient non-human mammal, a mammal in which the present DNA is inactivated by introduction of a reporter gene and the reporter gene can be expressed under control of a promoter for the present DNA.

As the test compound, there is the same compound as that described above.

As the reporter gene, the same gene as that described above is used. β-Galactosidase gene (lacZ), soluble alkaline phosphatase gene or luciferase gene is suitable.

In the present DNA expression insufficient non-human mammal in which the present DNA is substituted with a reporter gene, since the reporter gene is present under control of a promoter for the present DNA, the activity of a promoter can be detected by tracing expression of a substance encoded by the reporter gene.

For example, when a part of a DNA region encoding the present protein is substituted with β-galactosidase gene (lacZ) derived from *Escherichia coli*, β-galactosidase is expressed in stead of the present protein in a tissue in which the present protein is originally expressed. Therefore, for example, by staining using a reagent which is a substrate for β-galactosidase such as 5-bromo-4-chloro-3-indolyl-β-ga-lactopyranoside (X-gal), the expression state of the present protein in the living body of an animal can be simply observed. More particularly, by fixing the present protein deficient mouse or its tissue section with glutaraldehyde, washing with a phosphate-buffered physiological saline (PBS), reacting with a staining solution containing X-gal at room temperature or near 37° C. for about 30 minutes to 1 hour, and washing the tissue test with 1 mM EDTA/PBS solution, the β-galactosidase reaction is stopped and coloration may be observed. In addition, according to the conventional method, a mRNA encoding lacZ may be detected.

The compound obtained by using the above screening method or a salt thereof is a compound selected from the above test compounds and is a compound which promotes or inhibits the activity of a promoter for the present DNA.

The compounds obtained by the screening method may form a salt. As a salt of the compound, salts with physiologically acceptable acids (e.g., inorganic acids) or bases (e.g., organic acids) are used. Among them, physiologically acceptable acid addition salts are preferable. As such salt, for example, salts with inorganic acids (e.g., hydrochloric acid, phosphoric acid, hydrobromic acid and sulfuric acid), or salts with organic acids (e.g., acetic acid, formic acid, propionic acid, fumaric acid, maleic acid, succinic acid, tartaric acid, citric acid, malic acid, oxalic acid, benzoic acid, methane sulfuric acid and benzene sulfuric acid) are used.

Since a compound which promotes the activity of a promoter for the present DNA or a salt thereof can promotes expression of the present protein and promotes the functions the protein, for example, it is useful as a medicine such as a safe and low toxic treating or preventing agent for diseases such as disc herniation, ischialgia, glomerular nephritis, diabetic nephropathy, hepatic fibrosis, pulmonary fibrosis or osteopetrosis.

On the other hand, since a compound which inhibits the activity of a promoter for the present DNA or a salt thereof can inhibit expression of the present protein and inhibit the functions of the protein, it is useful as a medicine such as a safe and low toxic treating or preventing agent for diseases such as rheumatoid arthritis, osteoarthritis, osteoporosis, cancer, arteriosclerosis or corneae ulcer.

Further, compounds derived from the compounds obtained by the above screening can be used similarly.

A medicine comprising the compound obtained by the screening method or a salt thereof can be prepared as in the medicine comprising the present protein or a salt thereof mentioned above.

Since the preparations thus obtained are safe and low toxic, they can be administered to a human being or a mammal (e.g., rat, mouse, guinea pig, rabbit, sheep, pig, cow, horse, cat, dog and monkey).

An amount of the compound or a salt thereof is different depending upon a subject disease, an administration subject and an administration route and, for example, when a compound which promotes the activity of a promoter for the present DNA is orally administered for the purpose of treating diabetic nephropathy, the compound is generally administered to an adult (weight 60 kg) at an amount of about 0.1 to 100 mg, preferably about 1.0 to 50 mg, more preferably about 1.0 to 20 mg per day. When parenterally administered, an one time dose of the compound is different depending upon administration subject and a subject disease and, for example, a compound which promote the activity of a promoter for a present DNA is generally administered to an adult (60 kg) in the form of an injection for the purpose of treating diabetic nephropathy, it is advantageous to administer the compound by intravenous injection at an amount of around about 0.01 to 30 mg, preferably around about 0.1 to 20 mg, more preferably around about 0.1 to 10 mg per day. In the case of other animals, an amount calculated per 60 kg can be administered.

On the other hand, for example, when a compound which inhibits the activity of a promoter for the present DNA is orally administered for the purpose of treating rheumatoid arthritis, the compound is generally administered to an adult (weight 60 kg) at an amount of 0.1 to 100 mg, preferably about 1.0 to 50 mg, more preferably about 1.0 to 20 mg per day. When parenterally administered, an one time dose of the compound is different depending upon an administration subject and subject disease and, for example, a compound which inhibits the activity of a promoter for the present DNA is generally administered to an adult (60 kg) in the form of an injection for the purpose of treating rheumatoid arthritis, it is advantageous to administer the compound by intravenous injection at an amount of around about 0.01 to 30 mg, preferably around about 0.1 to 20 mg, more preferably around about 0.1 to 10 mg per day. In the case of other animals, an amount calculated per 60 kg can be administered.

Like this, the present DNA expression insufficient non-human mammal is extremely useful for screening for a compound which promotes or inhibits the activity of a promoter for the present DNA or a salt thereof and can make a great contribution to elucidation of causes of various diseases derived from the present DNA expression insufficiency and development of a preventing or treating agent.

In addition, a so called transgenic animal (gene-transferred animal) is made by using a DNA comprising a promoter region for the present protein is used, ligating a gene encoding a variety of proteins to downstream of it, and pouring it into an egg cell of an animal, it becomes possible to synthesize the protein specifically and study its action in the living body. Further, when a suitable reporter gene is bound to the above promoter part and a cell strain expressing this is established, it can be used as a searching system for low-molecular compounds which has the activity of specifically promoting or inhibiting the ability to produce the present protein itself in the living body.

When bases and amino acids are represented by abbreviation in the present specification and drawings, it is based on abbreviation according to IUPAC-IUB Commision on Biochemical Nomenclature or the conventional abbreviation in the art and, examples thereof are described below. In addition, when an optical isomer may be present regarding an amino acid, it denotes L-compound unless otherwise indicated.

DNA: deoxyribonucleic acid
cDNA: complementary deoxyribonucleic acid
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediamine tetraacetate
SDS: sodium dodecyl sulfate

TABLE 1

Common nucleotide symbols

| | |
|---|---|
| A: adenine | M: adenine (A) or cytosine(C) |
| T: thymine | K: guanine (G) or thymine (T) |
| G: guanine | S: guanine (G) or cytosine(C) |
| C: cytosine | W: adenine (A) or thymine (T) |
| I: inosine | B: guanine (G), guanine (G) or thymine (T) |
| R: adenine (A) or guanine (G) | D: adenine (A), guanine (G) or thymine (T) |
| Y: thymine (T) or cytosine(C) | V: adenine (A), guanine (G) or cytosine(C) |

TABLE 2

Common amino acid symbols

| | |
|---|---|
| Gly: glycine | Asp: aspartic acid |
| Ala: alanine | Lys: lysine |
| Val: valine | Arg: arginine |
| Leu: leucine | His: histidine |
| Ile: isoleucine | Phe: phenylalanine |
| Ser: serine | Tyr: tyrosine |
| Thr: threonine | Trp: tryptophan |
| Cys: cysteine | Pro: proline |
| Met: methionine | Asn: asparagine |
| Glu: glutamic acid | Gln: glutamine |
| | pGlu: pyroglutamic acid |

In addition, substituents, protecting groups and reagents which are frequently used in the present specification are expressed by the following symbols.

| | |
|---|---|
| Me: methyl group | Br-Z: 2-bromobenzyloxycarbonyl |
| Et: ethyl group | Boc: t-butoxycarbonyl |
| Bu: butyl group | DNP: dinitrophenyl |
| Ph: phenyl group | Trt: trityl |
| TC: thiazolydine-4(R)-carboxamido group | Bum: t-butoxymethyl |
| | Fmoc: N-9-fluorenylmethoxycarbonyl |
| Tos: p-toluene sulfonyl | HOBt: 1-hydroxybenztriazole |
| CHO: formyl | HOOBt: 3,4-dihydro-3-hydroxy-4-oxo-1,2,3-benztriazine |
| Bzl: benzyl | |
| Cl$_2$Bzl: 2,6-dichlorobenzyl | HONB: 1-hydroxy-5-norbornene-2,3-dicarboxyimide |
| Bom: benzyloxymethyl | |
| Z: benzyloxycarbonyl | DCC: N,N'-dicyclohexylcarbodiimide |
| Cl-Z: 2-chlorobenzyloxycarbonyl | MOCAc: (7-methoxycoumarin-4-yl) acetyl |
| | Nva: norvaline |
| | Nma: N-methylanthranilic acid |

The sequence numbers of Sequence Listing of the present specification denote the following sequences.

[SEQ ID No: 1] shows an amino acid sequence of a novel ADAM protein obtained in Example 1.

[SEQ ID No: 2] shows an amino acid sequence of a part corresponding to a disintegrin region of a protein represented by an amino acid sequence represented by SEQ ID No: 1 or SEQ ID No: 15. This corresponds to an amino acid sequence of 400th to 495th of an amino acid sequence represented by SEQ ID No: 1.

[SEQ ID No: 3] shows a base sequence of a DNA encoding the present protein having an amino acid represented by SEQ ID No: 1.

[SEQ ID No: 4] shows a base sequence of a DNA encoding a peptide having an amino acid sequence represented by SEQ ID No: 2.

[SEQ ID No: 5] shows an amino acid sequence of a part corresponding to a metalloprotease region of a protein represented by an amino acid sequence represented by SEQ ID No: 1 or SEQ ID No: 15. This corresponds to an amino acid sequence of 199th to 399th of an amino acid sequence represented by SEQ ID No: 1.

[SEQ ID No: 6] shows an amino acid sequence of a partial peptide of the present protein. This corresponds to an amino acid sequence of 428th to 437th of an amino acid sequence represented by SEQ ID No: 1 or SEQ ID No: 15.

[SEQ ID No: 7] shows a base sequence of a primer used in Example 1.

[SEQ ID No: 8] shows a base sequence of a primer used in Example 1.

[SEQ ID No: 9] shows a base sequence of a primer used in Example 1.

[SEQ ID No: 10] shows a base sequence of a primer used in Example 1.

[SEQ ID No: 11] shows a base sequence of a primer used in Example 1.

[SEQ ID No: 12] shows a base sequence of a primer used in Example 1.

[SEQ ID No: 13] shows a base sequence of a primer used in Example 1.

[SEQ ID No: 14] shows a base sequence of a primer used in Example 1.

[SEQ ID No: 15] shows an amino acid sequence of a novel ADAM protein obtained in Example 1.

[SEQ ID No: 16] shows a base sequence of a DNA encoding the present protein having an amino acid sequence represented by SEQ ID No: 15.

[SEQ ID No: 17] shows a base sequence of a primer used in Example 2.

[SEQ ID No: 18] shows a base sequence of a primer used in Example 2.

[SEQ ID No: 19] shows a base sequence of a primer used in Example 5.

[SEQ ID No: 20] shows a base sequence of a primer used in Example 5.

[SEQ ID No: 21] shows a base sequence of a primer used in Example 7.

[SEQ ID No: 22] shows a base sequence of a primer used in Example 7.

[SEQ ID No: 23] shows a base sequence of a primer used in Example 8.

[SEQ ID No: 24] shows a base sequence of a primer used in Example 8.

[SEQ ID No: 25] shows a base sequence of a primer used in Example 9.

[SEQ ID No: 26] shows a base sequence of a primer used in Example 9.

[SEQ ID No: 27] shows a base sequence of a primer used in Example 11.

[SEQ ID No: 28] shows a base sequence of a primer used in Example 11.

The transformant *Escherichia coli* DH5α/pTB2052 obtained in Example 1 below has been deposited at National Institute of Bioscience and Human-Technology (NIBH), Agency of Industrial Science & Technology, Ministry of International Trade & Industry as Accession Number of FERM BP-6474 since Aug. 26, 1998, and at Institute for Fermentation, Osaka, Japan (IFO) as Accession Number of IFO 16173 since May 20, 1998.

The transformant *Escherichia coli* DH5α/pTB2053 obtained in Example 1 below has been deposited at National Institute of Bioscience and Human-Technology (NIBH), Agency of Industrial Science & Technology, Ministry of International Trade & Industry as Accession Number of FERM BP-6475 since Aug. 26, 1998, and at Institute for Fermentation, Osaka, Japan (IFO) as Accession Number of IFO 16174 since May 20, 1998.

The transformant *Escherichia coli* JM109/pTB2076 transformed with the vector pTB2076 obtained in Example 9 below has been deposited at National Institute of Bioscience and Human-Technology (NIBH), Agency of Industrial Science & Technology, Ministry of International Trade & Industry as Accession Number of FERM BP-6857 since Aug. 23, 1999, and at Institute for Fermentation, Osaka, Japan (IFO) as Accession Number of IFO 16305 since Aug. 4, 1999.

The following Examples illustrate the present invention in more detail but the present invention is not limited to them. The genetic procedures using *Escherichia coli* were according to a method described in Molecular cloning.

EXAMPLE 1

Cloning of a Gene Encoding a Novel ADAM Protein

Using primers: [GT(A/G)GAI(C/G)(A/C)(A/G/T)(G/T)(C/G)(A/G/T)GA(A/G)(C/G) A(A/G)TGTGA (SEQ ID No: 7), and [A(C/T)(C/T)TG(A/T)(A/G/T)(C/G/T)(A/G)(A/G/T) (A/G/T)(A/T)IC(A/G/T)(G/T)(A/C/G)(A/G/T)(A/G/T)(C/G)IGGGCA (SEQ ID No. 8)] designed based on a region preserved in an ADAM family, degenerate PCR was carried out using a variety of human cDNAs as a template (40 times of 20 seconds at 95° C., 10 seconds at 40° C., and 1 minute at 72° C.).

A base sequence of the resulting amplified DNA fragment was sequenced and, as a result, a sequence showing the high homology with Atrolysin which is hemorrhagic venom was found. In order to a full length of this gene, a RACE (rapid amplification of cDNA ends) method was used as follows.

First, primers were designed based on the sequence found above and, using these primers [ATC ACA GTC CTC TCC CAT TTC CAC CAA C (SEQ ID No: 9)] and [CAC ATT TCA GGC AGG TCG CAC TCA TC (SEQ ID No: 10)] and Primers AP1 and AP2 attached to Marathon cDNA Amplification Kit manufactured by CLONTECH Company, a PCR was performed using Marathon ready cDNA (manufactured by CLONTECH Company) as a template according to a protocol attached to the Kit to try cloning of a 5' upstream fragment. Since a fragment containing a translation initiation codon could not be obtained, cloning of a 5' upstream fragment was carried out according to the same manner as that as described above using primers [TCG CTG TGG TCC TGA ACA ACG CCA ACA (SEQ ID No: 11)] and [CAC ACC ATC CAT CCC ACA GGT GCT GTC A (SEQ ID No: 12)] designed based on a sequence of the resulting fragment. The resulting PCR fragment contained a sequence which seemed to be a translation initiation codon.

On the other hand, in order to clone a 3' downstream fragment, primers [GGA ACC AGT TGG TGG AAA TGG GAG AGG A (SEQ ID No: 13)] and [AGG ACT GTG ATT GTG GGA CGT CTG AGG AA (SEQ ID No: 14)] were designed and a PCR was carried out according to the same manner as that described above. As a result, two kinds of sequences showing an entirely different sequences from on the way part in a protein encoding region were obtained.

pTB2052 and pTB2053 were obtained by ligating gene fragments obtained by the above RACE method, and inserting the ligated fragment into the expression vector pcDNA3.1 (manufactured by Invitrogen).

pTB2052 had a base sequence (containing 2325 bases shown by SEQ ID No: 16) shown in FIG. 3 and FIG. 4. A new ADAM protein composed of 775 amino acids shown by FIG. 3 and FIG. 4 (SEQ ID No: 15) is encoded in this cDNA fragment, and a signal sequence, a pro region, a metalloprotease region, a disintegrin region, a cysteine rich region, a transmembrane region and an intracellular region were recognized. pTB2052 was introduced into *Escherichia coli* DH5α according to the known method to obtain *Escherichia coli* DH5α/pTB2052.

On the other hand, pTB2053 had a base sequence (containing 1620 bases shown by SEQ ID No: 3) shown by FIG. 1 and FIG. 2. A new ADAM protein composed of 540 amino acids shown by SEQ ID No: 1 is encoded in this cDNA fragment, and a signal sequence, a pro sequence, a metalloprotease region, a disintegrin region, and a part of a cysteine rich region were recognized. pTB2053 was introduced into *Escherichia coli* DH5α by the known method to obtain *Escherichia coli* DH5α/pTB2053.

EXAMPLE 2

Construction of *Escherichia coli* Expression Vector

A metalloprotease region and a disintegrin region of the present ADAM protein were expressed in *Escherichia coli*. That is, a PCR reaction (20 seconds at 95° C., 10 seconds at 55° C., 2 minutes at 72° C., 25 times) was performed using pTB2053 obtained in Example 1 as a template and two kinds of primers [CAT ATG GTT CAG GAA CAT GAG AAA TAC ATA (SEQ ID No: 17)] and [CTC GAG GAA GCC ATT GAC TTG GAA TCT ATC (SEQ ID No: 18)] according to a protocol manufactured by Pfu turbo (manufactured by STRATAGENE). The PCR reaction solution was subjected to 1% agarose electrophoresis, and a band of around 900 bp was recovered and purified using QIAquick Gel Extraction Kit (manufactured by QIAGEN). This was inserted into the pCR-Blunt vector (manufactured by INVITROGEN) to transform *Escherichia coli* DH5α. A plasmid was extracted from this *Escherichia coli*, cut with Nde I and Xho I, ligated with pET21a (manufactured by NOVAGEN) which had been treated similarly, and *Escherichia coli* DH5α was transformed. Then, a plasmid (pMDH) was extracted from this transformant, and no error of a sequence was confirmed.

EXAMPLE 3

Expression of Recombinant ADAM Protein in *Escherichia coli* and Purification of the Same

*Escherichia coli* BL21 (DE3) was transformed with the plasmid pMDH obtained in Example 2 which was used for expression. Expression induction was conducted with 1 mM isopropylthiogalactopyranoside and purification was carried out according to the attached manual using Ni-NTA Agarose (manufactured by QIAGEN). As a result, about 35 kDa recombinant ADAM protein of interest was eluted with buffer E (A handbook for high-level expression and purification of 6× His-tagged proteins, QIAGEN). Then, the eluted material was dialyzed against a buffer [0.2M Tris-hydrochloric acid (pH 9.0), 3 mM 2-mercaptoethanol, 0.3 mM 2-hydroxyethyldisulfide, 2M urea, and 0.1% Triton X-100] at 4° C. for 3 hours using a dialysis membrane (manufactured by SPECTRUM MEDICAL) of a fractional molecular weight of 6,000 to 8,000 and, thereafter, dialyzed against a buffer [0.2 M Tris-hydrochloric acid (pH8.5), 3 mM 2-mercaptoethanol, 0.3 mM 2-hydroxyethyldisulfide, 0.5 M urea, 0.1% Triton X-100] for 2 hours, against a buffer [50 mM Tris-hydrochloric acid (pH8.0), 1 mM 2-mercaptoethanol, 0.1 mM 2-hydroxyethyldisulfide, 0.1 M urea, 0.05% Triton X-100, 150 mM sodium chloride] for 3 hours, and against a buffer [50 mM Tris-hydrochloric acid (pH7.5), 0.05% Triton X-100, and 150 mM sodium chloride] for 16 hours. Like this, 3.9 mg of the recombinant ADAM protein was obtained from 500 mL of culture supernatants.

EXAMPLE 4

Detection of the Protease Activity of a Recombinant of ADAM Protein

30 μL of a buffer [250 mM Tris-hydrochloric acid (pH7.5), 5 mM calcium chloride, and 10 μM zinc chloride] and 20 μL of the recombinant ADAM protein (0.8 mg/mL) obtained in Example 3 were added to a 96-well plate (Fluoro B plate, manufactured by Dainihonseiyaku). After preincuvation at 37° C. for 10 minutes, an enzymatic reaction was initiated by adding 100 μL of a 10 μM substrate [MOCAc-Arg-Pro-Lys-Pro-Tyr-Ala-Nva-Trp -Met-Lys(DNP)-NH$_2$, manufactured by Peptide Laboratory]. After the reaction at 37° C. for 22 hour, the fluorescent intensity in the reaction solution was measured at an excitation wave length of 328 nm and absorption wave length of 393 nm using a microplatereader (manufactured by Applied Biosystems). The fluorescent intensity was 2 when no recombinant ADAM protein was added, while the fluorescent intensity of 70 was shown when the protein was added. From these, it was made clear that the present ADAM protein had the protease activity. It is considered that search of a substance which regulates (inhibits and promotes) the protease activity of the present ADAM protein is possible using this assay.

EXAMPLE 5

Preparation of Disintegrin Region 10 Amino Acids Deficient Expression Plasmid

A gene described in WO 97/09430 is a gene in which 30 base pairs (10 amino acids) are deleted in a disintegrin region in a protein coding region as compared with the gene (SEQ ID No.:3) obtained in the present invention. In order to compare the activity of a protein derived from this gene with that of a protein derived from the gene obtained in the present invention, the gene described in WO 97/09430 was obtained according to the following method. That is, a PCR reaction (30 seconds at 96° C., 30 seconds at 56° C., and 12 minutes at 72° C., 30 times) was conducted using two kinds of primers [CTC AGA TGT CCC ACA ATC ACA GTC (SEQ ID No: 19)] and [ACA TGT AAA ATC AAA GCA ACT TTT C (SEQ ID No.20)] in which each 5' side was phosphorylated and using pTB 2053 obtained in Example 1 as a template according to a protocol of Pfu turbo (manufactured by STRATAGENE). The PCR reaction solution was subjected to 1% agarose gel electrophoresis, and purified using QIAquick Gel Extraction Kit (manufactured by QIAGEN). This was self-cyclized using T4 ligase (manufactured by Nippon Gene) and transformed into *Escherichia coli* DH5α. Then, a plasmid was extracted from this *Escherichia coli*, a base sequence was determined, and it was confirmed that an expression plasmid (pATR-CT) in which a gene coding region described in the patent (WO 97/09430) was inserted into pcDNA3.1 was obtained.

EXAMPLE 6

Comparison of Bovine Nose Cartilage Proteoglycan Degrading Activity

A cartilage was taken from a bovine nose septum, cut into a cylinder using a cork borer having a diameter of 4 mm, and the cylinder cartilage was cut into a thickness of about 1 mm with a mess, to obtain a disc-like cartilage piece. Then, this cartilage piece was frozen and melted 5 times at −80° C. and 37° C., and heat-treated at 65° C. for 20 minutes, which was used as a substrate for the following activity measurement. One day before, $1\times10^4$ was seeded on a 48-well plate, and transfection was conducted using cultured COS7 cell. Transfection was conducted using Fugene6 (manufactured by Boehringer Mannheim) according to its protocol. After transfection for 4 hours, a disc-like bovine cartilage piece obtained above was added, and culturing was further continued at 37° C. After cultured for 2 days, sulfated glycosaminoglycan in the supernatant was measured according to a method of C. J. Handley and D. J. Buttle (Methods in Enzymology 248:47–58, 1995), and acceleration of proteoglycan degrading sthenia by various genes introduction was compared. The results thereof are shown in the following table, the proteoglycan degradation was significantly enhances by transfection of pTB2052 or pTB2053 but apparent degradation was not recognized in the gene described in the International Publication (WO 97/09430).

TABLE 3

| Introduced plasmid | SGAG (mg/ml) | SD value |
| --- | --- | --- |
| mock transfection | 34.11 | 3.64 |
| pTB2052 | 62.17 | 11.77 |
| pTB2053 | 57.03 | 10.60 |
| pATR-CT | 38.28 | 16.02 |

SGAG (sulfated glycosaminoglycan) value is an average of tetraplicate experiments.

EXAMPLE 7

Obtaining of an Anti-ADAM Protein Polyclonal Antibody

The recombinant human ADAM protein (200 µg) obtained in Example 3 was suspended in a complete Freund's adjuvant, which was used to primarily immunize Japanese white rabbit. Thereafter, 4 times every 2 weeks, 400 µg of a recombinant human ADAM protein was suspended in an incomplete Freund's adjuvant, which was used to immunize Japanese white rabbit. By taking whole blood 1 week after the last immunization, about 50 ml of serum was obtained. An antibody titer was measured as follows. After a recombinant human ADAM protein was fixed to 0.5 µg/well, dilute rabbit serum was added to a 96-well plate blocked with BSA, which was allowed to stand at room temperature for 2 hours. After washed with PBS containing 0.1% Tween-20, an anti-rabbit IgG-peroxidase (manufactured by Capel Company) was added, and allowed to stand for 2 hours. After washing, a citrate-phosphate buffer containing O-phenylenediamine and hydrogen peroxide was added, which was developed for 20 minutes. After the reaction was stopped by 1M sulfuric acid, the development at 492 nM was measured using a platereader. As a result, antiserum showing about 10,000-fold antibody titer of that of a non-immunized rabbit was obtained.

EXAMPLE 8

Cloning of a Promoter and an Enhancer of a Rat II Type Collagen Gene

A promoter region of a rat II type collagen gene was obtained by a PCR method using primers [5'-GTGGTG-GTGGACAACTAGGAAACTCTGG-3' (SEQ ID No: 21)] and [5'-CGAGGCGAATCATGGCTCACCGCG-3' (SEQ ID No: 22)] designed based on a base sequence of Kohno et al. (J. Biol. Chem. 260:4441, 1985). The resulting about 1.2 kb fragment was cloned into pCR II-TOPO using TOPO TA Cloning Kit (Invitrogen) according to the attached protocol (pCRII-promoter 2). A base sequence thereof was confirmed with a DNA sequencer manufacture by ABI according to the conventional method. The pCRII plasmid was excised at NotI (5' side) of a multiple cloning site and a SmaI site within a promoter sequence, which was used for experiment.

An enhancer region of a rat II type collagen gene was obtained by a PCR method using primers [5'-TCCACGCGTTTGGGAAACTTCTTGGCTGCG-3' (SEQ ID No: 23)] and [5'-GCTTCGTCGCCGCTACGCGTGGGGC-CGGA-3' (SEQ ID No: 24)] designed so as to produce a MluI site based on a base sequence of Krebsbash et al. (J. Biol. Chem. 271:4298, 1996). A base sequence of the resulting 0.35 kb MluI fragment was confirmed with a DNA sequencer manufactured by ABI Company according to the conventional method. Then, an EcoRI linker was added to the MluI fragment, and inserted into an EcoRI site of pBluescript KSII+ (pKS-enhancer 1–4).

EXAMPLE 9

Preparation of an Expression Vector for Transgenic Rats

An expression vector for a transgenic rat, pTB2076 (FIG. 5) was constructed according to the conventional method. In the present plasmid, the following fragments 1) to 5) are inserted into a NotI site of pBluescript II KS+.

1) Col2A1 promoter: A rat II type collagen gene promoter region, 1,120 bp fragment from NotI within a multiple cloning site of pCRII described in Example 8 to a SmaI site within a II type collagen gene promoter (SmaI site is converted into SalI site).

2) SV40 splicing: A 5' side of a fragment containing a splicing site derived from pTB399 (R. Sasada et al., Cell Structure and Function 12:205, 1987) was altered to SalI and a 3' side was altered to ClaI.

3) ADAM: novel ADAM gene.

An about 2.4 kb gene fragment in which a ClaI site was added to a 5' side and a BglII site was added to a 3' side by performing a PCR reaction (30 cycles of 95° C., 20 seconds, 52° C., 10 seconds and 72° C., 3 minutes) using the plasmid (pTB2052) obtained in Example 1 as a template and synthetic primers [5'-ATC GAT TGA GCG AGA AGA GCA GAC ACC-3' (SEQ ID No: 25)] and [5'-AGA TCT TGC CAT CCA GAT TTT CCA GTT T-3' (SEQ ID No: 26)] and employing Pfu turbo (STRATAGENE)(corresponding to 13th to 2448th bases in FIGS. 3 and 4).

4) SV40 ployA: A BglII and HindIII fragment containing a polyA addition signal derived from pTB399 (R. Sasada et al., Cell Structure and Function 12:205, 1987).

5) Col2A1 enhancer: A fragment from a HindIII site to a NotI site of pKS-enhancer 1–4 containing an enhancer region of a rat II type collagen gene described in Example 8.

EXAMPLE 10

Production of Transgenic Rats

Rat SD (ISG) line, 8 weeks-old, was purchased for taking eggs, reared for 1 week under 7:00–19:00 12 hours luminesce, follicle-stimulating hormone (pregnant horse serum gonadotropin, generally abbreviated as PMSG) (30 IU/individual) was first injected intraperitoneally at 11:00 on the first day, luteinization hormone (human chorionic gonadotropin, generally abbreviated as hCG)(51U/individual) was injected intraperitoneally at 11:00 on the third day, and was made to 1:1 share the same space with and mate with an individual of male rat SD(ISG) line, 10 or more weeks age, after 14:00. At 9:00 on the fourth day vagina plug of the mated female rat was conducted, the individual for which vagina plug confirmation was performed was slaughtered at 13:30 and, thereafter, taking eggs was initiated. Fertilized eggs which were pronucleus formed eggs were selected. The plasmid pTB2076 obtained in Example 9 was cut with NotI from 14:30, a fragment containing a novel ADAM gene was prepared to the concentration of 10 μg/ml, 1 to 2 μl of which was injected in a male pronucleus of an egg of a SD line rat at a single cell phase which was fertilized, while observing under a microscope. Subsequently, the egg cell was cultured in the per se known HER medium, 2 cell phase embryo was confirmed at 13:30 on the fifth day, the egg cell was transplanted into an uterine tube of a false pregnant female Wistar line rat, and which was implanted according to a method described by Wagner et al. (Proc. Nal. Acad. Sc. U.S.A., 78:5016, 1981). A false pregnant female Wistar line rat (11 or more weeks age) was injected subctaneously (50 μg individual) with Conceral (Takeda Chemical Industries, Ltd.) at 11:00 on the 0 day, and was made to 1:1 share the same space with and mate with an individual of a male Wistar line, 12 or more weeks age, after 15:00 on the fourth day. Vagina plug confirmation of the mated female rat was performed at 9:00 on the fifth day, which was used for the above purpose.

EXAMPLE 11

Gene Analysis of Transgenic Rats

By using a DNA taken from a tail of a born cow which reached 3 weeks age, according to a method of B. HOGAN et al. (MANUPULATING THE MOUSE EMBRYO, 1986, COLD SPRING HARVOR LABORATORIES), a PCR was conducted using a primer [5'-CGCCGCTGGGCTGC-CGGGTC-3'(SEQ ID No: 27)] designed based on a rat II type collagen promoter sequence described in Example 8 and a primer [5'-TCGATCCCGATGTATGGGGC-3'(SEQ ID No: 28)] designed based on a novel ADAM protein gene sequence described in Example 1 (a DNA fragment consisting of a base sequence complementary to a base sequence corresponding to 293rd to 308th bases in the base sequence represented by SEQ ID No: 16). As a result of analysis of the total 95 of born rats, PCR positive individuals for which a 780 bp PCR fragment was detected was 6 individuals.

Genomic DNAs of these 6 PCR positive individuals were analyzed by a Southern hybridization method. That is, 10 μg of a DNA was completely cut, subjected to 1.0% agarose electrophoresis, and transferred to a nylon filter. This filter was hybridized overnight with a probe in which a novel gene used in Example 9 (about 2.4 kb gene fragment (corresponding to 13th to 2448th bases in FIGS. 3 and 4)) labeled with a DIG DNA labeling kit (manufactured by Boehringer Mannheim), and then washed with 2×SSC, 0.1% SDS twice at room temperature, and washed with 0.1×SSC, 0.1% SDS twice at 68° C. For detection, a DIG fluorescent detection kit (manufactured by Boehringer Mannheim) was used. As a result, in all these 6 individuals, each 1.9 Kb fragment was observed and introduction of the novel ADAM gene was confirmed. In addition, it was confirmed that a copy number of the introduced gene was 40 copies in an individual number RCA-14 (female), 5 copies in RCA-22 (male), 40 copies in RCA-50 (male), 2 copies in RCA-79 (male), 10 copies in RCA-83 (female) and 40 copies in RCA-86 (male).

EXAMPLE 12

Expression of a Human ADAM Protein in a Caudal Vertebra of a Transgenic Rat

About 5 mm of a caudal vertebra end tissue of the transgenic rat RCA-14 (male) was excised from the living body. This tissue was fixed with 4% paraformaldehyde at room temperature overnight. Thereafter, the tissue was defatted with 70% ethanol at room temperature for 24 hours, and deashed with 0.5M EDTA (pH=8.0) at room temperature for 2 weeks. Deashment was confirmed by the fact that stabbing of a tissue with a neeedle leads to easy penetration. After completion of deashment, the tissue was washed with water at room temperature, and a paraffin block was made according to the conventional method (Histological Study, Yutaka Sano, Nanzando). The block was stored at 4° C. to a thin section. At sectioning, the block was returned to room temperature, the piece was cut thinnly with a 5 micrometer, expanded on warm water, mounted on a glass slide, and dried at 37° C. overnight. Immunostaining was performed using a rabbit polyclonal antibody described in Example 7 as the primary antibody according to a protocol of vectastain ABC universal kit (Vector Company). Development was conducted using a peroxidase substrate AEC kit (Vector Company) according to the attached protocol.

As a result, the presence of the present novel ADAM protein was confirmed over a growing cartilage cell to hypertrophic cartilage cell layer in a caudal vertebrae end tissue of a DNA transferred rat RCA-14 (female).

A transgenic rat in which the thus obtained present novel ADAM gene was incorporated develops deformity of a joint such as rheumatoid arthritis, joint disease associated with damage, bone disease and chronic inflammatory disease in some cases and it can be utilized as those diseases model animal. Further, elucidation of the mechanism of these diseases and a method of treating these diseases can be studied using the present DNA transferred rat. In addition, transgenic rats of interest can be effectively at a higher yield can be obtained by a method of making the present transgenic rat.

EXAMPLE 13

Search on a Substance Which Regulates the Protease Activity of an ADAM Protein

An enzymatic reaction was initiated by adding 75 μl of a buffer (83.3 mM Tris-HCl, pH 7.5, 16.7 mM NaCl, 1.67 mM $CaCl_2$, 16.7 μM $CoCl_2$, and 0.067% BSA) to a solution (25 μl) of the ADAM protein obtained according to the same manner as that of Example 3, and adding 25 μl of a solution of a substrate (50 μM Nma-Pro-Lys-Pro-Leu-Ala-Nva-Trp-Lys(DNP)-$NH_2$, 0.05% BSA, and 5% DMSO). After a temperature was held at 37° C. for 2 hours, 100 μl of a 0.5M acetate buffer (pH 3.0) was added to stop the enzymatic reaction. The fluorescent intensity in the case of addition of no an enzyme solution [fluorescent intensity was measured at an excitation wavelength of 340 nm and a measuring wavelength of 450 nm using a fluorescent platereader (Corona MTP-32)] was 10, while the fluorescent intensity in the case of addition of the enzyme solution was 180. Accordingly, it was made clear that the present ADAM protein shows the protease activity also in this condition.

10 μl of a test compound adjusted to the predetermined concentration (dissolved in 50% DMSO) was added to the above activity measuring system. As a result, actinonin (Sigma A6671) showed an $IC_{50}$ value (concentration of a test compound which 50% inhibits the protease activity) of 0.6 mM, and N-CBZ-Pro-Leu-Gly-hydroxamate (Sigma C8537) showed an $IC_{50}$ value of about 0.1 mM. From this, it was considered that search on a substance which regulates (inhibits or promotes) the protease activity of the present ADAM protein can be conducted using the present assay system.

INDUSTRIAL APPLICABILITY

The present protein and a DNA encoding it can be used as an agent for treating or preventing disease such as disc herniation, ischialgia, glomerular nephritis, diabetic nephropathy, hepatic fibrosis, pulmonary fibrosis or osteopetrosis. In addition, the present protein is useful as a reagent for screening for a compound or a salt thereof, which promotes or inhibits the protease activity and/or the extracellular matrix degrading enzyme (in particular, the proteoglycan degrading enzymatic activity) of the present protein. Further, since an antibody against the present protein can specifically recognize the present protein, it can be used for quantitating the present protein in a test solution.

---

The invention claimed is:

1. An isolated DNA comprising a base sequence selected from the group consisting of:
   (a) a base sequence encoding amino acid residues 1 to 775 of SEQ ID NO:15;
   (b) a base sequence encoding the amino acid sequence of the ADAM polypeptide encoded by the cDNA contained in NIBH Accession No. FERM BP-6474;
   (c) a base sequence encoding a partial peptide of amino acid residues 1 to 775 of SEQ ID NO:15 wherein said partial peptide has proteoglycan degrading activity;
   (d) a first base sequence 95% or more identical to a second base sequence, wherein said second base sequence is (a) or (b), and wherein said first base sequence has proteoglycan degrading activity; and
   (e) a base sequence comprising a base sequence which hybridizes under stringent conditions to the base sequence of (a), (b), (c), or (d).

2. The isolated DNA of claim 1, wherein said base sequence is (a).

3. The isolated DNA of claim 1, wherein said base sequence is (b).

4. The isolated DNA of claim 1, wherein said base sequence is (c).

5. The isolated DNA of claim 1, wherein said base sequence is (d).

6. The isolated DNA of claim 1, wherein said base sequence is (e).

7. A recombinant vector comprising the DNA of claim 1.

8. The recombinant vector of claim 7 wherein said vector further comprises a promoter sequence.

9. The recombinant vector of claim 7 wherein said vector further comprises a signal sequence.

10. A method of producing a recombinant vector comprising inserting the isolated DNA of claim 1 into a vector.

11. A recombinant host cell comprising the isolated DNA of claim 1.

12. A recombinant host cell comprising the recombinant vector of claim 7.

13. A method of producing a host cell comprising transforming a host cell with the vector of claim 7.

14. A method for producing a protein, comprising:
   (a) culturing the host cell of claim 11 under conditions suitable to produce a polypeptide encoded by the DNA; and
   (b) recovering the protein from the cell culture.

15. A composition comprising the polynucleotide of claim 1 and a pharmaceutically acceptable carrier.

16. An isolated DNA comprising the base sequence of SEQ ID NO:16.

* * * * *

SEQUENCE LISTING

<160> NUMBER OF SEQ ID NOS: 32

<210> SEQ ID NO 1
<211> LENGTH: 540
<212> TYPE: PRT
<213> ORGANISM: Homo sapiens
<220> FEATURE:
<221> NAME/KEY: PEPTIDE
<222> LOCATION: (1)..(540)
<223> OTHER INFORMATION: An isolated  ADAM family protein

<400> SEQUENCE: 1

```
Met Leu Gln Gly Leu Leu Pro Val Ser Leu Leu Leu Ser Val Ala Val
1               5                   10                  15

Ser Ala Ile Lys Glu Leu Pro Gly Val Lys Lys Tyr Glu Val Val Tyr
            20                  25                  30

Pro Ile Arg Leu His Pro Leu His Lys Arg Glu Ala Lys Glu Pro Glu
        35                  40                  45

Gln Gln Glu Gln Phe Glu Thr Glu Leu Lys Tyr Lys Met Thr Ile Asn
    50                  55                  60

Gly Lys Ile Ala Val Leu Tyr Leu Lys Lys Asn Lys Asn Leu Leu Ala
65                  70                  75                  80

Pro Gly Tyr Thr Glu Thr Tyr Tyr Asn Ser Thr Gly Lys Glu Ile Thr
                85                  90                  95

Thr Ser Pro Gln Ile Met Asp Asp Cys Tyr Tyr Gln Gly His Ile Leu
            100                 105                 110

Asn Glu Lys Val Ser Asp Ala Ser Ile Ser Thr Cys Arg Gly Leu Arg
        115                 120                 125

Gly Tyr Phe Ser Gln Gly Asp Gln Arg Tyr Phe Ile Glu Pro Leu Ser
    130                 135                 140

Pro Ile His Arg Asp Gly Gln Glu His Ala Leu Phe Lys Tyr Asn Pro
145                 150                 155                 160

Asp Glu Lys Asn Tyr Asp Ser Thr Cys Gly Met Asp Gly Val Leu Trp
                165                 170                 175

Ala His Asp Leu Gln Gln Asn Ile Ala Leu Pro Ala Thr Lys Leu Val
            180                 185                 190

Lys Leu Lys Asp Arg Lys Val Gln Glu His Glu Lys Tyr Ile Glu Tyr
        195                 200                 205

Tyr Leu Val Leu Asp Asn Gly Glu Phe Lys Arg Tyr Asn Glu Asn Gln
```

```
                210                 215                 220
Asp Glu Ile Arg Lys Arg Val Phe Glu Met Ala Asn Tyr Val Asn Met
225                 230                 235                 240

Leu Tyr Lys Lys Leu Asn Thr His Val Ala Leu Val Gly Met Glu Ile
                245                 250                 255

Trp Thr Asp Lys Asp Lys Ile Lys Ile Thr Pro Asn Ala Ser Phe Thr
                260                 265                 270

Leu Glu Asn Phe Ser Lys Trp Arg Gly Ser Val Leu Ser Arg Arg Lys
                275                 280                 285

Arg His Asp Ile Ala Gln Leu Ile Thr Ala Thr Glu Leu Ala Gly Thr
                290                 295                 300

Thr Val Gly Leu Ala Phe Met Ser Thr Met Cys Ser Pro Tyr Ser Val
305                 310                 315                 320

Gly Val Val Gln Asp His Ser Asp Asn Leu Leu Arg Val Ala Gly Thr
                325                 330                 335

Met Ala His Glu Met Gly His Asn Phe Gly Met Phe His Asp Asp Tyr
                340                 345                 350

Ser Cys Lys Cys Pro Ser Thr Ile Cys Val Met Asp Lys Ala Leu Ser
                355                 360                 365

Phe Tyr Ile Pro Thr Asp Phe Ser Ser Cys Ser Arg Leu Ser Tyr Asp
                370                 375                 380

Lys Phe Phe Glu Asp Lys Leu Ser Asn Cys Leu Phe Asn Ala Pro Leu
385                 390                 395                 400

Pro Thr Asp Ile Ile Ser Thr Pro Ile Cys Gly Asn Gln Leu Val Glu
                405                 410                 415

Met Gly Glu Asp Cys Asp Cys Gly Thr Ser Glu Glu Cys Thr Asn Ile
                420                 425                 430

Cys Cys Asp Ala Lys Thr Cys Lys Ile Lys Ala Thr Phe Gln Cys Ala
                435                 440                 445

Leu Gly Glu Cys Cys Glu Lys Cys Gln Phe Lys Lys Ala Gly Met Val
                450                 455                 460

Cys Arg Pro Ala Lys Asp Glu Cys Asp Leu Pro Glu Met Cys Asn Gly
465                 470                 475                 480

Lys Ser Gly Asn Cys Pro Asp Asp Arg Phe Gln Val Asn Gly Phe Pro
                485                 490                 495

Cys His His Gly Lys Gly His Cys Leu Met Gly Thr Cys Pro Thr Leu
                500                 505                 510

Gln Glu Gln Cys Thr Glu Leu Trp Gly Pro Gly Arg Arg Thr Asn Pro
                515                 520                 525

Phe Pro Cys Ala Cys Ala Lys Glu Asn His Phe Arg
530                 535                 540

<210> SEQ ID NO 2
<211> LENGTH: 96
<212> TYPE: PRT
<213> ORGANISM: Homo sapiens
<220> FEATURE:
<221> NAME/KEY: PEPTIDE
<222> LOCATION: (1)..(96)
<223> OTHER INFORMATION: Isolated fragment of Protein of Seq ID No.1
      (aa 400-495)

<400> SEQUENCE: 2

Leu Pro Thr Asp Ile Ile Ser Thr Pro Ile Cys Gly Asn Gln Leu Val
1               5                   10                  15

Glu Met Gly Glu Asp Cys Asp Cys Gly Thr Ser Glu Glu Cys Thr Asn
```

```
                    20                  25                  30
Ile Cys Cys Asp Ala Lys Thr Cys Lys Ile Lys Ala Thr Phe Gln Cys
                35                  40                  45

Ala Leu Gly Glu Cys Cys Glu Lys Cys Gln Phe Lys Lys Ala Gly Met
            50                  55                  60

Val Cys Arg Pro Ala Lys Asp Glu Cys Asp Leu Pro Glu Met Cys Asn
65                  70                  75                  80

Gly Lys Ser Gly Asn Cys Pro Asp Asp Arg Phe Gln Val Asn Gly Phe
                85                  90                  95

<210> SEQ ID NO 3
<211> LENGTH: 1620
<212> TYPE: DNA
<213> ORGANISM: Homo sapiens
<220> FEATURE:
<221> NAME/KEY: misc_feature
<222> LOCATION: (1)..(1620)
<223> OTHER INFORMATION: Isolated DNA encoding for the protein of
      SEQ ID NO.1

<400> SEQUENCE: 3
atgttgcaag gtctcctgcc agtcagtctc ctcctctctg ttgcagtaag tgctataaaa      60
gaactccctg gggtgaagaa gtatgaagtg gtttatccta taagacttca tccactgcat    120
aaaagagagg ccaaagagcc agagcaacag gaacaatttg aaactgaatt aaagtataaa    180
atgacaatta atggaaaaat tgcagtgctt tatttgaaaa aaacaagaa cctccttgca     240 ccaggctaca cggaaacata ttataattcc actggaaagg atcaccac aagcccacaa      300 attatggatg attgttatta tcaaggacat attcttaatg aaaaggtttc tgacgctagc    360
atcagcacat gtagggggtct aaggggctac ttcagtcagg gggatcaaag atactttatt   420
gaacctttaa gccccataca tcgggatgga caggagcatg cactcttcaa gtataaccct    480
gatgaaaaga attatgacag cacctgtggg atggatggtg tgttgtgggc ccacgatttg    540
cagcagaaca ttgccctacc tgccaccaaa ctagtaaaat gaaagacag gaaggttcag    600 gaacatgaga aatacataga atattatttg gtcctggata atggtgagtt taaaaggtac    660
aatgagaatc aagatgagat cagaaagagg gtatttgaga tggctaatta tgtcaacatg    720
ctttataaaa agctcaatac tcatgtggcc ttagttggta tggaaatctg gactgacaag    780
gataagataa agataacccc aaatgcaagc ttcaccttgg agaatttttc taaatggagg    840
gggagtgttc tctcaagaag aaagcgtcat gatattgctc agttaatcac agcaacagaa    900
cttgctggaa cgactgtggg tcttgcattt atgtctacaa tgtgttctcc ttattctgtt    960
ggcgttgttc aggaccacag cgataatctt cttagagttg cagggacaat ggcacatgaa   1020
atgggccaca actttggaat gtttcatgac gactattctt gcaagtgtcc ttctacaata   1080
tgtgtgatgg acaaagcact gagcttctat atacccacag acttcagttc ctgcagccgt   1140
ctcagctatg acaagttttt tgaagataaa ttatcaaatt gcctctttaa tgctccattg   1200
cctacagata tcatatccac tccaatttgt gggaaccagt tggtggaaat gggagaggac   1260
tgtgattgtg ggacatctga ggaatgtacc aatatttgct gtgatgctaa gacatgtaaa   1320
atcaaagcaa cttttcaatg tgcattagga gaatgttgtg aaaaatgcca atttaaaaag   1380
gctgggatgg tgtgcagacc agcaaaagat gagtgcgacc tgcctgaaat gtgtaatggt   1440
aaatctggta attgtcctga tgatagattc caagtcaatg gcttcccttg ccatcacggg   1500
aagggccact gcttgatggg gacatgcccc acactgcagg agcagtgcac agagctgtgg   1560
```
ggaccaggta ggaggacaaa tcctttcccc tgtgcatgtg cgaaggaaaa tcatttcaga    1620

<210> SEQ ID NO 4
<211> LENGTH: 288
<212> TYPE: DNA
<213> ORGANISM: Homo sapiens
<220> FEATURE:
<221> NAME/KEY: misc_feature
<222> LOCATION: (1)..(288)
<223> OTHER INFORMATION: Artificial DNA encoding for peptide of
      SEQ ID NO.2

<400> SEQUENCE: 4
ttgcctacag atatcatatc cactccaatt tgtgggaacc agttggtgga atgggagag      60 gactgtgatt gtgggacatc tgaggaatgt accaatattt gctgtgatgc taagacatgt   120
aaaatcaaag caacttttca atgtgcatta ggagaatgtt gtgaaaaatg ccaatttaaa   180
aaggctggga tggtgtgcag accagcaaaa gatgagtgcg acctgcctga aatgtgtaat   240
ggtaaatctg gtaattgtcc tgatgataga ttccaagtca atggcttc                288

<210> SEQ ID NO 5
<211> LENGTH: 201
<212> TYPE: PRT
<213> ORGANISM: Homo sapiens
<220> FEATURE:
<221> NAME/KEY: PEPTIDE
<222> LOCATION: (1)..(201)
<223> OTHER INFORMATION: Isolated fragment of protein of SEQ ID NO.1
      (aa 199-399)

<400> SEQUENCE: 5

Val Gln Glu His Glu Lys Tyr Ile Glu Tyr Tyr Leu Val Leu Asp Asn
1               5                   10                  15

Gly Glu Phe Lys Arg Tyr Asn Glu Asn Gln Asp Glu Ile Arg Lys Arg
            20                  25                  30

Val Phe Glu Met Ala Asn Tyr Val Asn Met Leu Tyr Lys Lys Leu Asn
        35                  40                  45

Thr His Val Ala Leu Val Gly Met Glu Ile Trp Thr Asp Lys Asp Lys
    50                  55                  60

Ile Lys Ile Thr Pro Asn Ala Ser Phe Thr Leu Glu Asn Phe Ser Lys
65                  70                  75                  80

Trp Arg Gly Ser Val Leu Ser Arg Arg Lys Arg His Asp Ile Ala Gln
                85                  90                  95

Leu Ile Thr Ala Thr Glu Leu Ala Gly Thr Thr Val Gly Leu Ala Phe
            100                 105                 110

Met Ser Thr Met Cys Ser Pro Tyr Ser Val Gly Val Val Gln Asp His
        115                 120                 125

Ser Asp Asn Leu Leu Arg Val Ala Gly Thr Met Ala His Glu Met Gly
    130                 135                 140

His Asn Phe Gly Met Phe His Asp Asp Tyr Ser Cys Lys Cys Pro Ser
145                 150                 155                 160

Thr Ile Cys Val Met Asp Lys Ala Leu Ser Phe Tyr Ile Pro Thr Asp
                165                 170                 175

Phe Ser Ser Cys Ser Arg Leu Ser Tyr Asp Lys Phe Phe Glu Asp Lys
            180                 185                 190

Leu Ser Asn Cys Leu Phe Asn Ala Pro
        195                 200

<210> SEQ ID NO 6

-continued

```
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Isolated fragment of Protein of SEQ ID NO.1
      (aa 428-437)

<400> SEQUENCE: 6

Glu Cys Thr Asn Ile Cys Cys Asp Ala Lys
1               5                   10

<210> SEQ ID NO 7
<211> LENGTH: 23
<212> TYPE: DNA
<213> ORGANISM: Artificial sequence
<220> FEATURE:
<223> OTHER INFORMATION: Nucleic Acid primer
<220> FEATURE:
<221> NAME/KEY: misc_feature
<222> LOCATION: (6)..(6)
<223> OTHER INFORMATION: n equals a, t, g, or c

<400> SEQUENCE: 7
gtrgansmdk sdgarsartg tga                                            23

<210> SEQ ID NO 8
<211> LENGTH: 26
<212> TYPE: DNA
<213> ORGANISM: Artificial sequence
<220> FEATURE:
<223> OTHER INFORMATION: Nucleic Acid primer
<220> FEATURE:
<221> NAME/KEY: misc_feature
<222> LOCATION: (13)..(13)
<223> OTHER INFORMATION: n equals a, t, g, or c
<220> FEATURE:
<221> NAME/KEY: misc_feature
<222> LOCATION: (21)..(21)
<223> OTHER INFORMATION: n equals a, t, g, or c

<400> SEQUENCE: 8
ayytgwdbrd dwncdkvdds ngggca                                         26

<210> SEQ ID NO 9
<211> LENGTH: 28
<212> TYPE: DNA
<213> ORGANISM: Artificial sequence
<220> FEATURE:
<223> OTHER INFORMATION: Nucleic Acid primer

<400> SEQUENCE: 9
atcacagtcc tctcccattt ccaccaac                                       28

<210> SEQ ID NO 10
<211> LENGTH: 26
<212> TYPE: DNA
<213> ORGANISM: Artificial sequence
<220> FEATURE:
<223> OTHER INFORMATION: Nucleic Acid Primer

<400> SEQUENCE: 10
cacatttcag gcaggtcgca ctcatc                                         26

<210> SEQ ID NO 11
<211> LENGTH: 27
<212> TYPE: DNA
<213> ORGANISM: Artificial sequence
```

```
<220> FEATURE:
<223> OTHER INFORMATION: Nucleic Acid Primer

<400> SEQUENCE: 11
tcgctgtggt cctgaacaac gccaaca                                          27

<210> SEQ ID NO 12
<211> LENGTH: 28
<212> TYPE: DNA
<213> ORGANISM: Artificial sequence
<220> FEATURE:
<223> OTHER INFORMATION: Nucleic Acid Primer

<400> SEQUENCE: 12
cacaccatcc atcccacagg tgctgtca                                         28

<210> SEQ ID NO 13
<211> LENGTH: 28
<212> TYPE: DNA
<213> ORGANISM: Artificial sequence
<220> FEATURE:
<223> OTHER INFORMATION: Nucleic Acid Primer

<400> SEQUENCE: 13
ggaaccagtt ggtggaaatg ggagagga                                         28

<210> SEQ ID NO 14
<211> LENGTH: 29
<212> TYPE: DNA
<213> ORGANISM: Artificial sequence
<220> FEATURE:
<223> OTHER INFORMATION: Nucleic Acid Primer

<400> SEQUENCE: 14
aggactgtga ttgtgggacg tctgaggaa                                        29

<210> SEQ ID NO 15
<211> LENGTH: 775
<212> TYPE: PRT
<213> ORGANISM: Homo sapiens
<220> FEATURE:
<221> NAME/KEY: PEPTIDE
<222> LOCATION: (1)..(775)
<223> OTHER INFORMATION: An isolated ADAM family protein

<400> SEQUENCE: 15
```

Met Leu Gln Gly Leu Leu Pro Val Ser Leu Leu Ser Val Ala Val
1               5                   10                  15

Ser Ala Ile Lys Glu Leu Pro Gly Val Lys Lys Tyr Glu Val Tyr
                20                  25                  30

Pro Ile Arg Leu His Pro Leu His Lys Arg Glu Ala Lys Glu Pro Glu
                35                  40                  45

Gln Gln Glu Gln Trp Glu Thr Glu Leu Lys Tyr Lys Met Thr Ile Asn
            50                  55                  60

Gly Lys Ile Ala Val Leu Tyr Leu Lys Lys Asn Lys Asn Leu Leu Ala
65                  70                  75                  80

Pro Gly Tyr Thr Glu Thr Tyr Tyr Asn Ser Thr Gly Lys Glu Ile Thr
                85                  90                  95

Thr Ser Pro Gln Ile Met Trp Trp Trp Tyr Gln Gly His Ile Leu
                100                 105                 110

Asn Glu Lys Val Ser Trp Ala Ser Ile Ser Thr Trp Arg Gly Leu Arg
            115                 120                 125

-continued

Gly Tyr Trp Ser Gln Gly Trp Gln Arg Tyr Trp Ile Glu Pro Leu Ser
        130             135             140

Pro Ile His Arg Trp Gly Gln Glu His Ala Leu Trp Lys Tyr Asn Pro
145             150              155             160

Trp Glu Lys Asn Tyr Trp Ser Thr Trp Gly Met Trp Gly Val Leu Trp
                165             170             175

Ala His Trp Leu Gln Gln Asn Ile Ala Leu Pro Ala Thr Lys Leu Val
            180             185             190

Lys Leu Lys Trp Arg Lys Val Gln Glu His Glu Lys Tyr Ile Glu Tyr
        195             200             205

Tyr Leu Val Leu Trp Asn Gly Glu Trp Lys Arg Tyr Asn Glu Asn Gln
    210             215             220

Trp Glu Ile Arg Lys Arg Val Trp Glu Met Ala Asn Tyr Val Asn Met
225             230             235             240

Leu Tyr Lys Lys Leu Asn Thr His Val Ala Leu Val Gly Met Glu Ile
                245             250             255

Trp Thr Trp Lys Trp Lys Ile Lys Ile Thr Pro Asn Ala Ser Trp Thr
            260             265             270

Leu Glu Asn Trp Ser Lys Trp Arg Gly Ser Val Leu Ser Arg Arg Lys
        275             280             285

Arg His Trp Ile Ala Gln Leu Ile Thr Ala Thr Glu Leu Ala Gly Thr
    290             295             300

Thr Val Gly Leu Ala Trp Met Ser Thr Met Trp Ser Pro Tyr Ser Val
305             310             315             320

Gly Val Val Gln Trp His Ser Trp Asn Leu Leu Arg Val Ala Gly Thr
                325             330             335

Met Ala His Glu Met Gly His Asn Trp Gly Met Trp His Trp Trp Tyr
            340             345             350

Ser Trp Lys Trp Pro Ser Thr Ile Trp Val Met Trp Lys Ala Leu Ser
        355             360             365

Trp Tyr Ile Pro Thr Trp Trp Ser Ser Trp Ser Arg Leu Ser Tyr Trp
    370             375             380

Lys Trp Trp Glu Trp Lys Leu Ser Asn Trp Leu Trp Asn Ala Pro Leu
385             390             395             400

Pro Thr Trp Ile Ile Ser Thr Pro Ile Trp Gly Asn Gln Leu Val Glu
                405             410             415

Met Gly Glu Trp Trp Trp Trp Gly Thr Ser Glu Glu Trp Thr Asn Ile
            420             425             430

Trp Trp Trp Ala Lys Thr Trp Lys Ile Lys Ala Thr Trp Gln Trp Ala
        435             440             445

Leu Gly Glu Trp Trp Glu Lys Trp Gln Trp Lys Lys Ala Gly Met Val
    450             455             460

Trp Arg Pro Ala Lys Trp Glu Trp Trp Leu Pro Glu Met Trp Asn Gly
465             470             475             480

Lys Ser Gly Asn Trp Pro Trp Trp Arg Trp Gln Val Asn Gly Trp Pro
                485             490             495

Trp His His Gly Lys Gly His Trp Leu Met Gly Thr Trp Pro Thr Leu
            500             505             510

Gln Glu Gln Trp Thr Glu Leu Trp Gly Pro Gly Thr Glu Val Ala Trp
        515             520             525

Lys Ser Trp Tyr Asn Arg Asn Glu Gly Ser Lys Tyr Gly Tyr Trp
    530             535             540

Arg Arg Val Trp Trp Thr Leu Ile Pro Trp Lys Ala Asn Trp Thr Met

-continued

```
545                 550                 555                 560

Trp Gly Lys Leu Trp Trp Gln Gly Gly Ser Trp Asn Leu Pro Trp Lys
                565                 570                 575

Gly Arg Ile Val Thr Trp Leu Thr Trp Lys Thr Trp Trp Pro Glu Trp
            580                 585                 590

Thr Ser Gln Glu Ile Gly Met Val Ala Asn Gly Thr Lys Trp Gly Trp
        595                 600                 605

Asn Lys Val Trp Ile Asn Ala Glu Trp Val Trp Ile Glu Lys Ala Tyr
    610                 615                 620

Lys Ser Thr Asn Trp Ser Ser Lys Trp Lys Gly His Ala Val Trp Trp
625                 630                 635                 640

His Glu Leu Gln Trp Gln Trp Glu Glu Gly Trp Ile Pro Pro Trp Trp
                645                 650                 655

Trp Trp Ser Ser Val Val Trp His Trp Ser Ile Val Val Gly Val Leu
            660                 665                 670

Trp Pro Met Ala Val Ile Trp Val Val Val Ala Met Val Ile Arg His
        675                 680                 685

Gln Ser Ser Arg Glu Lys Gln Lys Lys Trp Gln Arg Pro Leu Ser Thr
    690                 695                 700

Thr Gly Thr Arg Pro His Lys Gln Lys Arg Lys Pro Gln Met Val Lys
705                 710                 715                 720

Ala Val Gln Pro Gln Glu Met Ser Gln Met Lys Pro His Val Tyr Trp
                725                 730                 735

Leu Pro Val Glu Gly Asn Glu Pro Pro Ala Ser Trp His Lys Trp Thr
            740                 745                 750

Asn Ala Leu Pro Pro Thr Val Trp Lys Trp Asn Pro Met Ser Thr Pro
        755                 760                 765

Lys Trp Ser Asn Pro Lys Ala
    770                 775
```

<210> SEQ ID NO 16
<211> LENGTH: 2325
<212> TYPE: DNA
<213> ORGANISM: Homo sapiens
<220> FEATURE:
<221> NAME/KEY: misc_feature
<222> LOCATION: (1)..(2325)
<223> OTHER INFORMATION: Isolated nucleic acid encoding for a protein of SEQ ID NO. 15

<400> SEQUENCE: 16

```
atgttgcaag gtctcctgcc agtcagtctc ctcctctctg ttgcagtaag tgctataaaa     60
gaactccctg ggtgaagaa gtatgaagtg gtttatccta taagacttca tccactgcat     120
aaaagagagg ccaaagagcc agagcaacag gaacaatttg aaactgaatt aaagtataaa    180
atgacaatta atggaaaaat tgcagtgctt tatttgaaaa aaaacaagaa cctccttgca    240
ccaggctaca cggaaacata ttataattcc actggaaagg agatcaccac aagcccacaa    300
attatggatg attgttatta tcaaggacat attcttaatg aaaaggtttc tgacgctagc    360
atcagcacat gtaggggtct aaggggctac ttcagtcagg gggatcaaag atactttatt    420
gaacctttaa gccccataca tcgggatgga caggagcatg cactcttcaa gtataaccct    480
gatgaaaaga attatgacag cacctgtggg atggatggtg tgttgtgggc ccacgatttg    540
cagcagaaca ttgccctacc tgccaccaaa ctagtaaaat tgaaagacag gaaggttcag    600
gaacatgaga aatacataga atattatttg gtcctggata atggtgagtt taaaaggtac    660
```

```
aatgagaatc aagatgagat cagaaagagg gtatttgaga tggctaatta tgtcaacatg    720
ctttataaaa agctcaatac tcatgtggcc ttagttggta tggaaatctg gactgacaag    780
gataagataa agataacccc aaatgcaagc ttcaccttgg agaattttc taaatggagg     840 gggagtgttc tctcaagaag aaagcgtcat gatattgctc agttaatcac agcaacagaa    900
cttgctggaa cgactgtggg tcttgcattt atgtctacaa tgtgttctcc ttattctgtt    960
ggcgttgttc aggaccacag cgataatctt cttagagttg cagggacaat ggcacatgaa    1020
atgggccaca actttggaat gtttcatgac gactattctt gcaagtgtcc ttctacaata    1080
tgtgtgatgg acaaagcact gagcttctat atacccacag acttcagttc ctgcagccgt    1140
ctcagctatg acaagttttt tgaagataaa ttatcaaatt gcctctttaa tgctccattg    1200
cctacagata tcatatccac tccaatttgt gggaaccagt tggtggaaat gggagaggac    1260
tgtgattgtg ggacatctga ggaatgtacc aatatttgct gtgatgctaa gacatgtaaa    1320
atcaaagcaa cttttcaatg tgcattagga gaatgttgtg aaaaatgcca atttaaaaag    1380
gctgggatgg tgtgcagacc agcaaaagat gagtgcgacc tgcctgaaat gtgtaatggt    1440
aaatctggta attgtcctga tgatagattc caagtcaatg gcttcccttg ccatcacggg    1500
aagggccact gcttgatggg acatgccccc acactgcagg agcagtgcac agagctgtgg    1560
ggaccaggaa ctgaggttgc agataagtca tgttacaaca ggaatgaagg tgggtcaaag    1620
tacgggtact gtcgcagagt ggatgacaca ctcattccct gcaaagcaaa tgataccatg    1680
tgtgggaagt tgttctgtca aggtgggtcg gataatttgc cctggaaagg acggatagtg    1740
actttcctga catgtaaaac atttgatcct gaagacacaa gtcaagaaat aggcatggtg    1800
gccaatggaa ctaagtgtgg cgataacaag gtttgcatta atgcagaatg tgtggatatt    1860
gagaaagcct acaaatcaac caattgctca tctaagtgca aggacatgc tgtgtgtgac     1920 catgagctcc agtgtcaatg tgaggaagga tggatccctc ccgactgcga tgactcctca    1980
gtggtcttcc acttctccat tgtggttggg gtgctgttcc caatggcggt cattttgtg     2040 gtggttgcta tggtaatccg gcaccagagc tccagagaaa agcagaagaa agatcagagg    2100
ccactatcta ccactggcac caggccacac aaacagaaga ggaaacccca gatggtaaag    2160
gctgttcaac cccaagagat gagtcagatg aagccccatg tgtatgatct gccagtagaa    2220
ggcaatgagc ccccagcctc ttttcataaa gacacaaacg cacttccccc tactgttttc    2280
aaggataatc caatgtctac acctaaggac tcaaatccaa aagca                    2325
```

```
<210> SEQ ID NO 17
<211> LENGTH: 30
<212> TYPE: DNA
<213> ORGANISM: Artificial sequence
<220> FEATURE:
<223> OTHER INFORMATION: Nucleic Acid Primer

<400> SEQUENCE: 17
catatggttc aggaacatga gaaatacata                                      30

<210> SEQ ID NO 18
<211> LENGTH: 30
<212> TYPE: DNA
<213> ORGANISM: Artificial sequence
<220> FEATURE:
<223> OTHER INFORMATION: Nucleic Acid Primer

<400> SEQUENCE: 18
ctcgaggaag ccattgactt ggaatctatc                                      30
```

<210> SEQ ID NO 19
<211> LENGTH: 24
<212> TYPE: DNA
<213> ORGANISM: Artificial sequence
<220> FEATURE:
<223> OTHER INFORMATION: Nucleic Acid Primer

<400> SEQUENCE: 19
ctcagatgtc ccacaatcac agtc                                    24

<210> SEQ ID NO 20
<211> LENGTH: 25
<212> TYPE: DNA
<213> ORGANISM: Artificial sequence
<220> FEATURE:
<223> OTHER INFORMATION: Nucleic Acid Primer

<400> SEQUENCE: 20
acatgtaaaa tcaaagcaac ttttc                                   25

<210> SEQ ID NO 21
<211> LENGTH: 28
<212> TYPE: DNA
<213> ORGANISM: Artificial sequence
<220> FEATURE:
<223> OTHER INFORMATION: Nucleic Acid Primer

<400> SEQUENCE: 21
gtggtggtgg acaactagga aactctgg                                28

<210> SEQ ID NO 22
<211> LENGTH: 24
<212> TYPE: DNA
<213> ORGANISM: Artificial sequence
<220> FEATURE:
<223> OTHER INFORMATION: Nucleic Acid Primer

<400> SEQUENCE: 22
cgaggcgaat catggctcac cgcg                                    24

<210> SEQ ID NO 23
<211> LENGTH: 30
<212> TYPE: DNA
<213> ORGANISM: Artificial sequence
<220> FEATURE:
<223> OTHER INFORMATION: Nucleic Acid Primer

<400> SEQUENCE: 23
tccacgcgtt tgggaaactt cttggctgcg                              30

<210> SEQ ID NO 24
<211> LENGTH: 29
<212> TYPE: DNA
<213> ORGANISM: Artificial sequence
<220> FEATURE:
<223> OTHER INFORMATION: Nucleic Acid Primer

<400> SEQUENCE: 24
gcttcgtcgc cgctacgcgt ggggccgga                               29

<210> SEQ ID NO 25
<211> LENGTH: 27
<212> TYPE: DNA
<213> ORGANISM: Artificial sequence
<220> FEATURE:

-continued

```
<223> OTHER INFORMATION: Nucleic Acid Primer

<400> SEQUENCE: 25
atcgattgag cgagaagagc agacacc                                            27

<210> SEQ ID NO 26
<211> LENGTH: 28
<212> TYPE: DNA
<213> ORGANISM: Artificial sequence
<220> FEATURE:
<223> OTHER INFORMATION: Nucleic Acid Primer

<400> SEQUENCE: 26
agatcttgcc atccagattt tccagttt                                           28

<210> SEQ ID NO 27
<211> LENGTH: 20
<212> TYPE: DNA
<213> ORGANISM: Artificial sequence
<220> FEATURE:
<223> OTHER INFORMATION: Nucleic Acid Primer

<400> SEQUENCE: 27
cgccgctggg ctgccgggtc                                                    20

<210> SEQ ID NO 28
<211> LENGTH: 20
<212> TYPE: DNA
<213> ORGANISM: Artificial sequence
<220> FEATURE:
<223> OTHER INFORMATION: Nucleic Acid Primer

<400> SEQUENCE: 28
tccatcccga tgtatggggc                                                    20

<210> SEQ ID NO 29
<211> LENGTH: 2560
<212> TYPE: DNA
<213> ORGANISM: Homo sapiens
<220> FEATURE:
<221> NAME/KEY: CDS
<222> LOCATION: (55)..(1674)
<220> FEATURE:
<221> NAME/KEY: misc_feature
<222> LOCATION: (1)..(2560)
<223> OTHER INFORMATION: DNA sequence of FIG 1-2 containing SEQ ID NO:3
      encoding for protein of SEQ ID NO:1
<220> FEATURE:
<221> NAME/KEY: mat_peptide
<222> LOCATION: (55)..()

<400> SEQUENCE: 29
gcagcaccca cctgagcgag aagagcagac accgtgctcc tggaatcacc cagc atg          57
                                                              Met
                                                              1 ttg caa ggt ctc ctg cca gtc agt ctc ctc ctc tct gtt gca gta agt         105
Leu Gln Gly Leu Leu Pro Val Ser Leu Leu Leu Ser Val Ala Val Ser
              5                  10                  15 gct ata aaa gaa ctc cct ggg gtg aag aag tat gaa gtg gtt tat cct         153
Ala Ile Lys Glu Leu Pro Gly Val Lys Lys Tyr Glu Val Val Tyr Pro
         20                  25                  30 ata aga ctt cat cca ctg cat aaa aga gag gcc aaa gag cca gag caa         201
Ile Arg Leu His Pro Leu His Lys Arg Glu Ala Lys Glu Pro Glu Gln
     35                  40                  45 cag gaa caa ttt gaa act gaa tta aag tat aaa atg aca att aat gga         249
Gln Glu Gln Phe Glu Thr Glu Leu Lys Tyr Lys Met Thr Ile Asn Gly
```

```
                50                  55                  60                  65
aaa att gca gtg ctt tat ttg aaa aaa aac aag aac ctc ctt gca cca      297
Lys Ile Ala Val Leu Tyr Leu Lys Lys Asn Lys Asn Leu Leu Ala Pro
                    70                  75                  80 ggc tac acg gaa aca tat tat aat tcc act gga aag gag atc acc aca      345
Gly Tyr Thr Glu Thr Tyr Tyr Asn Ser Thr Gly Lys Glu Ile Thr Thr
                85                  90                  95 agc cca caa att atg gat gat tgt tat tat caa gga cat att ctt aat      393
Ser Pro Gln Ile Met Asp Asp Cys Tyr Tyr Gln Gly His Ile Leu Asn
            100                 105                 110 gaa aag gtt tct gac gct agc atc agc aca tgt agg ggt cta agg ggc      441
Glu Lys Val Ser Asp Ala Ser Ile Ser Thr Cys Arg Gly Leu Arg Gly
        115                 120                 125 tac ttc agt cag ggg gat caa aga tac ttt att gaa cct tta agc ccc      489
Tyr Phe Ser Gln Gly Asp Gln Arg Tyr Phe Ile Glu Pro Leu Ser Pro
130                 135                 140                 145 ata cat cgg gat gga cag gag cat gca ctc ttc aag tat aac cct gat      537
Ile His Arg Asp Gly Gln Glu His Ala Leu Phe Lys Tyr Asn Pro Asp
                    150                 155                 160 gaa aag aat tat gac agc acc tgt ggg atg gat ggt gtg ttg tgg gcc      585
Glu Lys Asn Tyr Asp Ser Thr Cys Gly Met Asp Gly Val Leu Trp Ala
                165                 170                 175 cac gat ttg cag cag aac att gcc cta cct gcc acc aaa cta gta aaa      633
His Asp Leu Gln Gln Asn Ile Ala Leu Pro Ala Thr Lys Leu Val Lys
            180                 185                 190 ttg aaa gac agg aag gtt cag gaa cat gag aaa tac ata gaa tat tat      681
Leu Lys Asp Arg Lys Val Gln Glu His Glu Lys Tyr Ile Glu Tyr Tyr
        195                 200                 205 ttg gtc ctg gat aat ggt gag ttt aaa agg tac aat gag aat caa gat      729
Leu Val Leu Asp Asn Gly Glu Phe Lys Arg Tyr Asn Glu Asn Gln Asp
210                 215                 220                 225 gag atc aga aag agg gta ttt gag atg gct aat tat gtc aac atg ctt      777
Glu Ile Arg Lys Arg Val Phe Glu Met Ala Asn Tyr Val Asn Met Leu
                    230                 235                 240 tat aaa aag ctc aat act cat gtg gcc tta gtt ggt atg gaa atc tgg      825
Tyr Lys Lys Leu Asn Thr His Val Ala Leu Val Gly Met Glu Ile Trp
                245                 250                 255 act gac aag gat aag ata aag ata acc cca aat gca agc ttc acc ttg      873
Thr Asp Lys Asp Lys Ile Lys Ile Thr Pro Asn Ala Ser Phe Thr Leu
            260                 265                 270 gag aat ttt tct aaa tgg agg ggg agt gtt ctc tca aga aga aag cgt      921
Glu Asn Phe Ser Lys Trp Arg Gly Ser Val Leu Ser Arg Arg Lys Arg
        275                 280                 285 cat gat att gct cag tta atc aca gca aca gaa ctt gct gga acg act      969
His Asp Ile Ala Gln Leu Ile Thr Ala Thr Glu Leu Ala Gly Thr Thr
290                 295                 300                 305 gtg ggt ctt gca ttt atg tct aca atg tgt tct cct tat tct gtt ggc     1017
Val Gly Leu Ala Phe Met Ser Thr Met Cys Ser Pro Tyr Ser Val Gly
                    310                 315                 320 gtt gtt cag gac cac agc gat aat ctt ctt aga gtt gca ggg aca atg     1065
Val Val Gln Asp His Ser Asp Asn Leu Leu Arg Val Ala Gly Thr Met
                325                 330                 335 gca cat gaa atg ggc cac aac ttt gga atg ttt cat gac gac tat tct     1113
Ala His Glu Met Gly His Asn Phe Gly Met Phe His Asp Asp Tyr Ser
            340                 345                 350 tgc aag tgt cct tct aca ata tgt gtg atg gac aaa gca ctg agc ttc     1161
Cys Lys Cys Pro Ser Thr Ile Cys Val Met Asp Lys Ala Leu Ser Phe
        355                 360                 365 tat ata ccc aca gac ttc agt tcc tgc agc cgt ctc agc tat gac aag     1209
```

-continued

| | | |
|---|---|---|
| Tyr Ile Pro Thr Asp Phe Ser Ser Cys Ser Arg Leu Ser Tyr Asp Lys<br>370                     375                    380                   385 | | |
| ttt ttt gaa gat aaa tta tca aat tgc ctc ttt aat gct cca ttg cct<br>Phe Phe Glu Asp Lys Leu Ser Asn Cys Leu Phe Asn Ala Pro Leu Pro<br>                    390                    395                    400 | | 1257 |
| aca gat atc ata tcc act cca att tgt ggg aac cag ttg gtg gaa atg<br>Thr Asp Ile Ile Ser Thr Pro Ile Cys Gly Asn Gln Leu Val Glu Met<br>                 405                    410                    415 | | 1305 |
| gga gag gac tgt gat tgt ggg aca tct gag gaa tgt acc aat att tgc<br>Gly Glu Asp Cys Asp Cys Gly Thr Ser Glu Glu Cys Thr Asn Ile Cys<br>420                     425                    430 | | 1353 |
| tgt gat gct aag aca tgt aaa atc aaa gca act ttt caa tgt gca tta<br>Cys Asp Ala Lys Thr Cys Lys Ile Lys Ala Thr Phe Gln Cys Ala Leu<br>                 435                    440                    445 | | 1401 |
| gga gaa tgt tgt gaa aaa tgc caa ttt aaa aag gct ggg atg gtg tgc<br>Gly Glu Cys Cys Glu Lys Cys Gln Phe Lys Lys Ala Gly Met Val Cys<br>450                     455                    460                   465 | | 1449 |
| aga cca gca aaa gat gag tgc gac ctg cct gaa atg tgt aat ggt aaa<br>Arg Pro Ala Lys Asp Glu Cys Asp Leu Pro Glu Met Cys Asn Gly Lys<br>                      470                    475                    480 | | 1497 |
| tct ggt aat tgt cct gat gat aga ttc caa gtc aat ggc ttc cct tgc<br>Ser Gly Asn Cys Pro Asp Asp Arg Phe Gln Val Asn Gly Phe Pro Cys<br>                 485                    490                    495 | | 1545 |
| cat cac ggg aag ggc cac tgc ttg atg ggc aca tgc ccc aca ctg cag<br>His His Gly Lys Gly His Cys Leu Met Gly Thr Cys Pro Thr Leu Gln<br>                 500                    505                    510 | | 1593 |
| gag cag tgc aca gag ctg tgg gga cca ggt agg agg aca aat cct ttc<br>Glu Gln Cys Thr Glu Leu Trp Gly Pro Gly Arg Arg Thr Asn Pro Phe<br>515                     520                    525 | | 1641 |
| ccc tgt gca tgt gcg aag gaa aat cat ttc aga tgacagtgtt taaccatggt<br>Pro Cys Ala Cys Ala Lys Glu Asn His Phe Arg<br>530                    535                    540 | | 1694 |
| caaaggacca ttctgtccta tccttcttag aagcttcgaa ctcaaaatca tggaaaggtt | | 1754 |
| ttaagatttg aggttggttt tagggttgct agatttagca agtaaaaata aggatggccc | | 1814 |
| cgttaaattt taacttaaaa ttaacaagtt ttttgttaat ttttttgtttt ttgtctcagc | | 1874 |
| atcagtatat cccatgcaat acttgaggtg tgctcatact aaaattattt gtgtatctga | | 1934 |
| aattcaaatt aaactgggtg tcttttttctt ttcatctggc aaccctacta agatcataaa | | 1994 |
| cccttggaaa tctgtgtgtg tgcgggtgtg tgtgtgtgtg tgtgtgcagg ggtggcagaa | | 2054 |
| gtactgtggg atgggacaga aataagaaaa gatggaaaaa agaaaagaac tctggaaatg | | 2114 |
| cagaaagcca ataagaaaa gtgaaagttc ttaaatggtc gctttgtcca taatgccaaa | | 2174 |
| attttagaga ccatattctc taatttcacc aagaaaactt gaaaaataaa agtttaaaga | | 2234 |
| gatatccgaa aatttaaaca gcaatttgta tagtattaaa taactttggc caggtgcggt | | 2294 |
| ggctcacacc tgtaatccca gcactttggg aggctgaggc gggcggatca cgaggtcagg | | 2354 |
| agatcaagac catcctggct arcacggtga aaccccgtct ctactaaaaa tacaaaaaat | | 2414 |
| tagccgggcg tgctagtggg cgcctgtccc agctactcgg gaggctgagg caggagaagg | | 2474 |
| gcctgaaccc aggaggcgga gcttgccgtc agcagagatc gtgccactgc actccagcct | | 2534 |
| gggtgacaaa gccagactcc gtttcc | | 2560 |

<210> SEQ ID NO 30
<211> LENGTH: 540
<212> TYPE: PRT
<213> ORGANISM: Homo sapiens
<220> FEATURE:

-continued

```
<221> NAME/KEY: misc_feature
<222> LOCATION: (1)..(2560)
<223> OTHER INFORMATION: DNA sequence of FIG 1-2 containing SEQ ID NO:3
      encoding for protein of SEQ ID NO:

<400> SEQUENCE: 30
```

Met Leu Gln Gly Leu Pro Val Ser Leu Leu Ser Val Ala Val
1               5                   10                  15

Ser Ala Ile Lys Glu Leu Pro Gly Val Lys Lys Tyr Glu Val Val Tyr
            20                  25                  30

Pro Ile Arg Leu His Pro Leu His Lys Arg Glu Ala Lys Glu Pro Glu
            35                  40                  45

Gln Gln Glu Gln Phe Glu Thr Glu Leu Lys Tyr Lys Met Thr Ile Asn
        50                  55                  60

Gly Lys Ile Ala Val Leu Tyr Leu Lys Lys Asn Lys Asn Leu Leu Ala
65                  70                  75                  80

Pro Gly Tyr Thr Glu Thr Tyr Tyr Asn Ser Thr Gly Lys Glu Ile Thr
            85                  90                  95

Thr Ser Pro Gln Ile Met Asp Asp Cys Tyr Tyr Gln Gly His Ile Leu
            100                 105                 110

Asn Glu Lys Val Ser Asp Ala Ser Ile Ser Thr Cys Arg Gly Leu Arg
            115                 120                 125

Gly Tyr Phe Ser Gln Gly Asp Gln Arg Tyr Phe Ile Glu Pro Leu Ser
        130                 135                 140

Pro Ile His Arg Asp Gly Gln Glu His Ala Leu Phe Lys Tyr Asn Pro
145                 150                 155                 160

Asp Glu Lys Asn Tyr Asp Ser Thr Cys Gly Met Asp Gly Val Leu Trp
                165                 170                 175

Ala His Asp Leu Gln Gln Asn Ile Ala Leu Pro Ala Thr Lys Leu Val
            180                 185                 190

Lys Leu Lys Asp Arg Lys Val Gln Glu His Glu Lys Tyr Ile Glu Tyr
        195                 200                 205

Tyr Leu Val Leu Asp Asn Gly Glu Phe Lys Arg Tyr Asn Glu Asn Gln
    210                 215                 220

Asp Glu Ile Arg Lys Arg Val Phe Glu Met Ala Asn Tyr Val Asn Met
225                 230                 235                 240

Leu Tyr Lys Lys Leu Asn Thr His Val Ala Leu Val Gly Met Glu Ile
                245                 250                 255

Trp Thr Asp Lys Asp Lys Ile Lys Ile Thr Pro Asn Ala Ser Phe Thr
            260                 265                 270

Leu Glu Asn Phe Ser Lys Trp Arg Gly Ser Val Leu Ser Arg Arg Lys
        275                 280                 285

Arg His Asp Ile Ala Gln Leu Ile Thr Ala Thr Glu Leu Ala Gly Thr
    290                 295                 300

Thr Val Gly Leu Ala Phe Met Ser Thr Met Cys Ser Pro Tyr Ser Val
305                 310                 315                 320

Gly Val Val Gln Asp His Ser Asp Asn Leu Leu Arg Val Ala Gly Thr
                325                 330                 335

Met Ala His Glu Met Gly His Asn Phe Gly Met Phe His Asp Asp Tyr
            340                 345                 350

Ser Cys Lys Cys Pro Ser Thr Ile Cys Val Met Asp Lys Ala Leu Ser
        355                 360                 365

Phe Tyr Ile Pro Thr Asp Phe Ser Ser Cys Ser Arg Leu Ser Tyr Asp
    370                 375                 380

-continued

| | | | | | | | | | | | | | | | |
|---|---|---|---|---|---|---|---|---|---|---|---|---|---|---|---|
|Lys|Phe|Phe|Glu|Asp|Lys|Leu|Ser|Asn|Cys|Leu|Phe|Asn|Ala|Pro|Leu|
|385| | | | |390| | | |395| | | |400| | |

| | | | | | | | | | | | |
|---|---|---|---|---|---|---|---|---|---|---|---|
|Pro|Thr|Asp|Ile|Ile|Ser|Thr|Pro|Ile|Cys|Gly|Asn|Gln|Leu|Val|Glu|
| | | | |405| | | | |410| | | | |415| |

Met Gly Glu Asp Cys Asp Cys Gly Thr Ser Glu Cys Thr Asn Ile
            420             425             430

Cys Cys Asp Ala Lys Thr Cys Lys Ile Lys Ala Thr Phe Gln Cys Ala
            435             440             445

Leu Gly Glu Cys Cys Glu Lys Cys Gln Phe Lys Lys Ala Gly Met Val
            450             455             460

Cys Arg Pro Ala Lys Asp Glu Cys Asp Leu Pro Glu Met Cys Asn Gly
465             470             475             480

Lys Ser Gly Asn Cys Pro Asp Asp Arg Phe Gln Val Asn Gly Phe Pro
                485             490             495

Cys His His Gly Lys Gly His Cys Leu Met Gly Thr Cys Pro Thr Leu
            500             505             510

Gln Glu Gln Cys Thr Glu Leu Trp Gly Pro Gly Arg Arg Thr Asn Pro
            515             520             525

Phe Pro Cys Ala Cys Ala Lys Glu Asn His Phe Arg
            530             535             540

<210> SEQ ID NO 31
<211> LENGTH: 2828
<212> TYPE: DNA
<213> ORGANISM: Homo sapiens
<220> FEATURE:
<221> NAME/KEY: CDS
<222> LOCATION: (55)..(2379)
<220> FEATURE:
<221> NAME/KEY: mat_peptide
<222> LOCATION: (55)..()
<220> FEATURE:
<221> NAME/KEY: misc_feature
<222> LOCATION: (1)..(2828)
<223> OTHER INFORMATION: DNA sequence of FIG 3-4 containing SEQ ID NO:16
      encoding for protein of SEQ ID NO:1

<400> SEQUENCE: 31

```
gcagcaccca cctgagcgag aagagcagac accgtgctcc tggaatcacc cagc atg      57
                                                              Met
                                                              1 ttg caa ggt ctc ctg cca gtc agt ctc ctc ctc tct gtt gca gta agt     105
Leu Gln Gly Leu Leu Pro Val Ser Leu Leu Leu Ser Val Ala Val Ser
           5                  10                  15 gct ata aaa gaa ctc cct ggg gtg aag aag tat gaa gtg gtt tat cct     153
Ala Ile Lys Glu Leu Pro Gly Val Lys Lys Tyr Glu Val Val Tyr Pro
         20                  25                  30 ata aga ctt cat cca ctg cat aaa aga gag gcc aaa gag cca gag caa     201
Ile Arg Leu His Pro Leu His Lys Arg Glu Ala Lys Glu Pro Glu Gln
     35                  40                  45 cag gaa caa ttt gaa act gaa tta aag tat aaa atg aca att aat gga     249
Gln Glu Gln Phe Glu Thr Glu Leu Lys Tyr Lys Met Thr Ile Asn Gly
 50                  55                  60                  65 aaa att gca gtg ctt tat ttg aaa aaa aac aag aac ctc ctt gca cca     297
Lys Ile Ala Val Leu Tyr Leu Lys Lys Asn Lys Asn Leu Leu Ala Pro
                 70                  75                  80 ggc tac acg gaa aca tat tat aat tcc act gga aag gag atc acc aca     345
Gly Tyr Thr Glu Thr Tyr Tyr Asn Ser Thr Gly Lys Glu Ile Thr Thr
             85                  90                  95 agc cca caa att atg gat gat tgt tat tat caa gga cat att ctt aat     393
Ser Pro Gln Ile Met Asp Asp Cys Tyr Tyr Gln Gly His Ile Leu Asn
```

-continued

```
            100                 105                 110
gaa aag gtt tct gac gct agc atc agc aca tgt agg ggt cta agg ggc      441
Glu Lys Val Ser Asp Ala Ser Ile Ser Thr Cys Arg Gly Leu Arg Gly
        115                 120                 125 tac ttc agt cag ggg gat caa aga tac ttt att gaa cct tta agc ccc      489
Tyr Phe Ser Gln Gly Asp Gln Arg Tyr Phe Ile Glu Pro Leu Ser Pro
130                 135                 140                 145 ata cat cgg gat gga cag gag cat gca ctc ttc aag tat aac cct gat      537
Ile His Arg Asp Gly Gln Glu His Ala Leu Phe Lys Tyr Asn Pro Asp
                150                 155                 160 gaa aag aat tat gac agc acc tgt ggg atg gat ggt gtg ttg tgg gcc      585
Glu Lys Asn Tyr Asp Ser Thr Cys Gly Met Asp Gly Val Leu Trp Ala
            165                 170                 175 cac gat ttg cag cag aac att gcc cta cct gcc acc aaa cta gta aaa      633
His Asp Leu Gln Gln Asn Ile Ala Leu Pro Ala Thr Lys Leu Val Lys
        180                 185                 190 ttg aaa gac agg aag gtt cag gaa cat gag aaa tac ata gaa tat tat      681
Leu Lys Asp Arg Lys Val Gln Glu His Glu Lys Tyr Ile Glu Tyr Tyr
    195                 200                 205 ttg gtc ctg gat aat ggt gag ttt aaa agg tac aat gag aat caa gat      729
Leu Val Leu Asp Asn Gly Glu Phe Lys Arg Tyr Asn Glu Asn Gln Asp
210                 215                 220                 225 gag atc aga aag agg gta ttt gag atg gct aat tat gtc aac atg ctt      777
Glu Ile Arg Lys Arg Val Phe Glu Met Ala Asn Tyr Val Asn Met Leu
                230                 235                 240 tat aaa aag ctc aat act cat gtg gcc tta gtt ggt atg gaa atc tgg      825
Tyr Lys Lys Leu Asn Thr His Val Ala Leu Val Gly Met Glu Ile Trp
            245                 250                 255 act gac aag gat aag ata aag ata acc cca aat gca agc ttc acc ttg      873
Thr Asp Lys Asp Lys Ile Lys Ile Thr Pro Asn Ala Ser Phe Thr Leu
        260                 265                 270 gag aat ttt tct aaa tgg agg ggg agt gtt ctc tca aga aga aag cgt      921
Glu Asn Phe Ser Lys Trp Arg Gly Ser Val Leu Ser Arg Arg Lys Arg
    275                 280                 285 cat gat att gct cag tta atc aca gca aca gaa ctt gct gga acg act      969
His Asp Ile Ala Gln Leu Ile Thr Ala Thr Glu Leu Ala Gly Thr Thr
290                 295                 300                 305 gtg ggt ctt gca ttt atg tct aca atg tgt tct cct tat tct gtt ggc     1017
Val Gly Leu Ala Phe Met Ser Thr Met Cys Ser Pro Tyr Ser Val Gly
                310                 315                 320 gtt gtt cag gac cac agc gat aat ctt ctt aga gtt gca ggg aca atg     1065
Val Val Gln Asp His Ser Asp Asn Leu Leu Arg Val Ala Gly Thr Met
            325                 330                 335 gca cat gaa atg ggc cac aac ttt gga atg ttt cat gac gac tat tct     1113
Ala His Glu Met Gly His Asn Phe Gly Met Phe His Asp Asp Tyr Ser
        340                 345                 350 tgc aag tgt cct tct aca ata tgt gtg atg gac aaa gca ctg agc ttc     1161
Cys Lys Cys Pro Ser Thr Ile Cys Val Met Asp Lys Ala Leu Ser Phe
    355                 360                 365 tat ata ccc aca gac ttc agt tcc tgc agc cgt ctc agc tat gac aag     1209
Tyr Ile Pro Thr Asp Phe Ser Ser Cys Ser Arg Leu Ser Tyr Asp Lys
370                 375                 380                 385 ttt ttt gaa gat aaa tta tca aat tgc ctc ttt aat gct cca ttg cct     1257
Phe Phe Glu Asp Lys Leu Ser Asn Cys Leu Phe Asn Ala Pro Leu Pro
                390                 395                 400 aca gat atc ata tcc act cca att tgt ggg aac cag ttg gtg gaa atg     1305
Thr Asp Ile Ile Ser Thr Pro Ile Cys Gly Asn Gln Leu Val Glu Met
            405                 410                 415 gga gag gac tgt gat tgt ggg aca tct gag gaa tgt acc aat att tgc     1353
```

-continued

| | | | | | | | | | | | | | | |
|---|---|---|---|---|---|---|---|---|---|---|---|---|---|---|
| Gly | Glu | Asp | Cys | Asp | Cys | Gly | Thr | Ser | Glu | Glu | Cys | Thr | Asn | Ile | Cys |
| | | 420 | | | | | 425 | | | | | 430 | | |

```
tgt gat gct aag aca tgt aaa atc aaa gca act ttt caa tgt gca tta       1401
Cys Asp Ala Lys Thr Cys Lys Ile Lys Ala Thr Phe Gln Cys Ala Leu
        435                 440                 445 gga gaa tgt tgt gaa aaa tgc caa ttt aaa aag gct ggg atg gtg tgc       1449
Gly Glu Cys Cys Glu Lys Cys Gln Phe Lys Lys Ala Gly Met Val Cys
450                 455                 460                 465 aga cca gca aaa gat gag tgc gac ctg cct gaa atg tgt aat ggt aaa       1497
Arg Pro Ala Lys Asp Glu Cys Asp Leu Pro Glu Met Cys Asn Gly Lys
                470                 475                 480 tct ggt aat tgt cct gat gat aga ttc caa gtc aat ggc ttc cct tgc       1545
Ser Gly Asn Cys Pro Asp Asp Arg Phe Gln Val Asn Gly Phe Pro Cys
        485                 490                 495 cat cac ggg aag ggc cac tgc ttg atg ggg aca tgc ccc aca ctg cag       1593
His His Gly Lys Gly His Cys Leu Met Gly Thr Cys Pro Thr Leu Gln
        500                 505                 510 gag cag tgc aca gag ctg tgg gga cca gga act gag gtt gca gat aag       1641
Glu Gln Cys Thr Glu Leu Trp Gly Pro Gly Thr Glu Val Ala Asp Lys
515                 520                 525 tca tgt tac aac agg aat gaa ggt ggg tca aag tac ggg tac tgt cgc       1689
Ser Cys Tyr Asn Arg Asn Glu Gly Gly Ser Lys Tyr Gly Tyr Cys Arg
530                 535                 540                 545 aga gtg gat gac aca ctc att ccc tgc aaa gca aat gat acc atg tgt       1737
Arg Val Asp Asp Thr Leu Ile Pro Cys Lys Ala Asn Asp Thr Met Cys
            550                 555                 560 ggg aag ttg ttc tgt caa ggt ggg tcg gat aat ttg ccc tgg aaa gga       1785
Gly Lys Leu Phe Cys Gln Gly Gly Ser Asp Asn Leu Pro Trp Lys Gly
                565                 570                 575 cgg ata gtg act ttc ctg aca tgt aaa aca ttt gat cct gaa gac aca       1833
Arg Ile Val Thr Phe Leu Thr Cys Lys Thr Phe Asp Pro Glu Asp Thr
        580                 585                 590 agt caa gaa ata ggc atg gtg gcc aat gga act aag tgt ggc gat aac       1881
Ser Gln Glu Ile Gly Met Val Ala Asn Gly Thr Lys Cys Gly Asp Asn
595                 600                 605 aag gtt tgc att aat gca gaa tgt gtg gat att gag aaa gcc tac aaa       1929
Lys Val Cys Ile Asn Ala Glu Cys Val Asp Ile Glu Lys Ala Tyr Lys
610                 615                 620                 625 tca acc aat tgc tca tct aag tgc aaa gga cat gct gtg tgt gac cat       1977
Ser Thr Asn Cys Ser Ser Lys Cys Lys Gly His Ala Val Cys Asp His
            630                 635                 640 gag ctc cag tgt caa tgt gag gaa gga tgg atc cct ccc gac tgc gat       2025
Glu Leu Gln Cys Gln Cys Glu Glu Gly Trp Ile Pro Pro Asp Cys Asp
                645                 650                 655 gac tcc tca gtg gtc ttc cac ttc tcc att gtg gtt ggg gtg ctg ttc       2073
Asp Ser Ser Val Val Phe His Phe Ser Ile Val Val Gly Val Leu Phe
        660                 665                 670 cca atg gcg gtc att ttt gtg gtg gtt gct atg gta atc cgg cac cag       2121
Pro Met Ala Val Ile Phe Val Val Val Ala Met Val Ile Arg His Gln
675                 680                 685 agc tcc aga gaa aag cag aag aaa gat cag agg cca cta tct acc act       2169
Ser Ser Arg Glu Lys Gln Lys Lys Asp Gln Arg Pro Leu Ser Thr Thr
690                 695                 700                 705 ggc acc agg cca cac aaa cag aag agg aaa ccc cag atg gta aag gct       2217
Gly Thr Arg Pro His Lys Gln Lys Arg Lys Pro Gln Met Val Lys Ala
            710                 715                 720 gtt caa ccc caa gag atg agt cag atg aag ccc cat gtg tat gat ctg       2265
Val Gln Pro Gln Glu Met Ser Gln Met Lys Pro His Val Tyr Asp Leu
                725                 730                 735
```

-continued

```
cca gta gaa ggc aat gag ccc cca gcc tct ttt cat aaa gac aca aac    2313
Pro Val Glu Gly Asn Glu Pro Pro Ala Ser Phe His Lys Asp Thr Asn
        740                 745                 750 gca ctt ccc cct act gtt ttc aag gat aat cca atg tct aca cct aag    2361
Ala Leu Pro Pro Thr Val Phe Lys Asp Asn Pro Met Ser Thr Pro Lys
    755                 760                 765 gac tca aat cca aaa gca tgaagcaaca gctaagcaag aactaatggc           2409
Asp Ser Asn Pro Lys Ala
770             775 taaattatca acttggaaaa ctggaaaatc tggatggcag agaaatatac tatctcacca    2469
gtatttgctc tcgactcaag aaggttaaca ttttctgatt catgttagac tttgaagaga    2529
ctaaagaaaa ttttcaagag gaacatatgc ctgagaacct ttgcatgaat ttaaaatttc    2589
aattatccat tcttataaga aggaagatga ttgtaaagaa atatctccga agttaaaatc    2649
tgtaatagga attgattcat tctctaatga aaacaaaaca taaaacatc acactaatct     2709 tggaggaata agaaaaattg tacatccatt aaatgtacaa ttgattgcaa catcttgatt    2769
gttttaacca ttaacttgtc aaattacaat cacagttaag aaaatgatgt aaaattctg    2828
```

```
<210> SEQ ID NO 32
<211> LENGTH: 775
<212> TYPE: PRT
<213> ORGANISM: Homo sapiens
<220> FEATURE:
<221> NAME/KEY: misc_feature
<222> LOCATION: (1)..(2828)
<223> OTHER INFORMATION: DNA sequence of FIG 3-4 containing SEQ ID NO:16
      encoding for protein of SEQ ID NO:1

<400> SEQUENCE: 32

Met Leu Gln Gly Leu Leu Pro Val Ser Leu Leu Ser Val Ala Val
1               5                   10                  15

Ser Ala Ile Lys Glu Leu Pro Gly Val Lys Lys Tyr Glu Val Tyr
                20                  25                  30

Pro Ile Arg Leu His Pro Leu His Lys Arg Glu Ala Lys Glu Pro Glu
            35                  40                  45

Gln Gln Glu Gln Phe Glu Thr Glu Leu Lys Tyr Lys Met Thr Ile Asn
    50                  55                  60

Gly Lys Ile Ala Val Leu Tyr Leu Lys Lys Asn Lys Asn Leu Leu Ala
65                  70                  75                  80

Pro Gly Tyr Thr Glu Thr Tyr Tyr Asn Ser Thr Gly Lys Glu Ile Thr
                85                  90                  95

Thr Ser Pro Gln Ile Met Asp Asp Cys Tyr Tyr Gln Gly His Ile Leu
            100                 105                 110

Asn Glu Lys Val Ser Asp Ala Ser Ile Ser Thr Cys Arg Gly Leu Arg
        115                 120                 125

Gly Tyr Phe Ser Gln Gly Asp Gln Arg Tyr Phe Ile Glu Pro Leu Ser
    130                 135                 140

Pro Ile His Arg Asp Gly Gln Glu His Ala Leu Phe Lys Tyr Asn Pro
145                 150                 155                 160

Asp Glu Lys Asn Tyr Asp Ser Thr Cys Gly Met Asp Gly Val Leu Trp
                165                 170                 175

Ala His Asp Leu Gln Gln Asn Ile Ala Leu Pro Ala Thr Lys Leu Val
            180                 185                 190

Lys Leu Lys Asp Arg Lys Val Gln Glu His Glu Lys Tyr Ile Glu Tyr
        195                 200                 205

Tyr Leu Val Leu Asp Asn Gly Glu Phe Lys Arg Tyr Asn Glu Asn Gln
```

-continued

```
            210                 215                 220
Asp Glu Ile Arg Lys Arg Val Phe Glu Met Ala Asn Tyr Val Asn Met
225                 230                 235                 240

Leu Tyr Lys Lys Leu Asn Thr His Val Ala Leu Val Gly Met Glu Ile
                245                 250                 255

Trp Thr Asp Lys Asp Lys Ile Lys Ile Thr Pro Asn Ala Ser Phe Thr
                260                 265                 270

Leu Glu Asn Phe Ser Lys Trp Arg Gly Ser Val Leu Ser Arg Arg Lys
                275                 280                 285

Arg His Asp Ile Ala Gln Leu Ile Thr Ala Thr Glu Leu Ala Gly Thr
            290                 295                 300

Thr Val Gly Leu Ala Phe Met Ser Thr Met Cys Ser Pro Tyr Ser Val
305                 310                 315                 320

Gly Val Val Gln Asp His Ser Asp Asn Leu Leu Arg Val Ala Gly Thr
                325                 330                 335

Met Ala His Glu Met Gly His Asn Phe Gly Met Phe His Asp Asp Tyr
                340                 345                 350

Ser Cys Lys Cys Pro Ser Thr Ile Cys Val Met Asp Lys Ala Leu Ser
                355                 360                 365

Phe Tyr Ile Pro Thr Asp Phe Ser Ser Cys Ser Arg Leu Ser Tyr Asp
                370                 375                 380

Lys Phe Phe Glu Asp Lys Leu Ser Asn Cys Leu Phe Asn Ala Pro Leu
385                 390                 395                 400

Pro Thr Asp Ile Ile Ser Thr Pro Ile Cys Gly Asn Gln Leu Val Glu
                405                 410                 415

Met Gly Glu Asp Cys Asp Cys Gly Thr Ser Glu Glu Cys Thr Asn Ile
                420                 425                 430

Cys Cys Asp Ala Lys Thr Cys Lys Ile Lys Ala Thr Phe Gln Cys Ala
                435                 440                 445

Leu Gly Glu Cys Cys Glu Lys Cys Gln Phe Lys Lys Ala Gly Met Val
            450                 455                 460

Cys Arg Pro Ala Lys Asp Glu Cys Asp Leu Pro Glu Met Cys Asn Gly
465                 470                 475                 480

Lys Ser Gly Asn Cys Pro Asp Asp Arg Phe Gln Val Asn Gly Phe Pro
                485                 490                 495

Cys His His Gly Lys Gly His Cys Leu Met Gly Thr Cys Pro Thr Leu
                500                 505                 510

Gln Glu Gln Cys Thr Glu Leu Trp Gly Pro Gly Thr Glu Val Ala Asp
                515                 520                 525

Lys Ser Cys Tyr Asn Arg Asn Glu Gly Gly Ser Lys Tyr Gly Tyr Cys
                530                 535                 540

Arg Arg Val Asp Asp Thr Leu Ile Pro Cys Lys Ala Asn Asp Thr Met
545                 550                 555                 560

Cys Gly Lys Leu Phe Cys Gln Gly Gly Ser Asp Asn Leu Pro Trp Lys
                565                 570                 575

Gly Arg Ile Val Thr Phe Leu Thr Cys Lys Thr Phe Asp Pro Glu Asp
                580                 585                 590

Thr Ser Gln Glu Ile Gly Met Val Ala Asn Gly Thr Lys Cys Gly Asp
                595                 600                 605

Asn Lys Val Cys Ile Asn Ala Glu Cys Val Asp Ile Glu Lys Ala Tyr
                610                 615                 620

Lys Ser Thr Asn Cys Ser Ser Lys Cys Lys Gly His Ala Val Cys Asp
625                 630                 635                 640
```

```
                                                    -continued

His Glu Leu Gln Cys Gln Cys Glu Glu Gly Trp Ile Pro Pro Asp Cys
            645                 650                 655

Asp Asp Ser Ser Val Val Phe His Phe Ser Ile Val Val Gly Val Leu
            660                 665                 670

Phe Pro Met Ala Val Ile Phe Val Val Ala Met Val Ile Arg His
            675                 680             685

Gln Ser Ser Arg Glu Lys Gln Lys Asp Gln Arg Pro Leu Ser Thr
        690             695             700

Thr Gly Thr Arg Pro His Lys Gln Lys Arg Lys Pro Gln Met Val Lys
705             710             715                 720

Ala Val Gln Pro Gln Glu Met Ser Gln Met Lys Pro His Val Tyr Asp
                725             730             735

Leu Pro Val Glu Gly Asn Glu Pro Pro Ala Ser Phe His Lys Asp Thr
            740             745             750

Asn Ala Leu Pro Pro Thr Val Phe Lys Asp Asn Pro Met Ser Thr Pro
            755             760             765

Lys Asp Ser Asn Pro Lys Ala
    770             775
```